(12) United States Patent  (10) Patent No.: US 7,853,319 B2
Davies  (45) Date of Patent:  Dec. 14, 2010

(54) METHOD AND SYSTEM FOR DETECTING ELECTROPHYSIOLOGICAL CHANGES IN PRE-CANCEROUS AND CANCEROUS TISSUE AND EPITHELIUM

(75) Inventor: Richard J. Davies, Saddle River, NJ (US)

(73) Assignee: Epi-Sci, LLC, Saddle River, NJ (US)

( * ) Notice: Subject to any disclaimer, the term of this patent is extended or adjusted under 35 U.S.C. 154(b) by 449 days.

(21) Appl. No.: 11/409,144

(22) Filed: Apr. 21, 2006

(65) Prior Publication Data

US 2006/0241514 A1  Oct. 26, 2006

Related U.S. Application Data

(60) Provisional application No. 60/673,448, filed on Apr. 21, 2005.

(51) Int. Cl.
  *A61B 5/05*  (2006.01)
(52) U.S. Cl. .................................................. 600/547
(58) Field of Classification Search ................. 600/546, 600/407
  See application file for complete search history.

(56) References Cited

U.S. PATENT DOCUMENTS

| | | | |
|---|---|---|---|
| 3,786,801 | A | 1/1974 | Sartorius |
| 3,949,736 | A | 4/1976 | Vrana et al. |
| 4,291,708 | A | 9/1981 | Frei et al. |
| 4,458,694 | A | 7/1984 | Sollish et al. |
| 4,486,835 | A | 12/1984 | Bai et al. |
| 4,729,385 | A * | 3/1988 | Juncosa et al. ............... 600/547 |

(Continued)

FOREIGN PATENT DOCUMENTS

WO  WO-98/23204 A1  6/1998

(Continued)

OTHER PUBLICATIONS

Hope et al. "Technology review: The use of electrical impedance scanning in the detection of breast cancer" Breast Cancer Res. 2004. published Nov. 13, 2003. pp. 69-74. as submitted in IDS.*

(Continued)

*Primary Examiner*—Max Hindenburg
*Assistant Examiner*—Renee Danega
(74) *Attorney, Agent, or Firm*—Lerner, David, Littenberg, Krumholz & Mentlik, LLP

(57) ABSTRACT

A method and system for determining a condition of a selected region of epithelial and stromal tissue, for example in the human breast. A plurality of electrodes are used to measure surface and transepithelial electropotential of breast tissue as well as surface electropotential and impedance at one or more locations and at several defined frequencies, particularly very low frequencies. An agent may be introduced into the region of tissue to enhance electrophysiological characteristics. Measurements made at ambient and varying suction and/or positive pressure applied to the epithelial tissue and/or positive pressure conditions applied to the breast are also used as a diagnostic tool. Tissue condition is determined based on the electropotential and impedance profile at different depths of the epithelium, stroma, tissue, or organ, together with an estimate of the functional changes in the epithelium due to altered ion transport and electrophysiological properties of the tissue. Devices for practicing the disclosed methods are also provided.

2 Claims, 25 Drawing Sheets

U.S. PATENT DOCUMENTS

| | | | |
|---|---|---|---|
| 4,955,383 | A | 9/1990 | Faupel |
| 5,099,844 | A | 3/1992 | Faupel |
| 5,109,849 | A | 5/1992 | Goodman et al. |
| 5,143,079 | A | 9/1992 | Frei et al. |
| 5,345,935 | A | 9/1994 | Hirsch et al. |
| 5,415,164 | A | 5/1995 | Faupel et al. |
| 5,417,222 | A | 5/1995 | Dempsey et al. |
| 5,697,369 | A | 12/1997 | Long, Jr. et al. |
| 5,722,404 | A | 3/1998 | Lundback |
| 5,766,165 | A | 6/1998 | Gentelia et al. |
| 5,810,742 | A | 9/1998 | Pearlman |
| 5,833,622 | A | 11/1998 | Meathrel et al. |
| 5,906,208 | A | 5/1999 | Ishikawa |
| 6,026,322 | A | 2/2000 | Korenman et al. |
| 6,122,544 | A | 9/2000 | Organ |
| 6,134,480 | A | 10/2000 | Minogue et al. |
| 6,135,953 | A | 10/2000 | Carim |
| 6,138,044 | A | 10/2000 | Svedman |
| 6,148,232 | A | 11/2000 | Avrahami et al. |
| 6,251,681 | B1 | 6/2001 | Davies et al. |
| 6,308,097 | B1 | 10/2001 | Pearlman |
| 6,312,428 | B1 | 11/2001 | Eggers et al. |
| 6,314,315 | B1 | 11/2001 | Hung |
| 6,328,735 | B1 | 12/2001 | Curley et al. |
| 6,363,275 | B1 | 3/2002 | Kaiser |
| 6,389,305 | B1 | 5/2002 | Deban et al. |
| 6,456,865 | B2 | 9/2002 | Samson |
| 6,471,660 | B1 | 10/2002 | Covington |
| 6,496,725 | B2 | 12/2002 | Kamada et al. |
| 6,500,173 | B2 | 12/2002 | Underwood et al. |
| 6,641,604 | B1 | 11/2003 | Adelman et al. |
| 6,773,418 | B1 | 8/2004 | Sharrow et al. |
| 6,823,203 | B2 | 11/2004 | Jordan |
| 6,887,239 | B2 | 5/2005 | Elstrom et al. |
| 6,898,303 | B2 | 5/2005 | Armato, III et al. |
| 6,922,586 | B2 | 7/2005 | Davies |
| 6,993,383 | B2 * | 1/2006 | Assenheimer ............... 600/547 |
| 7,223,239 | B2 | 5/2007 | Schulze et al. |
| 2001/0051774 | A1 | 12/2001 | Littrup et al. |
| 2002/0006216 | A1 | 1/2002 | Armato et al. |
| 2002/0026123 | A1* | 2/2002 | Pearlman .................... 600/547 |
| 2002/0188187 | A1 | 12/2002 | Jordan |
| 2003/0010987 | A1 | 1/2003 | Banin et al. |
| 2003/0109871 | A1 | 6/2003 | Johnson et al. |
| 2003/0216661 | A1 | 11/2003 | Davies |
| 2004/0152997 | A1 | 8/2004 | Davies |
| 2004/0253652 | A1* | 12/2004 | Davies ...................... 435/7.23 |
| 2005/0059928 | A1 | 3/2005 | Larsson |
| 2005/0203436 | A1 | 9/2005 | Davies |

FOREIGN PATENT DOCUMENTS

| | | |
|---|---|---|
| WO | 9923945 | 5/1999 |
| WO | 0035357 | 6/2000 |
| WO | 0232335 | 4/2002 |

OTHER PUBLICATIONS

Foster KR, Schwan HP. Dielectric Properties Of Tissues And Biological Materials: A Critical Review. Critical Reviews in Biomedical Engineering, 1989, pp. 25-104 vol. 17, Issue 1, CRC Press, England.
Emtestam L, Ollmar S. Electrical Impedance Index In Human Skin: Measurements After Occlusion, In 5 Anatomical Regions And In Mild Irritant Contact Dermatitis. Contact Dermatitis Environmental and Occupational Dermatitis, Feb. 1993, pp. 104-108, vol. 28, No. 2, RJG Rycroft, London, England.
Ollmar S, Eek A, Sundstrom F, Emtestam L. Electrical Impedance For Estimation Of Irritation in Oral Mucosa And Skin. Medical Progress Technology, Feb. 1995, pp. 29-37, vol. 21. No. 1, Kluwer Academic Publishers.
Ollmar S, Nyren M, Nicander I, Emtestam L. Electrical Impedance Compared With Other Non-Invasive Bioengineering Techniques And Visual Scoring For Detection Of Irritation In Human Skin, British Journal of Dermatology, Jan. 1994, pp. 29-36, vol. 130, No. 1, Blackwell Scientific Publications.
Nicander I, Ollmar S, Rozell BL, Eek A, Emtestam L. Electrical Impedance Measureed To Five Skin Depths In Mild Irritant Dermatitis Induced By Sodium Lauryl Sulphate, British Journal of Dermatology, May 1995, pp. 718-724, vol. 132, No. 5, Blackwell Scientific Publications.
Kristt D, Winston GJ, Mellov MM, Veltman V, Koren R. Patterns Of Proliferative Changes In Crypts Bordering Colonic Tumors: Zonal Histology And Cell Cycle Marker Expression. Pathology Oncology Research, 1999; pp. 297-303, vol. 5, No. 4.
Lackermeier AH, McAdams ET, Moss GP, Woolfson AD. In Vivo Ac Impedance Spectroscopy Of Human Skin. Theory And Problems In Monitoring Of Passive Percutaneous Drug Delivery. Annals of the New York Academy of Sciences, 1999, pp. 197-213, vol. 873.
Cuzick J, Holland R, Barth V, Davies R, Faupel M, Fentiman I et al. Electropotential Measurements As A New Diagnostic Modality For Breast Cancer. The Lancet, Aug. 1998, pp. 359-363, vol. 352, No. 9125.
Faupel M, Vanel D, Barth V, Davies R, Fentiman IS, Holland R et al. Electropotential Evaluation As A New Technique For Diagnosing Breast Lesions. European Journal of Radiology, Jan. 1997, pp. 33-38. vol. 24, No. 1, Elsevier.
Hülser DF, Frank W. Stimulation Of Embryonic Rat Cell In Culture By A Protein Fraction Isolated From Fetal Calf Serum, Publishing House of the Periodical for Nature Research, Jul. 1971, pp. 1045-1048, vol. 26b, No. 7.
Moolenaar WH, De Laat SW, Van Der Saag PT. Serum Triggers A Sequence Of Rapid Ionic Conductance Changes In Quiescent Neuroblastoma Cells, Nature, Jun. 14, 1979, pp. 721-723, vol. 279, No. 5714.
Reuss L, Cassel D, Rothenberg P, Whiteley P, Mancuso D, Glaser L. Mitogens And Ion Fluxes. In: Mandel LJ, Benos DJ, Editors. The Role Of Membranes In Cell Growth And Differentiation, Academic Press Inc., Hartcourt Brace Jovanovich, 1986, pp. 3-54, vol. 27, Orlando, Fla.
Moolenaar WH, De Laat SW, Mummery CL, Van Der Saag PT. Na+/H+ Exchange In The Action Of Growth Factors. In: Boynton AL, McKeehan WL, Whitfield JF, editors. Ions, Cell Proliferation and Cancer, Academic Press, Inc., 1982, pp. 151-162, New York.
Rothenberg P, Reuss L, Glaser L. Serum And Epidermal Growth Factor Transiently Depolarize Quiescent BSC- 1 Epithelial Cells, Proceedings of the National Academy of Sciences of The United States of America, Dec. 1982, pp. 7783-7787, vol. 79, No. 24.
Schultz SG. Homocellular Regulatory Mechanisms In Sodium-Transporting Epithelia: Avoidance Of Extinction By "Flush-Through", American Journal of Physiology, Dec. 1981, pp. F579-F590, vol. 241, No. 6, The American Physiological Society.
Boonstra J, Moolenaar WH, Harrison PH, Moed P, Van Der Saag PT, De Laat SW. Ionic Responses And Growth Stimulation Induced By Nerve Growth Factor And Epidermal Growth Factor In Rat Pheochromocytoma (PC12) cells, The Journal of Cell Biology, Jul. 1983, pp. 92-98, vol. 97, No. 1, The Rockefeller University Press.
Redmann K, Walliser S. Different Changes In Transmembrane Potential Of Cultured Cells After Ouabain-Inhibited Active Na+/K+-Transport. Archie Fur Geschwulstforsch, 1981; pp. 96-102. vol. 51, No. 1, Volk und Gesundheit, Berlin.
Prat AG, Cunningham CC, Jackson GR, Jr., Borkan SC, Wang Y, Ausiello DA et al. Actin Filament Organization Is Required For Proper Camp-Dependent Activation Of CFTR., American Journal of Physiology, Dec. 1999, pp. C1160-C1169 vol. 277, No. 6 Part 1, The American Physiology Society.
Rouzaire-Dubois B, Milandri JB, Bostel S, Dubois JM. Control Of Cell Proliferation By Cell Volume Alterations In Rat C6 Glioma Cells. Pflugers Archiv European Journal of Physiology, Oct. 2000, vol. 440, No. 6, Springer.
Ernst M, Adam G. Regulation Of Passive Potassium Transport Of Normal And Transformed 3T3 Mouse Cell Cultures By External Calcium Concentration And Temperature. Journal of Member Biology, 1981; pp. 155-172, vol. 61, No. 3, Springer-Verlag New York Inc.

Diserbo M, Fatome M, Verdetti J. Activation Of Large Conductance Ca(2+)-Activated K+ Channels In N1E-115 Neuroblastoma Cells By Platelet-Activating Factor. Biochemical and Biophysical Research Community, Jan. 1996, pp. 745-749, vol. 218, No. 3, Academic Press.

Rane SG. A Ca2(+)-Activated K+ Current In Ras-Transformed Fibroblasts Is Absent From Nontransformed Cells, American Journal of Physiology, Jan. 1991, pp. C104-C112, vol. 260, No. 1, Part 1, The American Physiological Society.

Sachs HG, Stambrook PJ, Ebert JD. Changes In Membrane Potential During The Cell Cycle, Experimental Cell Research, Feb. 1974, pp. 362-366, vol. 83, No. 2, Academic Press, New York and London.

Kiefer H, Blume AJ, Kaback HR. Membrane Potential Changes During Mitogenic Stimulation Of Mouse Spleen Lymphocytes, Proceedings of the National Academy of Sciences, of the United States of America, Apr. 1980, pp. 2200-2204, vol. 77, No. 4.

Moolenaar WH, Mummery CL, Van Der Saag PT, De Laat SW. Rapid Ionic Events And The Initiation Of Growth In Serum-Stimulated Neuroblastoma Cells, Cell Mar. 1981, pp. 789-798, vol. 23, No. 3.

Chapman LM, Wondergem R. Transmembrane Potential And Intracellular Potassium Ion Activity In Fetal And Maternal Liver, Journal of Cellular Physiology, Oct. 1984, pp. 7-12, vol. 121, No. 1, Alan R. Liss, Inc.

Decoursey TE, Cherny VV. Voltage-Activated Proton Currents In Human THP-1 Monocytes, The Journal of Membrane Biology, Jul. 1996, pp. 131-140, vol. 152, No. 2, Springer.

Kapural L, Fein A. Changes In The Expression Of Voltage-Gated K+ Currents During Development Of Human Megakaryocytic Cells, Biochimica et Biophysica Acta 1997, pp. 319-328; vol. 1326, No. 2, Elsevier, USA.

Wieland SJ, Chou RH, Chen TA. Elevation Of A Potassium Current In Differentiating Human Leukemic (HI- 60) Cells, Journal of Cell Physiology, Aug. 1987, pp. 371-375, vol. 132, No. 2, Alan R. Liss, Inc.

Simonneau M, Distasi C, Tauc L, Poujeoi C. Development Of Ionic Channels During Mouse Neuronal Differentiation, Journal de Physiologie, 1985, pp. 312-332, vol. 80, No. 2, Masson, Paris, France.

Veselovskii NS, Fomina AF. [Sodium And Calcium Channels Of The Somatic Membrane Of Neuroblastoma Cells During Artifically Induced Differentiation]. Neirofiziologiia 1986; pp. 207-214, vol. 18, No. 2.

Vyklicky L, Jr., Michl J, Vlachova V, Vyklicky L, Vyskocil F. Ionic Currents In Neuroblastoma Clone E-7 Cells, Neuroscience Letters, 1985, pp. 197-201, vol. 55, No. 2, Elsevier Scientific Publishers, Ireland.

Felber SM, Brand MD. Concanavalin A Causes An Increase In Sodium Permeability And Intracellular Sodium Content Of Pig Lymphocytes, The Biochemical Journal, Mar. 1983, pp. 893-897, vol. 210, No. 3, The Biochemical Society, London.

O'Donnell ME, Villereal ML. Membrane Potential And Sodium Flux In Neuroblastoma X Glioma Hybrid Cells: Effects Of Amiloride And Serum, Journal of Cellular Physiology, Dec. 1982, pp. 405-412, vol. 113, No. 3, Alan R. Liss, Inc.

Leffert HL, Koch KS. Ionic Events At The Membrane Initiate Rat Liver Regeneration. Ann The New York Academy of Sciences, 1980, pp. 201-215, vol. 339, New York, USA.

Villereal ML. Sodium Fluxes In Human Fibroblasts: Effect Of Serum, Ca+2, And Amiloride. Journal of Cellular Physiology, Jun. 1981, pp. 359-369, vol. 107, No. 3, Alan R. Liss, Inc.

Fehlmann M, Canivet B, Freychet P. Epidermal Growth Factor Stimulates Monovalent Cation Transport In Isolated Rat Hepatocytes, Biochemical and Biophysical Research Communications, May 1981, pp. 254-260, vol. 100, No. 1, Academic Press Inc.

Moolenaar WH, Tsien RY, Van Der Saag PT, De Laat SW. Na+/H+ Exchange And Cytoplasmic Ph In The Action Of Growth Factors In Human Fibroblasts. Nature, International Weekly Journal of Science, Aug. 1983, pp. 645-648, vol. 304, No. 5927, MacMillan Journals, Ltd.

Paris S, Pouyssegur J. Biochemical Characterization Of The Amiloride-Sensitive Na+/H+ Antiport In Chinese Hamster Lung Fibroblasts, The Journal of Biological Chemistry, Mar. 1983, pp. 3503-3508, vol. 258, No. 6, The American Society of Biological Chemists, Inc., USA.

Paris S, Pouyssegur J. Growth Factors Activate The Na+/H+ Antiporter In Quiescent Fibroblasts By Increasing Its Affinity For Intracellular H+, The Journal of Biological Chemistry, Sep. 1984, pp. 10989-10994, vol. 259, No. 17, The American Society of Biological Chemists, Inc., USA.

Pouyssegur J, Chambard JC, Franchi A, Paris S, Obberghen-Schilling E. Growth Factor Activation Of An Amiloride-Sensitive Na+/H+ Exchange System In Quiescent Fibroblasts: Coupling To Ribosomal Protein S6 Phosphorylation, Proceedings of the National Academy of Sciences of the United States of America, Jul. 1982, pp. 3935-3939, vol. 79, No. 13, National Academy of Sciences, USA.

Pouyssegur J, Sardet C, Franchi A, L'Allemain G, Paris S. A Specific Mutation Abolishing Na+/H+ Antiport Activity In Hamster Fibroblasts Precludes Growth At Neutral And Acidic Ph., Proceedings of the National Academy of Sciences of the United States of America, Aug. 1984, pp. 4833-4837, vol. 81, No. 15, National Academy of Sciences, USA.

Moolenaar WH, Tertoolen LG, De Laat SW. The Regulation Of Cytoplasmic Ph In Human Fibroblasts, The Journal of Biological Chemistry. Jun. 1984, pp. 7563-7569, vol. 259, No. 12, The American Society of Biological Chemists, Inc., USA.

Deutsch C, Price M. Role Of Extracellular Na And K In Lymphocyte Activation, Journal of Cellular Physiology, Oct. 1982, pp. 73-79, vol. 113, No. 1, Alan R. Liss, Inc.

Saqr HE, Guan Z, Yates AJ, Stokes BT. Mechanisms Through Which PDGF Alters Intracellular Calcium Levels In U- 1242 MG Human Glioma Cells, Neurochemistry International, Dec. 1999, pp. 411-422, vol. 35, No. 6, Elsevier Science Ltd.

Chen CF, Corbley MJ, Roberts TM, Hess P. Voltage-Sensitive Calcium Channels In Normal And Transformed 3T3 Fibroblasts, Science, Feb. 1988, pp. 1024-1026, vol. 239, No. 4843.

Owen NE, Villereal ML. Role Of Ca2+ In Serum-Stimulated Na+ Influx In Normal And Transformed Cells, American Journal of Physiology, Mar. 1985, pp. C288-C295, vol. 248, No. 3 Pt 1, The American Physiological Society.

Macara IG. Oncogenes, ions, And Phospholipids, American Journal of Physiology, Jan. 1985, pp. C3-11, vol. 248, No. 1 Pt 1, The American Physiological Society.

Cameron IL, Smith NK, Pool TB, Sparks RL. Intracellular Concentration Of Sodium And Other Elements As Related To Mitogenesis And Oncogenesis In Vivo, Cancer Research, May 1980, pp. 1493-1500, vol. 40, No. 5.

Goller DA, Weidema WF, Davies RJ. Transmural Electrical Potential Difference As An Early Marker In Colon Cancer. Archives of Surgery, Mar. 1986, pp. 345-350, vol. 121, No. 3, The American Medical Association, USA.

Davies RJ, Weidema WF, Sandle GI, Palmer L, Deschner EE, Decosse JJ. Sodium Transport In A Mouse Model Of Colonic Carcinogenesis, Cancer Research, Sep. 1987, pp. 4646-4650, vol. 47, No. 17.

Davies RJ, Juncosa RD, Kaplan D, Pempinello C, Asbun H, Pilch YH. Colonic Epithelial Impedance Analysis In A Murine Model Of Large-Bowel Cancer, Archives of Surgery, Nov. 1986, pp. 1253-1258, vol. 121, No. 11, The American Medical Association, USA.

Davies RJ, Joseph R, Kaplan D, Juncosa RD, Pempinello C, Asbun H et al. Epithelial Impedance Analysis In Experimentally Induced Colon Cancer, Biophysical Journal, Nov. 1987, pp. 783-790, vol. 52, No. 5, The Biophysical Society by The Rockefeller University Press, USA.

Davies RJ, Joseph R, Asbun H, Sedwitz M. Detection Of The Cancer-Prone Colon, Using Transepithelial Impedance Analysis, Archives of Surgery, Apr. 1989, pp. 480-484, vol. 124, No. 4, The American Medical Association, USA.

Schaefer H, Schanne O. Membranpotentiale Von Einzelzellen in Gewebekulturen, Naturwissenschaften 1956, p. 445, vol. 43, Springer-Verlag.

Tokuoka S, Morioka H. The Membrane Potential of the Human Cancer and Related Cells, "GANN" The Japanese Journal of Cancer Research, Gann, 1957, pp. 353-354, vol. 48, The Japanese Cancer Association and the Japanese Foundation for Cancer Research, Nishi-Sugamo, Toshima-ku, Tokyo, Japan.

Balitsky KP, Shuba EP. Resting Potential of Malignant Cells, ACTA, Eighth International Cancer Congress, 1964, pp. 1391-1393, vol. 20, No. 67.

Cone CD, Jr. Unified Theory On The Basic Mechanism Of Normal Mitotic Control And Oncogenesis, Journal of Theoretical Biology, Jan. 1971, pp. 151-181, vol. 30, No. 1, Academic Press.

Cone CD, Jr., Cone CM. Induction Of Mitosis In Mature Neurons In Central Nervous System By Sustained Depolarization, Science, Apr. 1976, pp. 155-158, vol. 192, No. 4235.

Cone CD, Jr. The Role Of The Surface Electrical Transmembrane Potential In Normal And Malignant Mitogenesis, Annals of the New York Academy of Sciences, 1974, pp. 420-435, vol. 238, The New York Academy of Sciences, USA.

Lai CN, Gallick GE, Arlinghaus RB, Becker FF. Temperature-Dependent Transmembrane Potential Changes In Cells Infected With A Temperature-Sensitive Moloney Sarcoma Virus, Journal of Cellular Physiology, Oct. 1984, pp. 139-142, vol. 121, No. 1, Alan R. Liss, Inc.

Binggeli R, Cameron IL. Cellular Potentials Of Normal And Cancerous Fibroblasts And Hepatocytes, Cancer Research, Jun. 1980, pp. 1830-1835, vol. 40, No. 6.

Koch KS, Leffert HL. Growth Control Of Differentiated Adult Rat Hepatocytes In Primary Culture, Annals of The New York Academy of Sciences, 1980, pp. 111-127, vol. 349, the New York Academy of Sciences, New York, USA.

Funkhouser WK, Pilch YH, Davies RJ. The Electrophysiologic Changes Associated with Premalignancy in Colon Carcinogenesis, Federation Proceedings, Mar. 1986, p. 742, vol. 45, No. 4, Federation of American Societies for Experimental Biology.

Huang Y, Rane SG. Single Channel Study Of A Ca(2+)-Activated K+ Current Associated With Ras-Induced Cell Transformation, The Journal of Physiological Society, 1993, pp. 601-618, vol. 461, Cambridge University Press.

Davies RJ, Weiss A, Capko D, Brenner BM. Cell Membrane Potential in Benign and Malignant Breast Epithelial Cells. Breast Cancer Research and Treatment, 1996, p. 331, vol. 41, No. 3 Ref Type: Abstract, Kluwer Academic Publishers.

Schultz SG. Basic Principles of Membrane Transport, 1 ed. 1980, Cambridge University Press, London and New York.

Nagy IZ, Lustyik G, Nagy VZ, Zarandi B, Bertoni-Freddari C. Intracellular Na+:K+ Ratios In Human Cancer Cells As Revealed By Energy Dispersive X-Ray Microanalysis, The Journal of Cell Biology, Sep. 1981, pp. 769-777, vol. 90, No. 3, The Rockefeller University Press, USA.

Bustin SA, Li SR, Dorudi S. Expression of the Ca2+-Activated Chloride Channel Genes CLCA1 and CLCA2 Is Downregulated In Human Colorectal Cancer, DNA and Cell Biology, Nov. 2001, pp. 331-338, vol. 20, No. 6, Mary Ann Liebert, Inc., London, U.K.

Broaddus RR, Wargovich MJ, Castro GA. Early stages of 1,2-dimethylhydrazine-Induced Colon Carcinogenesis Suppress Immune-Regulated Ion Transport Of Mouse Distal Colon, Cancer Research, Nov. 1994, pp. 5930-5936, vol. 54, No. 22, Official Journal of the American Association For Cancer Research, USA.

Morris AP, Cunningham SA, Benos DJ, Frizzell RA. Cellular Differentiation Is Required For cAMP But Not Ca(2+)-dependent CI-Secretion In Colonic Epithelial Cells Expressing High Levels Of Cystic Fibrosis Transmembrane Conductance Regulator, The Journal of Biological Chemistry, Mar. 1992, pp. 5575-5583, vol. 267, No. 8, The American Society for Biochemistry and Molecular Biology.

Champigny G, Verrier B, Lazdunski M. A Voltage, Calcium, And ATP Sensitive Non Selective Cation Channel In Human Colonic Tumor Cells, Biochemical and Biophysical Research Communications, May 1991, pp. 1196-1203, vol. 176, No. 3, Academic Press, Inc.

Yao X, Kwan HY. Activity Of Voltage-Gated K+ Channels Is Associated With Cell Proliferation And Ca2+ Influx In Carcinoma Cells Of Colon Cancer, Life Sciences Including Pharmacology Letters, May 1999, pp. 55-62, vol. 65, No. 1, Elsevier Science, Inc.

Wissenbach U, Niemeyer BA, Fixemer T, Schneidewind A, Trost C, Cavalie A et al. Expression of CaT-like, A Novel Calcium-Selective Channel, Correlates With The Malignancy Of Prostate Cancer, The Journal of Biological Chemistry, Jun. 2001, pp. 19461-19468, vol. 276, No. 22, The American Society for Biochemistry and Molecular Biology.

Niemeyer BA, Bergs C, Wissenbach U, Flockerzi V, Trost C. Competitive Regulation of CaT-Like Mediated Ca2+ Entry by Protein Kinase C and Calmodulin, Proceedings of the National Academy of Sciences of the United States of America, Mar. 2001, pp. 3600-3605, vol. 98, No. 6.

Laniado ME, Fraser SP, Djamgoz MB. Voltage-Gated K(+) Channel Activity In Human Prostate Cancer Cell Lines Of Markedly Different Metastatic Potential: Distinguishing Characteristics Of PC-3 and LNCaP cells, The Prostate, 2001, pp. 262-274, vol. 46, No. 4, Wiley-Liss, Inc.

Shuba YM, Prevarskaya N, Lemonnier L, Van Coppenolle F, Kostyuk PG, Mauroy B et al. Volume-Regulated Chloride Conductance In The LNCaP Human Prostate Cancer Cell Line, American Journal of Physiology Cell Physiology, Oct. 2000, pp. C1144-C1154, vol. 279, No. 4, The American Physiological Society.

Fraser SP, Grimes JA, Djamgoz MB. Effects Of Voltage-Gated Ion Channel Modulators On Rat Prostatic Cancer Cell Proliferation: Comparison Of Strongly And Weakly Metastatic Cell Lines, The Prostate, 2000, pp. 61-76, vol. 44, No. 1, Wiley-Liss, Inc.

Rane SG. The Growth Regulatory Fibroblast IK Channel Is The Prominent Electrophysiological Feature Of Rat Prostatic Cancer Cells, Biochemical and Biophysical Research Communications, Mar. 2000, pp. 457-463, vol. 269, No. 2, Academic Press.

Skryma R, Van Coppenolle F, Dufy-Barbe L, Dufy B, Prevarskaya N. Characterization of Ca(2+)-Inhibited Potassium Channels In The LNCaP Human Prostate Cancer Cell Line, Receptors and Channels, 1999, pp. 241-253, vol. 6, No. 4, Harwood Academic Publishers, Malaysia.

Diss JK, Stewart D, Fraser SP, Black JA, Dib-Hajj S, Waxman SG et al. Expression Of Skeletal Muscle-Type Voltage-Gated Na+ Channel In Rat And Human Prostate Cancer Cell Lines, FEBS Letters, May 1998, pp. 5-10, vol. 427, No. 1, Elsevier on Behalf of the Federation of European Biochemical Sciences.

Grimes JA, Djamgoz MB. Electrophysiological Characterization Of Voltage-Gated Na+ Current Expressed In The Highly Metastatic Mat-LyLu Cell Line Of Rat Prostate Cancer, Journal of Cellular Physiology, Apr. 1998, pp. 50-58, vol. 175, No. 1, Wiley-Liss, Inc.

Skryma RN, Prevarskaya NB, Dufy-Barbe L, Odessa MF, Audin J, Dufy B. Potassium conductance In The Androgen-Sensitive Prostate Cancer Cell Line, LNCaP: Involvement in Cell Proliferation, The Prostate, 1997, pp. 112-122, vol. 33, No. 2, Wiley-Liss, Inc.

Laniado ME, Lalani EN, Fraser SP, Grimes JA, Bhangal G, Djamgoz MB et al. Expression and Functional Analysis Of Voltage-Activated Na+ channels In Human Prostate Cancer Cell Lines And Their Contribution To Invasion In Vitro, The American Journal of Pathology, Apr. 1997, pp. 1213-1221, vol. 150, No. 4, American Society for Investigative Pathology.

Grimes JA, Fraser SP, Stephens GJ, Downing JE, Laniado ME, Foster CS et al. Differential Expression Of Voltage-Activated Na+ currents In Two Prostatic Tumour Cell Lines: Contribution To Invasiveness In Vitro, FEBS Letters, Aug. 1995, pp. 290-294, vol. 369, No. 2-3, Elsevier on Behalf of the Federation of European Biochemical Societies.

Wykoff CC, Beasley N, Watson PH, Campo L, Chia SK, English R et al. Expression Of The Hypoxia-Inducible And Tumor-Associated Carbonic Anhydrases In Ductal Carcinoma In Situ Of The Breast, The American Journal of Pathology, Mar. 2001, pp. 1011-1019, vol. 158, No. 3, American Society for Investigative Pathology.

Stemmer-Rachamimov AO, Wiederhold T, Nielsen GP, James M, Pinney-Michalowski D, Roy JE et al. NHE-RF, A Merlin-Interacting Protein, Is Primarily Expressed In Luminal Epithelia, Proliferative Endometrium, And Estrogen Receptor-Positive Breast Carcinomas, The American Journal of Pathology, Jan. 2001, pp. 57-62, vol. 158, No. 1, American Society for Investigative Pathology.

Klimatcheva E, Wonderlin WF. An ATP-Sensitive K(+) Current That Regulates Progression Through Early G1 Phase Of The Cell Cycle In MCF-7 Human Breast Cancer Cells, The Journal of Membrane Biology, Sep. 1999, pp. 35-46, vol. 171, No. 1, Spinger.

Liu MP, Handschumacher RE. Tamoxifen Induces Na+-Dependent Uridine Transport and Dome Formation in a Human Breast Tumor Cell Line, The Cancer Journal from Scientific American, Aug. 1995, pp. 210-214, vol. 1, No. 3.

Shen MR, Droogmans G, Eggermont J, Voets T, Ellory JC, Nilius B. Differential expression Of Volume-Regulated Anion Channels During Cell Cycle Progression Of Human Cervical Cancer Cells, The Journal of Physiology, Dec. 2000, pp. 385-394, vol. 529, Pt 2, The Physiological Society.

Shen MR, Chou CY, Ellory JC. Volume-Sensitive KCl cotransport Associated With Human Cervical Carcinogenesis, Pflügers Archibe European Journal of Physiology, Sep. 2000, pp. 751-760, vol. 440, No. 5, Springer.

Chou CY, Shen MR, Wu SN. Volume-sensitive Chloride Channels Associated With Human Cervical Carcinogenesis, Cancer Research, Dec. 1995, pp. 6077-6083, vol. 55, No. 24, Official Journal of the American Association for Cancer Research.

Allen DH, Lepple-Wienhues A, Cahalan MD. Ion Channel Phenotype Of Melanoma Cell Lines, The Journal of Membrane Biology, 1997, pp. 27-34, vol. 155, No. 1, Springer.

Nilius B, Wohlrab W. Potassium Channels And Regulation Of Proliferation Of Human Melanoma Cells, The Journal of Physiology, 1992, pp. 537-548, vol. 445, Cambridge University Press.

Nilius B, Bohm T, Wohlrab W. Properties Of A Potassium-Selective Ion Channel In Human Melanoma Cells, Pflügers Archive European Journal of Physiology, Nov. 1990, pp. 269-277, vol. 417, No. 3, Springer International.

Cartman ML, Morris JA, Huddart H, Staff WG. Electrolyte Homeostasis In Urothelial Neoplasia: The Effects Of Amiloride, British Journal of Urology, May 1995, pp. 599-603. vol. 75, No. 5, Blackwell Science, Ltd.

Chien JL, Warren JR. Free Calcium And Calmodulin Levels In Acinar Carcinoma And Normal Acinar Cells Of Rat Pancreas, International Journal of Pancreatology, Mar. 1988, pp. 113-127, vol. 3, No. 2-3, Elsevier.

Kim JA, Kang YS, Jung MW, Lee SH, Lee YS. Involvement of Ca2+ Influx In The Mechanism Of Tamoxifen-Induced Apoptosis In HepG2 Human Hepatoblastoma Cells, Cancer Letters, Dec. 1999, pp. 115-123, vol. 147, No. 1-2, Elsevier.

Gutierrez AA, Arias JM, Garcia L, Mas-Oliva J, Guerrero-Hernandez A. Activation of a Ca2+-Permeable Cation Channel By Two Different Inducers Of Apoptosis In A Human Prostatic Cancer Cell Line, The Journal of Physiology, May 1999, pp. 95-107, vol. 517, Pt 1, The Physiological Society.

Tapia-Vieyra JV, Mas-Oliva J. Apoptosis and Cell Death Channels In Prostate Cancer, Archives of Medical Research, 2001, pp. 175-185, vol. 32, No. 3, Elsevier Science, Inc.

Elble RC, Pauli BU. Tumor Suppression by a Proapoptotic Calcium-Activated Chloride Channel in Mammary Epithelium, The Journal of Biological Chemistry, Nov. 2001, pp. 40510-40517, vol. 276, No. 44, The American Society For Biochemistry and Molecular Biology.

Kim JA, Kang YS, Lee YS. Involvement of K(+)-Cl(−)-cotransport In The Apoptosis Induced By N- Ethylmaleimide In HepG2 Human Hepatoblastoma Cells, European Journal of Pharmacology, Apr. 2001, pp. 1-5, vol. 418, Nos. 1-2, Elsevier.

Loewenstein WR. Junctional Intercellular Communication And The Control Of Growth, Biochimica et Biophysica Acta , Feb. 1979, pp. 1-65, vol. 560, No. 1, Elsevier/North-Holland.

Loewenstein WR. Junctional Cell-To-Cell Communication And Growth Control, Annals of the New York Academy of Sciences, 1980, pp. 39-45, vol. 339, The New York Academy of Sciences, New York, USA.

Pauli BU, Weinstein RS. Structure of Gap Junctions In Cultures Of Normal And Neoplastic Bladder Epithelial Cells, Experientia, 1981, pp. 248-250, vol. 37, No. 3, Birkhaüser Verlag.

Slaughter DP, Southwick HW Smejkal W. "Field Cancerization" in Oral Squamous Epithelium: Clinical Implications of Multicentric Origin, Cancer, A Journal of American Cancer, Jul. 1953, pp. 963-968, vol. 6, No. 4, J.B. Lippincott Company, Philadelphia, PA, USA.

Bernstein JM, Gorfien J, Noble B, Yankaskas JR. Nasal polyposis: Immunohistochemistry And Bioelectrical Findings (A Hypothesis For The Development Of Nasal Polyps), The Journal of Allergy and Clinical Immunology, Feb. 1997, pp. 165-175, vol. 99, No. 2, Mosby.

Bernstein JM, Yankaskas JR. Increased Ion transport In Cultured Nasal Polyp Epithelial Cells, Archives of Otolaryngology of Head & Neck Surgery, Sep. 1994, pp. 993-996, vol. 120, No. 9, American Medical Association.

Marina AA, Iliev IG, Schwalke MA, Gonzalez E, Marler KC, Flanagan CA. Association Between Cell Membrane Potential And Breast Cancer, Tumour Biology, 1994, pp. 82-89, vol. 15, No. 2.

Morimoto T, Kinouchi Y, Iritani T, Kimura S, Konishi Y, Mitsuyama N. et al. Measurement Of The Electrical Bio-Impedance Of Breast Tumors, European Surgical Research, Apr. 1990, pp. 86-92, vol. 22, No. 2, S. Karger Medical and Scientific Publishers.

Thurnherr N, Deschner EE, Stonehill EH, Lipkin M. Induction of Adenocarcinomas Of The Colon In Mice By Weekly Injections Of 1,2-dimethylhydrazine, Cancer Research, May 1973, pp. 940-945, vol. 33, No. 5.

Hebestreit A, Kersting U, Basler B, Jeschke R, Hebestreit H. Exercise Inhibits Epithelial Sodium Channels In Patients With Cystic Fibrosis, American Journal of Respiratory and Critical Care Medicine, Jul. 2001, pp. 443-446, vol. 164, No. 3.

Orlando RC, Powell DW, Croom RD, Berschneider HM, Boucher RC, Knowles MR. Colonic and Esophageal Transepithelial Potential Difference In Cystic Fibrosis, Gastroenterology, Apr. 1989, pp. 1041-1048, vol. 96, No. 4, American Gastroenterological Association.

Hay JG, Geddes DM. Transepithelial Potential Difference In Cystic Fibrosis, The Journal of the British Thoracic Society, Jul. 1985, pp. 493-496, vol. 40, No. 7, British Medical Association, London, England.

Knowles M, Gatzy J, Boucher R. Increased Bioelectric Potential Difference Across Respiratory Epithelia In Cystic Fibrosis, New England Journal of Medicine, Dec. 1981, pp. 1489-1495, vol. 305, No. 25, Massachusets Medical Society.

Oksiejczuk E, Figaszewski Z. Electrokinetic Potential Of Lung Cancer Cells, Rocziniki Akademii Medycznej Bialymstoku, 1997, pp. 340-354, vol. 42, Supplement 1.

Marina AA, Morris DM, Schwalke MA, Iliev IG, Rogers S. Electrical Potential Measurements In Human Breast Cancer And Benign Lesions, Tumour Biology, Jan. 1994, pp. 147-152, vol. 15, No. 3, S. Karger.

Broggi G, Franzini A. Value of Serial Stereotactic Biopsies And Impedance Monitoring In The Treatment Of Deep Brain Tumours, Journal of Neurology Neurosurgery and Psychiatry, May 1981, pp. 397-401, vol. 44, No. 5, British Medical Association, London, England.

Fukuda M, Shimizu K, Okamoto N, Arimura T, Ohta T, Yamaguchi S et al. Prospective Evaluation Of Skin Surface Electropotentials In Japanese Patients With Suspicious Breast Lesions, Japanese Journal of Cancer Research, Oct. 1996, pp. 1092-1096, vol. 87, No. 10, Elsevier Science, Ltd., Ireland and Business Center for Academic Societies, Japan.

Chauveau N, Hamzaoui L, Rochaix P, Rigaud B, Voigt JJ, Morucci JP. Ex Vivo Discrimination Between Normal And Pathological Tissues In Human Breast Surgical Biopsies Using Bioimpedance Spectroscopy, Annals of the New York Academy of Sciences, 1999, pp. 42-50, vol. 873, The New York Academy of Science, New York, NY, USA.

dA Silva JE, De Sa JP, Jossinet J. Classification Of Breast Tissue By Electrical Impedance Spectroscopy, Medical and Biological Engineering & Computing, Jan. 2000, pp. 26-30, vol. 38, No. 1.

Jossinet J. Variability Of Impedivity In Normal And Pathological Breast Tissue, Medical & Biological Engineering & Computing, Sep. 1996, pp. 246-350, vol. 34, No. 5.

Jossinet J. The Impedivity Of Freshly Excised Human Breast Tissue, Physiological Measurement, Feb. 1998, pp. 61-75, vol. 19, No. 1, Institute of Physics Publishing.

Jossinet J, Schmitt M. A Review Of Parameters For The Bioelectrical Characterization Of Breast Tissue, Annals of the New York Academy of Sciences, 1999, pp. 30-41, vol. 873, The New York Academy of Sciences, New York, NY.

Brown BH, Tidy JA, Boston K, Blackett AD, Smallwood RH, Sharp F. Relation Between Tissue Structure And Imposed Electrical Current Flow In Cervical Neoplasia, The Lancet, Mar. 2000, pp. 892-895, vol. 355, No. 9207, The Lancet Publishing Group, Ltd., Elsevier Sciences Ltd.

Cherepenin V, Karpov A, Korjenevsky A, Kornienko V, Mazaletskaya A, Mazourov D et al. A 3D Electrical Impedance Tomography (EIT) System For Breast Cancer Detection, Physiological Measurement, Feb. 2001, pp. 9-18, vol. 22, No. 1, Institute of Physics Publishing.

Gonzalez-Correa CA, Brown B, Smallwood RH, Kalia N, Stoddard CJ, Stephenson TJ et al. Virtual Biopsies In Barrett's Esophagus Using An Impedance Probe, Annals of New York Academy of Sciences, 1999, pp. 313-321, vol. 873, The New York Academy of Sciences, New York, NY, USA.

Gonzalez-Correa CA, Brown BH, Smallwood RH, Kalia N, Stoddard CJ, Stephenson TJ et al. Assessing The Conditions For In Vivo Electrical Virtual Biopsies In Barrett's Oesophagus, Medical & Biological Engineering & Computing, Jul. 2000, pp. 373-376, vol. 38, No. 4.

Gorecki J, Dolan EJ, Tasker RR, Kucharczyk W. Correlation of CT and MR With Impedance Monitoring And Histopathology In Stereotactic Biopsies, The Canadian Journal of Neurological Sciences, May 1990, pp. 184-189, vol. 17, No. 2.

Kimura S, Morimoto T, Uyama T, Monden Y, Kinouchi Y, Iritani T. Application of Electrical Impedance Analysis For Diagnosis Of A Pulmonary Mass, Chest, 1994, pp. 1679-1682, vol. 105, No. 6, Official Publication of American College of Chest Physicians.

Malich A, Fritsch T, Anderson R, Boehm T, Freesmeyer MG, Fleck M et al. Electrical Impedance Scanning For Classifying Suspicious Breast Lesions: First Results, European Radiology, 2000, pp. 1555-1561, vol. 10, No. 10, Springer-Verlag.

Malich A, Boehm T, Facius M, Freesmeyer MG, Fleck M, Anderson R et al. Differentiation of Mammographically Suspicious Lesions: Evaluation Of Breast Ultrasound, MRI Mammography And Electrical Impedance Scanning As Adjunctive Technologies In Breast Cancer Detection, Clinical Radiology, Apr. 2001, pp. 278-283, vol. 56, No. 4, WB Saunders Company LTD.

Malich A, Fritsch T, Mauch C, Boehm T, Freesmeyer M, Fleck M et al. Electrical impedance Scanning: A New Technique In The Diagnosis Of Lymph Nodes In Which Malignancy Is Suspected On Ultrasound, British Journal of Radiology, 2001, pp. 42-47, vol. 74, No. 877.

Morimoto T, Kimura S, Konishi Y, Komaki K, Uyama T, Monden Y et al. A Study Of The Electrical Bio-Impedance Of Tumors, Journal of Investigative Surgeries, 1993, pp. 25-32, vol. 6, No. 1, Taylor & Francis, New York, USA.

Ohmine Y, Morimoto T, Kinouchi Y, Iritani T, Takeuchi M, Monden Y. Noninvasive Measurement Of The Electrical Bioimpedance Of Breast Tumors, Anticancer Research, Jun. 2000, pp. 1941-1946, vol. 20, No. 3B.

Piperno G, Frei EH, Moshitzky M. Breast Cancer Screening By Impedance Measurements, Frontiers in Medical and Biological Engineering, 1990, pp. 111-117, vol. 2, No. 2.

Poupa V, Setka J, Vrana J. [Diagnosis of Malignant Diseases Of The Mucosa Of The Gastrointestinal Tract By Impedance Measurement Using The DIACA Apparatus], Rozhledy Chirurgii, 1986, pp. 316-321, vol. 65, No. 5.

Setka J, Vrana J. [Impedance of The Recto-Sigmoidal Mucosa Measured By Endoscopy In The Diagnosis Of Rectal Neoplasms], Archives Francaises des Maladies de L'Appareil Digestif, 1969, pp. 477-482, vol. 58, No. 7, Masson & Cie, Paris, France.

Setka J, Vrana J. [Impedance In The Endoscopy Of Rectal Neoplasms], Sb Ornik Lekarsky, 1970, pp. 89-93, vol. 72, No. 4.

Brown BH. Impedance Tomography and Spectroscopy: What can and what will we see? In: Sverre Grimnes, Ørjan G.Martinsen, Heidi Bruvoll, editors. Proceedings XI International Conference on Electrical Bio-Impedance. Oslo, Norway, University of Oslo, 2001: 9-13.

Thompson SM, Suzuki Y, Schultz SG. The Electrophysiology Of Rabbit Descending Colon. I. Instantaneous Transepithelial Current-Voltage Relations And The Current-Voltage Relations Of The Na-Entry Mechanism, Journal of Membrane Biology, 1982, pp. 41-45, vol. 66, No. 1, Springer-Verlag, New York New York, USA.

Brasitus TA, Dudeja PK, Foster ES. 1,2-Dimethylhydrazine-induced Alterations in Na+-H+ Exchange In Rat Colonic Brush-Border Membrane Vesicles, Biochimica et Biophysica Acta, Mar. 1988, pp. 483-488, vol. 938, No. 3, Elsevier.

Davies RJ, Asbun H, Thompson SM, Goller DA, Sandle GI. Uncoupling of Sodium Chloride Transport In Premalignant Mouse Colon, Gastroenterology, Jun. 1990, pp. 1502-1508, vol. 98, No. 6, American Gastroenterological Association.

Fraser GM, Portnoy M, Bleich M, Ecke D, Niv Y, Greger R et al. Characterization Of Sodium And Chloride Conductances In Preneoplastic And Neoplastic Murine Colonocytes, Pflugers Archive European Journal of Physiology, Nov. 1997, pp. 801-808, vol. 434, No. 6, Springer.

Schwan, H.P., Electrical Properties of Tissue and Cell Suspensions In: "Advances In Biological and Medical Physics," J.H. Lawrence and C.A. Tobias, Eds. vol. V, 1957, p. 147, Aladdin Press, Inc., New York.

Foster, Kenneth R., Bioimpedance as Medical Technology: What Does it Take to Succeed; University of Pennsylvania, Philadelphia, PA.

Farinha, BS, et al., Skin Impedance Reduction for Electrophysiology Measurements Using Ultrasonic Skin Permeation, Biomedical Instrumentation & Technology, Jan./Feb. 2006, pp. 72-77.

Hope et al., Technology review: The use of electrical impedance scanning in the detection of breast cancer, Breast Cancer Res 2004, 6:69-74.

Partial European Search Report, EP 03731268, dated Feb. 24, 2009.

Thielecke Hagen et al: Biohybrid microarrays: Impedimetric biosensors with 3D in vitro tissues for toxicological and biomedical screening Fresenius Journal of Analytical Chemistry, vol. 369, No. 1, Jan. 2001 (2001-01), pp. 23-29, XP002516085 ISSN: 0937-0633.

Ouadid-Ahidouch H, Roudbaraki M, Delcourt P, et.al. Am. J Physiol. Cell Physiol. Jul. 2004;287(1):C125-34.

Davies, R.J., Quinn, D.A., Davisson T.H. Breast Cancer Res. and Treat.vol. 88, (Suppl. 1) S221: 6005, 2004.

Davies, R.J., Quinn, D.A., Davisson T.H. Breast Cancer Res. and Treat.vol. 88, (Suppl. 1) S222-3: 6009, 2004.

Webster, M.A., Cardiff, R.D., and Muller, W.J. Proc. Natl. Acad. Sci. U.S.A. 1995 92:7849-7853.

Jhappan, C., Geiser, A.G., Kordon, E.C., Bagheri, D., Hennighausen, L., Roberts, A.B., Smith, G.H., and Merlino, G. EMBO J. 1993 12:1835-1845. [6] Stojadinovic A, Nissan A, Gallimidi Z, et.al. J Clin Oncol Apr. 20, 2005; 23 (12):2703-15.

Stojadinovic A, Nissan A, Gallimidi Z, et.al. J Clin Oncol Apr. 20, 2005; 23(12):2703-15.

\* cited by examiner

Impedance Profiles Normal, Benign, & Malignant Breast

FIG. 16
BODE PLOT
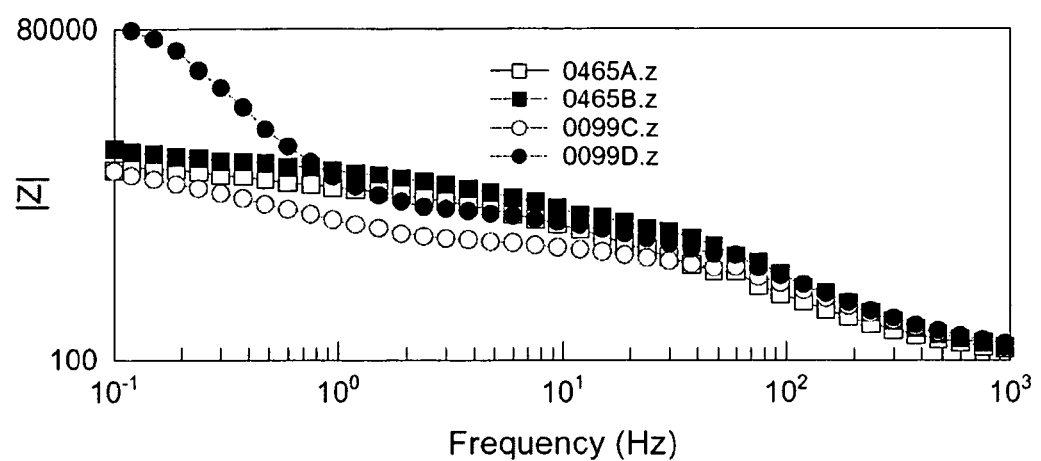
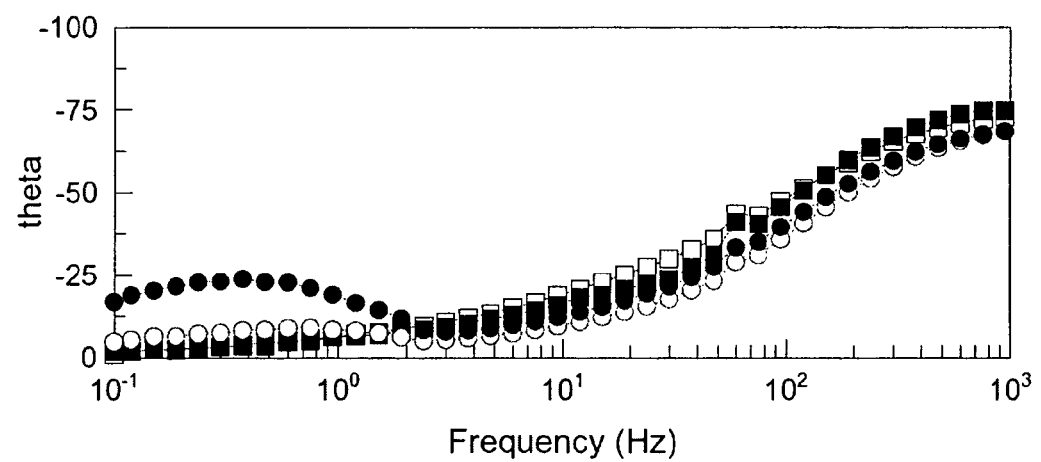

Effects of Suction Pressures on Normal Breast

Effects of Suction Pressures on Malignant Breast

Impedance Estimation Method

Applied to Data of Figure 20

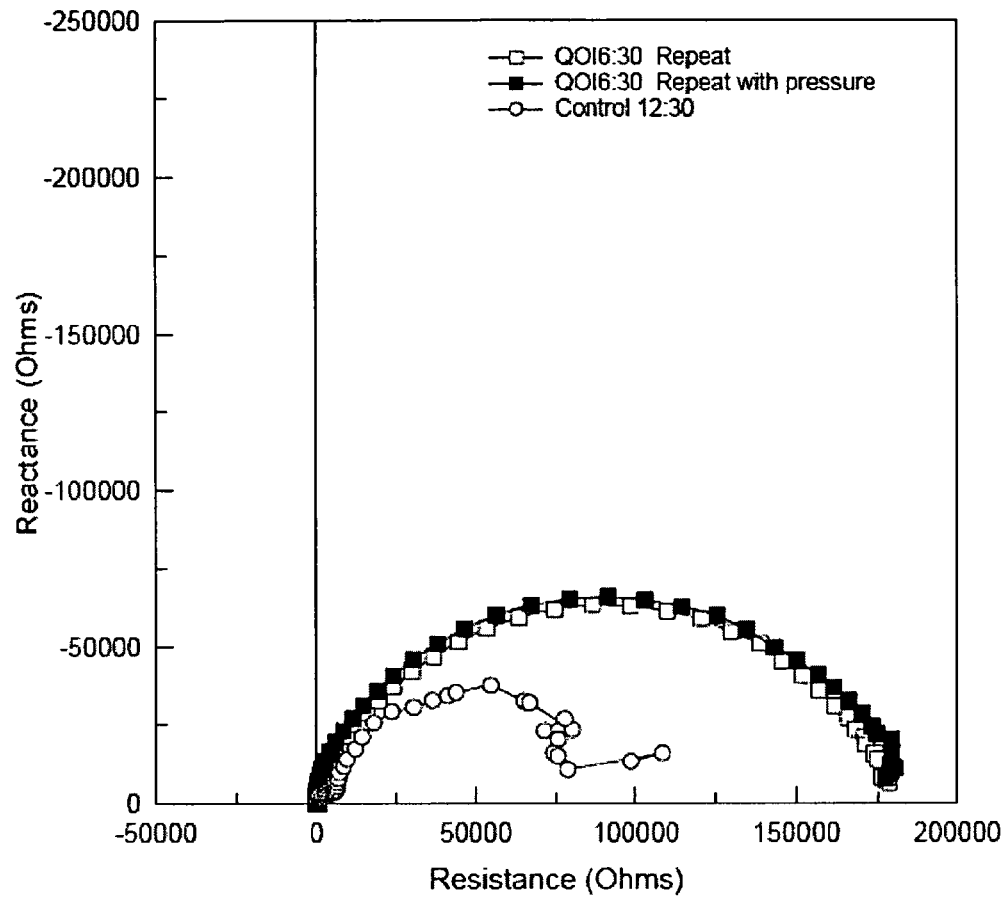

METHOD AND SYSTEM FOR DETECTING ELECTROPHYSIOLOGICAL CHANGES IN PRE-CANCEROUS AND CANCEROUS TISSUE AND EPITHELIUM

CROSS-REFERENCE TO RELATED APPLICATIONS

This application claims the benefit of the filing date of U.S. Provisional Patent Application No. 60/673,448 filed Apr. 21, 2005, the disclosure of which is hereby incorporated herein by reference.

BACKGROUND OF THE INVENTION

The present invention relates generally to the detection of abnormal or cancerous tissue, and more particularly, to the detection of changes in the electrophysiological characteristics of abnormal or cancerous tissue and to changes in those electrophysiological characteristics related to the functional, structural and topographic (the interaction of shape, position and function) relationships of the tissue during the development of malignancy. These measurements are made in the absence and presence of pharmacological and hormonal agents to reveal and accentuate the electrophysiological characteristics of abnormal or cancerous tissue.

Cancer is a leading cause of death in both men and women in the United States. Difficulty in detecting abnormal pre-cancerous or cancerous tissue before treatment options become non-viable is one of the reasons for the high mortality rate. Detecting of the presence of abnormal or cancerous tissues is difficult, in part, because such tissues are largely located deep within the body, thus requiring expensive, complex, invasive, and/or uncomfortable procedures. For this reason, the use of detection procedures is often restricted until a patient is experiencing symptoms related to the abnormal tissue. Many forms of cancers or tumors, however, require extended periods of time to attain a detectable size (and thus to produce significant symptoms or signs in the patient). It is often too late for effective treatment by the time the detection is performed with currently available diagnostic modalities.

Breast cancer is the most common malignancy affecting women in the Western World. The reduction in mortality for this common disease depends on early detection. The mainstay of early detection are X-ray mammography and clinical breast examination. Both are fraught with problems of inaccuracy. For example, mammography has a lower sensitivity in women with dense breasts, and is unable to discriminate between morphologically similar benign or malignant breast lesions.

Clinical breast examinations are limited because lesions less than one cm are usually undetectable and larger lesions may be obscured by diffuse nodularity, fibrocystic change, or may be too deep in the breast to enable clinical detection. Patients with positive mammographic or equivocal clinical findings often require biopsy to make a definitive diagnosis. Moreover, biopsies may be negative for malignancy in up to 80% of patients.

Accordingly, mammography and clinical breast examination have relatively poor specificity in diagnosing breast cancer. Therefore many positive mammographic findings or lesions detected on clinical breast examination ultimately prove to be false positives resulting in physical and emotional trauma for patients. Improved methods and technologies to identify patients who need to undergo biopsy would reduce healthcare costs and avoid unnecessary diagnostic biopsies.

Other technologies have been introduced in an attempt to improve on the diagnostic accuracy attainable with mammography and clinical breast examination alone. Breast ultrasound is helpful in distinguishing between cystic or solid breast lesions and may be useful in guiding needle or open biopsies. However, such techniques are unable to determine whether a solid mass, or calcifications are benign or malignant. Magnetic resonance imaging has been introduced in an attempt to improve on the accuracy of mammography. Its high cost and low specificity limit its general applicability for diagnosing and screening for breast cancer. Nuclear imaging with Positron Emission Tomogaphy (PET) has a lower sensitivity for small lesions, but is limited by cost.

It is also desirable to develop improved technology suitable for diagnosing pre-cancerous tissue and cancer in other tissue types and elsewhere in the body, particularly methods and devices suitable for ascertaining the condition of bodily ductal structures, e.g., the prostate, pancreas, etc., as well as the breast.

One proposed method for early detection of cancerous and pre-cancerous tissue includes measuring of the electrical impedance of biological tissue. For example, U.S. Pat. No. 3,949,736 discloses a low-level electric current passed through tissue, with a measurement of the voltage drop across the tissue providing an indirect indication of the overall tissue impedance. This method teaches that a change in impedance of the tissue is associated with an abnormal condition of the cells composing the tissue, indicating a tumor, carcinoma, or other abnormal biological condition. This disclosure, however, does not discuss either an increase or decrease in impedance associated with abnormal cells, nor does it specifically address tumor cells.

The disadvantage of this and similar systems is that the DC electrical properties of the epithelium are not considered. Most common malignancies develop in an epithelium (the cell layer that lines a hollow organ, such as the bowel, or ductal structures such as the breast or prostate), that maintains a transepithelial electropotential. Early in the malignant process the epithelium loses its transepithelial potential, particularly when compared to epithelium some distance away from the developing malignancy. The combination of transepithelial electropotential measurements with impedance are more accurate in diagnosing pre-cancerous and cancerous conditions.

Another disadvantage of the above referenced system is that the frequency range is not defined. Certain information is obtained about cells according to the range of frequencies selected. Different frequency bands may be associated with different structural or functional aspects of the tissue. See, for example, F. A. Duck, *Physical Properties of Tissues*, London: Academic Press, 2001; K. R. Foster, H. P. Schwan, *Dielectric properties of tissues and biological materials: a critical review*, Crit. Rev. Biomed. Eng., 1989, 17(1): 25-104. For example at high frequencies such as greater than about 1 GHz molecular structure has a dominating effect on the relaxation characteristics of the impedance profile. Relaxation characteristics include the delay in the response of a tissue to a change in the applied electric field. For example, an applied AC current results in voltage change across the tissue which will be delayed or phase shifted, because of the impedance characteristics of the tissue. Relaxation and dispersion characteristics of the tissue vary according to the frequency of the applied signal.

At lower frequencies, such as less than about 100 Hz, or the so called α-dispersion range, alterations in ion transport and charge accumulations at large cell membrane interfaces dominate the relaxation characteristics of the impedance profile. In the frequency range between a few kHz and about 1 MHz, or the so-called β-dispersion range, cell structure dominates the relaxation characteristics of the epithelial impedance profile. Within this range at low kHz frequencies, most of the applied current passes between the cells through the paracellular pathway and tight junctions. At higher, frequencies in the β-dispersion range the current can penetrate the cell membrane and therefore passes both between and through the cells, and the current density will depend on the composition and volume of the cytoplasm and cell nucleus. Characteristic alterations occur in the ion transport of an epithelium during the process of malignant transformation affecting the impedance characteristics of the epithelium measured at frequencies in the α-dispersion range. Later in the malignant process, structural alterations with opening of the tight junctions and decreasing resistance of the paracellular pathways, together with changes in the composition and volume of the cell cytoplasm and nucleus, affect the impedance measured in the β-dispersion range.

Another disadvantage with the above referenced system is that the topography of altered impedance is not examined. By spacing the measuring electrodes differently the epithelium can be probed to different depths. The depth that is measured by two surface electrodes is approximately half the distance between the electrodes. Therefore electrodes 1 mm apart will measure the impedance of the underlying epithelium to a depth of approximately 500 microns. It is known, for example, that the thickness of bowel epithelium increases at the edge of a developing tumor to 1356±208μ compared with 716±112μ in normal bowel. D. Kristt, et al. *Patterns of proliferative changes in crypts bordering colonic tumors: zonal histology and cell cycle marker expression. Pathol. Oncol. Res* 1999; 5(4): 297-303. Thickening of the ductal epithelium of the breast is also observed as ductal carcinoma in-situ develops. By comparing the measured impedance between electrodes spaced approximately 2.8 mm apart and compared with the impedance of electrodes spaced approximately 1.4 mm apart, information about the deeper and thickened epithelium may be obtained. See, for example, L. Emtestam & S. Ollmar. *Electrical impedance index in human skin: measurements after occlusion, in 5 anatomical regions and in mild irritant contact dermatitis. Contact Dermatitis* 1993; 28(2): 104-108.

Another disadvantage of the above referenced methods is that they do not probe the specific conductive pathways that are altered during the malignant process. For example, potassium conductance is reduced in the surface epithelium of the colon early in the malignant process. By using electrodes spaced less than 1 mm apart with varying concentrations of potassium chloride the potassium conductance and permeability may be estimated in the surface epithelium at a depth from less than 500μ to the surface.

A number of non-invasive impedance imaging techniques have been developed in an attempt to diagnose breast cancer. Electrical impedance tomography (EIT) is an impedance imaging technique that employs a large number of electrodes placed on the body surface. The impedance measurements obtained at each electrode are then processed by a computer to generate a 2 dimensional or 3 dimensional reconstructed tomographic image of the impedance and its distribution in 2 or 3 dimensions. This approach relies on the differences in conductivity and impedivity between different tissue types and relies on data acquisition and image reconstruction algorithms which are difficult to apply clinically.

The majority of EIT systems employ "current-driving mode," which applies a constant AC current between two or more current-passing electrodes, and measures the voltage drop between other voltage-sensing electrodes on the body surface. Another approach is to use a "voltage-driving approach," which applies a constant AC voltage between two or more current-passing electrodes, and then measures the current at other current-sensing electrodes. Different systems vary in the electrode configuration, current or voltage excitation mode, the excitation signal pattern, and AC frequency range employed.

Another disadvantage with using EIT to diagnose breast cancer is the inhomogeneity of breast tissue. The image reconstruction assumes that current passes homogeneously through the breast tissue which is unlikely given the varying electrical properties of different types of tissue comprising the breast. In addition image reconstruction depends upon the calculation of the voltage distribution on the surface of the breast from a known impedance distribution (the so called forward problem), and then estimating the impedance distribution within the breast from the measured voltage distribution measured with surface electrodes (the inverse problem). Reconstruction algorithms are frequently based on finite element modeling using Poisson's equation and with assumptions with regard to quasistatic conditions, because of the low frequencies used in most EIT systems.

Other patents, such as U.S. Pat. Nos. 4,955,383 and 5,099,844, disclose that surface electropotential measurements may be used to diagnose cancer. Empirical measurements, however, are difficult to interpret and use in diagnosis. For example, the above referenced inventions diagnose cancer by measuring voltage differences (differentials) between one region of the breast and another and then comparing them with measurements in the opposite breast. Changes in the measured surface potential may be related to differences in the impedance characteristics of the overlying skin. This fact is ignored by the above referenced and similar inventions, resulting in a diagnostic accuracy of 72% or less. J. Cuzick et al. *Electropotential measurements as a new diagnostic modality for breast cancer. Lancet* 1998; 352(9125): 359-363; M. Faupel et al. *Electropotential evaluation as a new technique for diagnosing breast lesions. Eur. J. Radiol.* 1997; 24 (1): 33-38. Neither AC impedance, or surface DC measurement approaches, measure the transepithelial breast DC potential or AC impedance characteristics of the breast epithelium.

Other inventions that use AC measurement, such as U.S. Pat. No. 6,308,097, also have a lower accuracy than may be possible with a combination of DC potential measurements and AC impedance measurements, that also measure the transepithelial electrical properties of mammary epithelium. Electrical impedance scanning (EIS) also known as electrical impedance mapping (EIM) avoids the limitations of complex image reconstruction encountered with EIT. The above referenced system diagnoses cancer by only measuring decreased impedance (increased conductance) and changes in capacitance over a cancer. It does not measure the mammary transepithelial impedance characteristics of the breast. There are several other limitations to this approach. Inaccuracies may occur because of air bubbles. Underlying bones, costal cartilages, muscle and skin may result in high conductance regions, which produce false positives. Depth of measurement is limited to 3-3.5 cm, which will result in false negatives for lesions on the chest wall. It is also not possible to localize lesions using this approach.

Another potential source of information for the detection of abnormal tissue is the measurement of transport alterations in the epithelium. Epithelial cells line the surfaces of the body and act as a barrier to isolate the body from the outside world. Not only do epithelial cells serve to insulate the body, but they also modify the body's environment by transporting salts, nutrients, and water across the cell barrier while maintaining their own cytoplasmic environment within fairly narrow limits. One mechanism by which the epithelial layer withstands the constant battering is by continuous proliferation and replacement of the barrier. This continued cell proliferation may partly explain why more than 80% of cancers are of epithelial cell origin. Moreover, given their special abilities to vectorially transport solutes from blood to outside and vice versa, it appears that a disease process involving altered growth regulation may have associated changes in transport properties of epithelia.

It is known that the addition of serum to quiescent fibroblasts results in rapid cell membrane depolarization. Cell membrane depolarization is an early event associated with cell division. Depolarization induced by growth factors appears biphasic in some instances but cell division may be stimulated without depolarization. Cell membrane depolarization is temporally associated with $Na^+$ influx, and the influx persists after repolarization has occurred. Although the initial $Na^+$ influx may result in depolarization, the increase in sodium transport does not cease once the cell membrane has been repolarized, possibly due to Na/K ATPase pump activation. Other studies also support the notion that $Na^+$ transport is altered during cell activation. In addition to altered $Na^+$-transport, $K^+$-, and $Cl^-$-transport is altered during cell proliferation.

A number of studies have demonstrated that proliferating cells are relatively depolarized when compared to those that are quiescent or non-dividing. Differentiation is associated with the expression of specific ion channels. Additional studies indicate that cell membrane depolarization occurs because of alterations in ionic fluxes, intracellular ionic composition and transport mechanisms that are associated with cell proliferation.

Intracellular $Ca^{2+}$ ($Ca^{2+}_i$) and pH ($pH_i$) are increased by mitogen activation. Cell proliferation may be initiated following the activation of phosphatidylinositol which releases two second messengers, 1,2-diacylglycerol and inosotol-1,4,5-triphosphate, which triggers $Ca^{2+}_i$ release from internal stores. $Ca^{2+}_i$ and $pH_i$ may then alter the gating of various ion channels in the cell membrane, which are responsible for maintaining the voltage of the cell membrane. Therefore, there is the potential for interaction between other intracellular messengers, ion transport mechanisms, and cell membrane potential. Most studies have been performed in transformed and cultured cells and not in intact epithelia during the development of cancer.

It was known for some time that cancer cells are relatively depolarized compared with non-transformed cells. It has been suggested that sustained cell membrane depolarization results in continuous cellular proliferation, and that malignant transformation results as a consequence of sustained depolarization and a failure of the cell to repolarize after cell division. C. D. Cone Jr., *Unified theory on the basic mechanism of normal mitotic control and oncogenesis. J. Theor. Biol.* 1971; 30(1): 151-181; C. D. Cone Jr., C. M. Cone. *Induction of mitosis in mature neurons in central nervous system by sustained depolarization. Science* 1976; 192(4235): 155-158; C. D. Cone, Jr. *The role of the surface electrical transmembrane potential in normal and malignant mitogenesis. Ann. N.Y. Acad. Sci.* 1974; 238: 420-435. A number of studies have demonstrated that cell membrane depolarization occurs during transformation and carcinogenesis. Other studies have demonstrated that a single ras-mutation may result in altered ion transport and cell membrane depolarization. Y. Huang, S. G. Rane, *Single channel study of a Ca(2+)-activated K+ current associated with ras induced cell transformation. J. Physiol.* 1993; 461: 601-618. For example, there is a progressive depolarization of the colonocyte cell membrane during 1,2 dimethylhydrazine (DMH)-induced colon cancer in $CF_1$ mice. The $V_A$ (apical membrane voltage) measured with intracellular microelectrodes in histologically "normal" colonic epithelium depolarized from −74.9 mV to −61.4 mV after 6 weeks of DMH treatment and to −34 mV by 20 weeks of treatment. The cell membrane potential in a benign human breast epithelial cell line (MCF-10A) was observed to be −50±4 mV (mean±SEM) and was significantly depolarized at −35±1 mV (p<0.002) in the same cell line after ras-transformation (the MCF-10AT cell line).

While epithelial cells normally maintain their intracellular sodium concentration within a narrow range, electronmicroprobe analysis suggests that cancer cells exhibit cytoplasmic sodium/potassium ratios that are three to five times greater than those found in their non-transformed counterparts. These observations partly explain the electrical depolarization observed in malignant or pre-malignant tissues, because of the loss of $K^+$ or $Na^+$ gradients across the cell membrane.

In addition to cell membrane depolarization, and altered intracellular ionic activity, other studies have shown that there may be a decrease in electrogenic sodium transport and activation of non-electrogenic transporters during the development of epithelial malignancies. These changes may affect or occur as a consequence of altered intracellular ionic composition.

In addition to cell membrane depolarization, and altered intracellular ionic activity, other studies have shown that there may be a decrease in electrogenic sodium transport and activation of non-electrogenic transporters during the development of epithelial malignancies. These changes may occur as a consequence of altered intracellular ionic composition. Other specific ion transport alterations have been described in colon, prostate, breast, uterine cervix, melanoma, urothelium, and pancreas during proliferation, differentiation, apoptosis, and carcinogenesis.

Apoptosis or physiological cell death is down-regulated during the development of malignancy. Ion transport mechanisms affected by apoptosis include the influx of $Ca^{2+}$ non-selective $Ca^{2+}$-permeable cation channels, calcium-activated chloride channels, and $K^+$—$Cl^-$ cotransport. J. A. Kim et al. *Involvement of Ca2+ influx in the mechanism of tamoxifen-induced apoptosis in Hep2G human hepatoblastoma cells. Cancer Lett.* 1999; 147(1-2): 115-123; A. A. Gutierrez et al. *Activation of a Ca2+-permeable cation channel by two different inducers of apoptosis in a human prostatic cancer cell line. J. Physiol.* 1999; 517 (Pt. 1): 95-107; J. V. Tapia-Vieyra, J. Mas-Oliva. *Apoptosis and cell death channels in prostate cancer. Arch. Med. Res.* 2001; 32(3): 175-185; R. C. Elble, B. U. Pauli. *Tumor Supression by a Proapoptotic Calcium-Activated Chloride Channel in Mammary Epithelium. J. Biol. Chem.* 2001; 276(44): 40510-40517.

Loss of cell-to-cell communication occurs during carcinogenesis. This results in defective electrical coupling between cells, which is mediated via ions and small molecules through gap junctions, which in turn influences the electrical properties of epithelia.

Epithelial cells are bound together by tight junctions, which consist of cell-to-cell adhesion molecules. These adhesion proteins regulate the paracellular transport of molecules and ions between cells and are dynamic structures that can tighten the epithelium, preventing the movement of substances, or loosen allowing substances to pass between cells. Tight junctions consist of integral membrane proteins, claudins, occludins and JAMs (junctional adhesion molecules). Tight junctions will open and close in response to intra and extracellular stimuli.

A number of substances will open or close tight junctions. The proinflammatory agent TGF-alpha, cytokines, IGF and VEGF opens tight junctions. Zonula occludens toxin, nitric oxide donors, and phorbol esters also reversibly open tight junctions. Other substances close tight junctions including calcium, H2 antagonists and retinoids. Various hormones such as prolactin and glucocorticoids will also regulate the tight junctions. Other substances added to drug formulations act as non-specific tight junction modulators including chitosan and wheat germ agglutinin.

The above referenced substances and others may act directly or indirectly on the tight junction proteins, which are altered during carcinogenesis. For example claudin-7 is lost in breast ductal epithelium during the development of breast cancer. The response of the tight junctions varies according to the malignant state of the epithelium and their constituent proteins. As a result the opening or closing of tight junctions is affected by the malignant state of the epithelium.

Polyps or overtly malignant lesions may develop in a background of disordered proliferation and altered transepithelial ion transport. Experimental animal studies of large bowel cancer have demonstrated that transepithelial depolarization is an early feature of the pre-malignant state. In nasal polyp studies, the lesions had a higher transepithelial potential, but these lesions were not pre-malignant in the same sense as an adenomatous or pre-malignant colonic polyp, that are usually depolarized. Electrical depolarization has been found in biopsies of malignant breast tissue. Recently alterations in impedance have been found to be associated with the pre-malignant or cancerous state in breast and bowel.

It has been discovered that transepithelial depolarization was a specific event associated with colonic carcinogenesis in $CF_1$ mice. The more susceptible site, the distal colon, underwent about a 30% decrease in transepithelial potential ($V_T$) after only four weeks of carcinogen treatment. This was before histological changes developed. A non-specific cytotoxic agent (5-fluorouracil), administered over the same period did not cause a reduction in $V_T$ in the same model. The reduction in $V_T$ was confirmed in a subsequent study where almost a 60% reduction was observed after carcinogen treatment. It has also been discovered that, although $V_T$ is invariably higher when measured in vivo, the "premalignant" colonic epithelium is usually depolarized when compared to normal colon.

DC electrical potential alterations have been used to diagnose non-malignant conditions such as cystic fibrosis, cancer in animal models, human cells or tissue and in man. Differences in impedance between normal tissue and cancer have been described in animal models in vitro human tissue in vitro and have been applied to in vivo cancer diagnosis.

DC potential measurements have not been combined with impedance measurements to diagnose cancer because the electrophysiological alterations that accompany the development of cancer have not been well understood or fully characterized. Surface measurements of potential or impedance are not the same as measurements performed across the breast epithelium, and described below, where electrical contact is made between the luminal surface of the duct and the overlying skin. Transepithelial depolarization is an early event during carcinogenesis, which may affect a significant region of the epithelium (a "field defect"). This depolarization is accompanied by functional changes in the epithelium including ion transport and impedance alterations. Early on in the process these take the form of increased impedance because of decreased specific electrogenic ion transport processes. As the tumor begins to develop in the pre-malignant epithelium, structural changes occur in the transformed cells such as a breakdown in tight junctions and nuclear atypia. The structural changes result in a marked reduction in the impedance of the tumor. The pattern and gradient of electrical changes in the epithelium permit the diagnosis of cancer from a combination of DC electrical and impedance measurements.

Another reason that DC electropotential and impedance measurements have not been successfully applied to cancer diagnosis is that transepithelial potential and impedance may be quite variable and are affected by the hydration state, dietary salt intake, diurnal or cyclical variation in hormonal level or non-specific inflammatory changes and other factors. In the absence of knowledge about the physiological variables which influence transepithelial potential and impedance these kind of measurement may not be completely reliable to diagnose pre-malignancy or cancer.

Furthermore, a detailed understanding of the functional and morphological alterations that occur during carcinogenesis permits appropriate electrical probing for a specifically identified ion transport change that is altered during cancer development. For example knowledge that electrogenic sodium absorption is altered during cancer development in breast epithelium permits the use of sodium channel blockers (amiloride) or varying sodium concentration in the ECM (electroconductive medium) to examine whether there is an inhibitable component of sodium conductance. By varying the depth of the measurement (by measuring the voltage drop across differently space electrodes), it is possible to obtain topographic and depth information about the cancerous changes in the epithelium. Using a combination of low and high frequency sine waves probing at different depths we are able to correlate the functional and morphological (structural) changes at different depths, with the impedance profile of the tissue.

The diagnostic accuracy of current technology using DC electropotentials or impedance alone have significant limitations. Sensitivity and specificity for DC electrical measurements in the breast have been reported as 90% and 55% respectively and 93% and 65% for impedance measurements. This would result in an overall diagnostic accuracy of between 72-79%, which is probably too low to result in widespread adoption. The measurement of ductal transepithelial DC potential, ductal transepithelial AC impedance spectroscopy alone, or the combination of DC electrical potentials and impedance spectroscopy will result in a diagnostic accuracy of greater than 90%, which will lead to improved clinical utility.

Breast cancer is thought to originate from epithelial cells in the terminal ductal lobular units (TDLUs) of mammary tissue. These cells proliferate and have a functional role in the absorption and secretion of various substances when quiescent and may produce milk when lactating. Functional alterations in breast epithelium have largely been ignored as a possible approach to breast cancer diagnosis. Breast epithelium is responsible for milk formation during lactation. Every month pre-menopausal breast epithelium undergoes a "rehearsal" for pregnancy with involution following menstruation. The flattened epithelium becomes more columnar as the epithelium enters the luteal phase from the follicular phase. In addition, duct branching and the number of acini reach a maximum during the latter half of the luteal phase. Just before menstruation apoptosis of the epithelium occurs and the process starts over again unless the woman becomes pregnant.

Early pregnancy and lactation may be protective against breast cancer because they result in a more differentiated breast epithelium which is less susceptible to carcinogenic influences whether estrogen or other environmental factors. It therefore seems that differentiated breast epithelium is less likely to undergo malignant change. Differentiated epithelium has a distinct apical and basolateral membrane domain to enable it to maintain vectorial transport function (the production of milk). In addition, differentiated cells maintain a higher cell membrane potential to transport various ions, lactulose and other substances in and out of the duct lumen. In contrast, more proliferative epithelial cells have depolarized cell membranes and are less able to maintain vectorial ion transport. Recently the epithelial $Na^+$ channel (ENaC) and the cystic fibrosis transmembrane conductance regulator (CFTR) have been identified in mammary epithelium and both localized on the apical, or luminal side, of the epithelium. These two transporters can be probed for by using amiloride, a blocker of the ENaC, or by opening up $Cl^-$ channels regulated by CFTR using-cAMP.

For example, 20 μM luminal amiloride depolarized the transepithelial potential from −5.9±0.5 mV (mean±SEM) by +3.1±0.5 mV. Forskolin (10M), which raises cAMP and opens $Cl^-$ channels via the CFTR hyperpolarized the breast epithelium by −2.2±0.1 mV. These changes were accompanied by an increase (17%) and subsequent decrease (19%) in transepithelial resistance respectively. In transformed breast epithelium the ENaC is down-regulated, whereas $Cl^-$ secretion may increase, similar to observations reported for carcinoma of the cervix. Non-lactating breast epithelium has relatively leaky tight junctions. This results in a paracellular shunt current, which hyperpolarizes the apical membrane of the epithelial cell. The larger the shunt current the more hyperpolarized the apical membrane and therefore the epithelium depolarizes since:

$$TEP=V_{BL}-V_A \text{ and } i=TEP/R_S; \text{ where}$$

TEP=Transepithelial potential;
$V_{BL}$=voltage of the basolateral membrane;
$V_A$=voltage of the apical membrane;
i=shunt current; and
$R_S$=paracellular (shunt) resistance.

Evidence that breast carcinogenesis may be associated with functional incompetence of breast epithelium also comes from a number of other sources. Some transgenic strains of mice have defective lactation. The transgenic src mouse which develops hyperplastic alveolar nodules, otherwise develops a normal mammary tree but has defective lactation. The notch4 and TGFβ transgenic mouse also demonstrate defective lactation. Cyclin D1 females have persistent lactation 6-9 months after weaning, and TGFα mice, which have a defect in apoptosis and fail to undergo epithelial regression develop hypersecretion. These data suggest that there is a relationship between epithelial function and genetic expression which affects proliferation and tumor development.

Breast cysts occur in 7% of the female population and are thought to develop in the TDLUs. Apocrine cysts have a higher potassium content than simple cysts. Apocrine cysts may be associated with the subsequent development of breast cancer. There may therefore be a fundamental change in the epithelium at risk for breast cancer development with a redistribution of electrolyte content across the cell membrane resulting in altered cyst electrolyte content and cell membrane depolarization. Although it is commonly known that during lactation the breast transports lactulose, proteins, fatty acids, immunoglobulins cholesterol, hormones, ions and water across the ductal and lobular epithelium and actively secretes milk, it is less widely appreciated that in the non-pregnant and non-lactating state the breast, throughout life exhibits excretory and absorptive function. The difference between the lactating and the non-lactating breast being of degree and the chemical constitution of the nipple duct fluid. Ductal secretions have been analyzed to diagnose biological conditions of the breast.

A number of approaches have been used to obtain ductal fluid, including a suction cup to obtained pooled secretions; nipple aspiration fluid (NAF), and more recently, cannulation of one of the 6-12 ducts that open onto the nipple surface. Substances and cells within the duct fluid may therefore be accessed to identify abnormalities that may be associated with the diseased state of the breast. One disadvantage of the above referenced approaches is the difficulty in obtaining adequate NAF or lavage fluid to perform analysis. Another disadvantage has been the inability to identify or cannulate the ducts where an abnormality in the fluid or cells may be identified.

Hung (U.S. Pat. No. 6,314,315) has suggested an electrical approach to identify ductal orifices on the nipple surface. In that disclosure it is taught that DC potential or impedance measurement may facilitate the identification of openings or orifices on the surface of the nipple. However, it is not taught that the characteristics of the DC electrical signal or impedance may characterize the condition of the breast. Moreover, it is not taught that breast transepithelial DC measurements, transepithelial AC impedance spectroscopy, alone or in combination may be used to diagnose breast cancer.

Ionic gradients exist between the fluid secretions within the breast ducts and the plasma. For example, it is known that the nipple aspirate fluid has a sodium concentration $[Na^+]$ of 123.6±33.8 mEq/l (mean±standard deviation) compared with a serum $[Na^+]$ of approximately 150 mEq/l (Petrakis1). Nulliparous women have NAF $[Na^+]$ that are approximately 10 mEq/l higher than parous women, but still significantly below serum levels. Similarly potassium concentration $[K^+]$ is significantly higher at 13.5±7.7 mEq/l in parous women and 12.9±6.0 mEq/l in nulliparous women compared with serum levels of $[K^+]$ of approximately 5.0 mEq/l. Other investigators have reported lower NAF $[Na^+]$ of 53.2 mEq/l suggesting that significant ionic gradients can be established between the plasma and duct lumen in non-lactating breast. In pregnancy these gradients are even higher for sodium with a $[Na^+]$ of 8.5±0.9 mEq/l reported in milk which is almost 20 fold lower than plasma. Chloride concentration $[Cl^-]$ in milk is almost one tenth of the concentration found in plasma with values of 11.9±0.5 mM reported. Although $[Na^+]$ and $[Cl^-]$ levels in ductal secretions rise and the $[K^+]$ falls following the cessation of lactation, significant ionic gradients are maintained between the duct lumen and plasma.

Furthermore, in women undergoing ovulatory cycles during lactation distinct changes have been observed in the ion and lactulose concentrations of breast milk. The first change occurs 5-6 days before ovulation and the second 6-7 days after ovulation. During these periods $[Na^+]$ and $[Cl^-]$ increased more than two-fold and $[K^+]$ decreased approximately 1.5-fold. It is unclear whether changes in estrogen or progesterone levels before and after ovulation are affecting the ion composition of milk. However, it is known that alterations in the ionic composition of milk influences the transepithelial electrical potential as measured in mammals.

Furthermore, it is known that various hormones affect breast epithelial ion transport. For example, prolactin decreases the permeability of the tight-junctions between breast epithelial cells, stimulates mucosal to serosal $Na^+$ flux, upregulates $Na^+:K^+:2Cl^-$ cotransport and increases the $[K^+]$ and decreases the $[Na^+]$ in milk. Glucocorticoids control the formation of tight-junctions increasing transepithelial resistance and decreasing epithelial permeability. Administration of cortisol into breast ducts late in pregnancy has been shown to increase the $[K^+]$ and decrease $[Na^+]$ of ductal secretions. Progesterone inhibits tight-junction closure during pregnancy and may be responsible for the fluctuations in ductal fluid electrolytes observed during menstrual cycle in non-pregnant women, and discussed above. Estrogen has been observed to increase cell membrane and transepithelial potential and may stimulate the opening of $K^+$-channels in breast epithelial cells. The hormones mentioned above vary diurnally and during menstrual cycle. It is likely that these variations influence the functional properties of breast epithelium altering the ionic concentrations within the lumen, the transepithelial potential and impedance properties, which are dependent upon the ion transport properties of epithelial cells and the transcellular and paracellular conductance pathways.

Accordingly, these variations can be used as diagnostic indicia of changes to breast tissue, which have to date yet to be exploited. Thus, there remains a need for effective and practical methods for detecting abnormal breast tissue as well as other epithelial and/or ductal tissue.

The disclosures of the following patent applications, each to Richard J. Davies, the inventor herein, are hereby incorporated by reference herein: U.S. patent application Ser. No. 10/151,233, filed May 20, 2002, entitled "Method and System for Detecting Electrophysiological Changes in Pre-Cancerous and Cancerous Tissue"; U.S. patent application Ser. No. 10/717,074, filed Nov. 19, 2003, entitled "Method And System For Detecting Electrophysiological Changes In Pre-Cancerous And Cancerous Breast Tissue And Epithelium"; and U.S. patent application Ser. No. 10/716,789, filed Nov. 19, 2003, entitled "Electrophysiological Approaches To Assess Resection and Tumor Ablation Margins and Responses To Drug Therapy".

SUMMARY OF THE INVENTION

One aspect of the invention provides a method for determining a condition of a region of epithelial tissue, for example epithelial breast tissue comprising: establishing a connection between a first electrode and the epithelial tissue of the nipple of a breast; placing a second electrode in contact with the surface of the breast; establishing a signal between the first and second electrodes; establishing that the nipple ducts of the breast are open; measuring between the first and second electrode (1) a DC potential; and (2) impedance at about 5 different frequencies in the range of about 10 Hz to about 200 Hz and impedance at from about 5 to about 50 different frequencies in the range of about 0.1 Hz to about 10 Hz; and determining the condition of the region of epithelial tissue based on the DC potential and impedance measurements between the first and second electrode.

In another aspect of the invention there is provided a method for determining a condition of a region of epithelial tissue, for example, epithelial breast tissue comprising: placing over the nipple of a breast a cup having an interior, and first and second openings, and an electrode disposed within the interior, the cup having a source of suction in communication with the first opening, the second opening having been placed over the nipple; establishing an electrical connection between the electrode and the epithelial lining of the mammary ducts, which are in continuity with the surface of the nipple of a breast through the duct openings (orifices); placing a second electrode in electrical contact with the surface of the breast; establishing a signal between the first and second electrodes; establishing that the nipple ducts of the breast are open; measuring a DC potential between the first and second electrode; applying suction to the cup sufficient to effect ductal collapse in a normal or non-malignant duct; and measuring impedance at about 5 different frequencies in the range of about. 10 Hz to about 200 Hz and impedance at from about 5 to about 50 different frequencies in the range of about 0.1 Hz to about 10 Hz; and altering the suction level and again measuring impedance at about 5 different frequencies of the range of about 10 Hz to about 200 Hz and impedance at from about 5 to about 50 different frequencies in the range of about 0.1 Hz to about 10 Hz; and determining the condition of the region of epithelial tissue within the ducts and lobules of the breast, based on the DC potential, and the impedance measurements under varying pressure conditions.

In yet another embodiment of the invention there is provided A method for determining a condition of a region of epithelial or stromal tissue comprising: A. measurement of an impedance spectrum over a region of tissue where an abnormality is suspected (suspicious region); B. measurement of an impedance spectrum over a region of tissue where no abnormality is suspected (control region); C. application of mechanical pressure or compression over the suspicious region; D. measurement of the impedance spectrum in the suspicious region following the application of mechanical pressure; E. application of mechanical pressure or compression over the control region; F. comparison of the impedance profile before and after compression in the suspicious region; G. comparison of the impedance profile before and after compression in the control region; and H. comparison of the impedance profile of the suspicious region to the control region.

BRIEF DESCRIPTION OF THE DRAWINGS

The accompanying drawings, which are incorporated in and constitute a part of this specification, illustrate one embodiment of the invention and together with the description, serve to explain the principles of the invention.

FIG. 16 illustrates a Bode plot of impedance data comparing patients with fibrocystic disease (0465) and breast cancer (0099).

FIG. 29 illustrates the impedance profile following compression of a more typical fibroadenoma in breast tissue.

DETAILED DESCRIPTION

Figure 1:
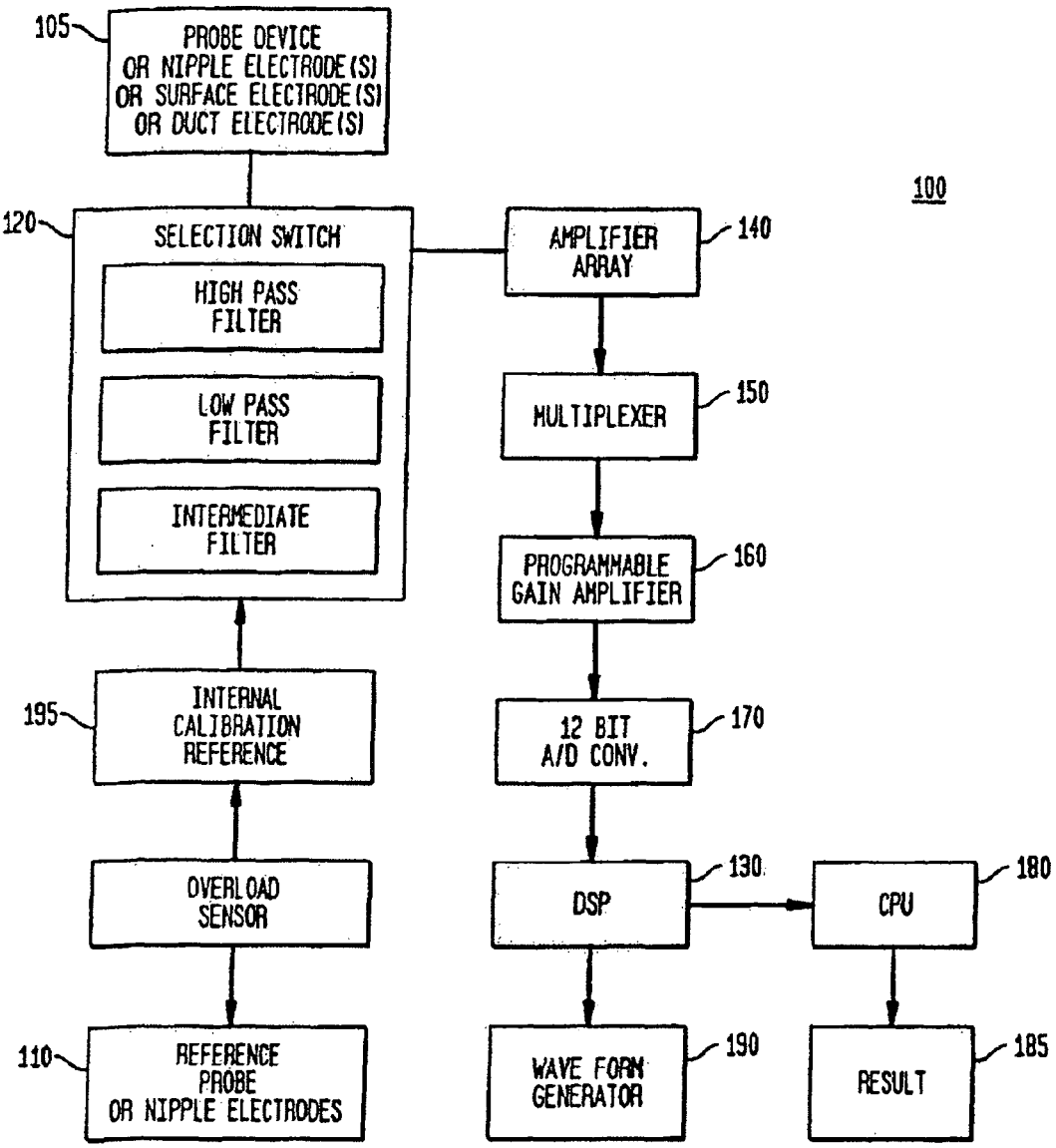
FIG. 1 is a schematic diagram of a DC and AC impedance measuring device, consistent with an embodiment of the present invention.

Reference will now be made in detail to an embodiment of the invention, an example of which is illustrated in the accompanying drawings. Wherever possible, the same reference numbers will be used throughout the drawings to refer to the same or like parts.

The present invention overcomes problems and inadequacies associated with prior methods used for characterizing abnormal or cancerous epithelial tissue. In summary, various embodiments of the present invention use DC and/or impedance measurements, under ambient and/or variable suction, that pass the current or signal across the breast epithelium and tumor using specially constructed electrodes. For example a nipple electrode may be used to measure the voltage and/or impedance between ductal epithelium, surrounding breast tissue, skin and surface or other electrode. The nipple electrode may also be used to pass the current along the ductal system of the breast. Another type of electrode may be used to measure the voltage and/or impedance signal, and/or pass a current and measure the signal at the individual ductal orifices at the nipple surface. Another type of electrode may be used to measure the voltage and/or impedance signal, and/or pass a current and measure the signal within individual ducts using a modified ductal probe or ductoscope which may have one or more electrodes attached to it. All of these electrodes may be used individually, in combination with one another, or with a surface probe or electrodes. Additionally DC and impedance measurements will be used in combination to more adequately characterize abnormal or cancerous tissues. DC measurements provide information about the functional state of the epithelium and can detect early pre-malignant changes and an adjacent malignancy. In particular, impedance measurements at several frequencies in specifically defined ranges using differently spaced electrodes provide depth and topographic information to give both structural (high frequency range) and functional (low frequency range) information about the tissue being probed. Abnormal or cancerous tissue can be detected and characterized by detecting and measuring transport alterations in epithelial tissues, using ionic substitutions and/or pharmacological and hormonal manipulations to determine the presence of abnormal precancerous or cancerous cells. A baseline level of transepithelial DC potential, impedance or other electrophysiological property that is sensitive to alterations in transport in epithelia is measured in the tissue to be evaluated. An agent may be introduced to enhance the transport or make it possible to detect the transport alteration. The transepithelial DC potential and/or impedance of the tissue (or other electrophysiological property that may reflect or make it possible to detect alterations in the transport) are then measured. Based on the agent introduced and the measured electrophysiological parameter, the condition of the tissue is determined.

A method and system are provided for determining a condition of a selected region of breast epithelial tissue. At least two current-passing electrodes are located in contact with a first surface of the selected region of the tissue. Alternatively the current passing electrodes may pass current across the tissue or epithelium as for example between the nipple ducts, ductal lumen, epithelium, breast parenchyma and surface of the breast. Alternatively, the ducts may be accessed by a central duct catheter or ductoscope. A plurality of measuring electrodes are located in contact with the first surface of the breast as well. Initially, one or more of the measuring electrodes is used to measure the DC potential referenced to another electrode, or reference point. A signal is established between the current-passing electrodes. Impedance, associated with the established signal, is measured by one or more of the measuring electrodes. Alternatively a three-electrode system may be used for measurements whereby one electrode is used for both current injection and voltage recording. An agent is introduced into the region of tissue. The condition of the tissue is determined based on the effect of the agent on measured DC transepithelial potential, impedance or other electrophysiological characteristic. The electrodes in the described methods and apparatus can be used in contact with, in proximity to, over, or inserted into the tissues being examined. It should be understood that where the method is described in an embodiment as encompassing one of these arrangements, it is contemplated that it can also be used interchangeably with the other. For example, where the method is described as having an electrode in contact with the tissue, the method can also be used with the electrode inserted into or in proximity to the tissue. Similarly, where the method is described as having an electrode in proximity to the tissue, it is contemplated that the electrode can also be in contact with or inserted into the tissue.

In order to more accurately detect transport alterations in abnormal pre-cancerous or cancerous epithelial tissue, a pharmacological agent may be introduced to manipulate the tissue. Pharmacological agents may include agonists of specific ion transport and electrical activity, antagonists of specific ion transport and electrical activity, ionic substitutions, and/or hormonal or growth factor stimulation or inhibition of electrical activity.

Depending on the location of the tissue to be investigated, a number of methods may be used to administer the pharmacological or hormonal agents. One exemplary method includes introducing the agent directly to the tissue being investigated, via ductal infusion, perfusion, direct contact or injection. Another exemplary method includes applying the agent to the skin surface, wherein the agent acts transcutaneously, or through the skin. Yet another exemplary method includes electroporation, wherein the ductal epithelium or surface is made permeable by the passage of alternating current via electrodes in contact or penetrating the organ or epithelium of interest. The agent then passive diffuses into the organ and its constituent cells. The agent may be introduced directly into the breast ductal system using the modified nipple aspirator cup and electrode, or lavaged into a specific duct using a ductal catheter or probe. Additional exemplary methods include via inhalation, oral administration, lavage, gavage, enema, parenteral injection into a vein or artery, sublingually or via the buccal mucosa, or via intraperitoneal administration. One skilled in the art will appreciate that other methods are possible and that the method chosen is determined by the tissue to be investigated.

Thus, systems and methods consistent with the present invention use transepithelial electropotential or/and impedance measurements to diagnose pre-malignancy or cancer. Further, systems and methods consistent with the present invention use a defined set of frequencies, in combination, to characterize functional and structural alterations in pre-malignancy and cancer. By using spaced electrodes the present invention may provide topographic and geometrical (depth) information about the epithelium under examination to diagnose pre-malignancy and cancer. In one embodiment, systems and methods of the present invention use electrodes with specially formulated ECMs to provide functional information about the epithelium to diagnose pre-malignancy and cancer.

In order to measure the transepithelial breast DC potential it is necessary that the lumen of the duct be electrically accessed by a nipple electrode constructed to make an electrical connection between the Ag/AgCl (or similar low offset platinum/hydrogen, titanium, tin-lead alloy, nickel, aluminum, zinc, carbon, or other conductive metal or conductive polymer electrode) pellet recessed within the nipple cup. The cup is filled with an ECM (electro-conductive medium), which enters the ductal system passively, or after aspiration with a syringe or pump, making contact with the ductal lumen. A surface electrode placed at the surface of the breast completes the electrical circuit, so that measurements of transepithelial potential may be made between the ductal epithelium, or center of the tumor and the skin surface. Similar considerations have to be given to measure transepithelial AC impedance whereby the measuring electrodes measure the voltage drop and phase shift across the ductal epithelium or tumor, by utilizing a nipple electrode in combination with a skin surface electrode. Other configurations of this approach are more invasive, whereby measurement can be made between an electrode inserted via a ductoscope or nipple duct probe electrode referenced to the skin or an IV (intravenous), intradermal, or subcutaneous electrode. In another embodiment, the duct may also be accessed by a needle-electrode inserted through the skin.

In order to combine DC transepithelial measurement with impedance measurements, it is necessary to obtain baseline measurement of the DC potential using the voltage sensing electrodes, referenced to surface electrode with low-contact impedance, or the blood stream via an IV, or the interstitial body fluid via a needle electrode or electrode that permeabilizes the overlying epidermis or other epithelium, or other body reference point. The electrodes may contain different ionic concentrations, pharmacological agents or hormones in their ECMs. As used in this description, an ECM is a medium that permits transmission of electrical signals between the surface being measured and the electrode. An agent includes any ionic concentration, pharmacological agent, hormone or other compound added to the ECM or otherwise introduced to the tissue under investigation, selected to provide further information about the condition of the tissue. In another embodiment the concentrations of agents may be changed using a flow through system.

Electroconductive media can include conductive fluids, creams or gels used with external or internal electrodes to reduce the impedance (resistance to alternating current) of the contact between the electrode surface and the skin or epithelial surface. In the case of DC electrodes it is also desirable that the ECM results in the lowest DC offset at the electrode surface, or an offset that can be measured. The ECM will often contain a hydrogel that will draw fluid and electrolytes from deeper layers of the skin to establish electrical contact with the surface electrode. Electrodes that are used to pass current require ECMs with high conductance. Usually this is accomplished by using ECMs with high electrolyte content. The electrolytes frequently used are KCl (potassium chloride) because of the similar ionic mobility of these two ions in free solution, so that electrode polarization is less of a problem than when ions of different mobility are used. Other ions such as sodium may be used in ECM formulations, and the higher electrolyte concentration result in more rapid electrode equilibration.

In situations where estimations will be made of the permeability of the epithelium to specific ions, the concentration of K in the ECM will be varied so that the conductance of the epithelium to potassium may be measured electrophysiologically. An enhancer or permeant may be added to the ECM to increase the conductance of the underlying skin to the electrolyte in the ECM. Other approaches include mild surface abrasion with pumice and alcohol to reduce surface skin resistance, abrasive pads such as Kendall Excel electrode release liner (Tyco Health Care, Mansfield, Mass.), 3M Red Dot Trace Prep (3M Corporation, St. Paul, Minn.), cleaning the skin with alcohol, an automated skin abrasion preparation device that spins a disposable electrode to abrade the skin (QuickPrep system, Quinton, Inc., Bothell, Wash.), ultrasound skin permeation technology (SonoPrep, Sontra Medical Corporation, Franklin, Mass.), or silicon electrodes, which just penetrate the stratum corneum to reduce skin surface resistance. (See also, the comparison and discussion of several methods in Biomedical Instrumentation & Technology, 2006; 39: 72-77; the content of which is incorporated herein by reference.)

In order to measure the depth of the impedance alteration, the voltage drop will be made between surface electrodes with different spacing. Spacing will be determined by knowledge of the depth to be probed. Similarly two different frequency ranges will be used to measure functional and structural changes at different depths.

In order to more accurately detect the functional transport alterations at different depths in abnormal pre-cancerous or cancerous epithelial tissue, a pharmacological agent is introduced to manipulate the tissue, while electrically probing the tissue at different frequencies and monitoring the voltage drop between differently spaced electrodes. Pharmacological agents include agonists of specific ion transport and electrical activity, antagonists of specific ion transport and electrical activity, ionic substitutions, and/or hormonal or growth factor stimulation or inhibition of electrical activity.

Depending on the location of the tissue to be investigated, a number of methods are used to administer the pharmacological or hormonal agents. One exemplary method includes introducing the agent directly to the tissue being investigated, via ductal perfusion, infusion, direct contact or injection. Another exemplary method includes applying the agent to the skin surface, wherein the agent acts transcutaneously, or through the skin. Yet another exemplary method includes electroporation, wherein the epithelium or surface is made permeable by the passage of alternating current via electrodes in contact or penetrating the surface of the breast or ductal epithelium of interest. The agent then passively diffuses into the breast and its constituent cells. Additional exemplary methods include via inhalation, oral administration, lavage, gavage, enema, parenteral injection into a vein or artery, sublingually or via the buccal mucosa, or via intraperitoneal administration. One skilled in the art will appreciate that other methods are possible and that the method chosen is determined by the tissue to be investigated.

Based on the agent introduced and the tissue being investigated, measurements of electrophysiological properties, such as impedance, are performed. Other properties that can be measured includes, transepithelial potential, changes in spontaneous oscillations in transepithelial potential or impedance associated with the malignant state, time delay in a propagation signal between electrodes, which indicates a loss of gap-junction function. If adjacent cells are electrically coupled, one can examine the loss of coupling by pharmacologically eliciting an electrical signal and measuring the signal propagation up and down-stream through surface epithelial cells. This is a functional measurement of the gap-junctions, whereas simple electrical stimulation will measure shunting of a current between the cells (a structural measurement, at least in the high frequency range).

The results of these measurements are then used to determine the condition of the investigated tissue. For example, research has indicated that specific ion transport processes are altered during the development of cancer. For example, a loss of electrogenic $Na^+$ transport, an up-regulation in Na/H exchange, a down-regulation in $K^+$ conductance, a decrease in basal $Cl^-$ absorption, and a down-regulation in c-AMP (cyclic adenosine-3',5'-cyclic monophosphate) stimulated $Cl^-$ secretion have been observed.

Thus, by administering agents appropriate to the particular epithelial tissue and measuring the associated electrophysiological characteristics, it is possible to detect abnormal pre-cancerous or cancerous tissue while the development of such tissue is at an early stage. It should be understood that the method and system of the present invention is applicable to any epithelial derived cancer, such as, but not limited to, prostate, colon, breast, esophageal, and nasopharyngeal cancers, as well as other epithelial malignancies, such as lung, gastric, uterine cervix, endometrial, skin and bladder.

Specifically, in cancers affecting mucosal or epithelial tissues, transport alterations may be sufficiently large to suggest that they are a consequence of an early mutation, affecting a large number of cells (i.e., a field defect). In this case, they may be exploited as potential biomarkers for determining which patients should be either more frequently monitored, or conversely, may be used to identify particular regions of epithelium that require biopsy. The latter is especially helpful in the case of atypical ductal hyperplasia or ductal carcinoma in situ (DCIS), which are more difficult to detect mammographically, or by clinical breast examination without having to resort to an invasive biopsy.

Applying the methods of the present invention, several observations have been made:

(1) Differences in the total impedance are observed when comparing malignant breasts with benign or normal breasts. The total impedance is higher comparing malignant to benign breasts with the total impedance exceeding 50,000 ohms, or even higher, for the malignant breasts.

(2) Total capacitance was lower overall, comparing malignant with benign or normal breasts.

(3) The impedance curves for normal and malignant breasts separate at lower frequencies.

(4) The shape of the curves differs depending on the pathological condition of the breast.

(5) Electrical resistance of the tumor may be lower at lower frequencies, for example, in the range of about 1 to about 0.1 hertz. This also depends on the type and size of the tumor.

(6) Capacitance of the tumor may be higher at the lower frequencies. This also depends on the pathological type and size of the tumor.

(7) Differences exist between phase angle, characteristic capacitance and the suppression of the center of the impedance arc depending on the pathological status of the breast.

(8) When current is passed across a malignant tumor from another site on the breast or body, rather than from the nipple to the surface of the breast, the impedance may be lower when the voltage drop is measured across the tumor rather than between the nipple and the tumor i.e., across ductal epithelium. The capacitance is usually higher when the measurement is made across a malignant tumor, rather than across the ductal epithelium. Therefore a combination of measurements; nipple to breast surface (transepithelial impedance spectroscopy), body surface to breast surface (transtumor impedance), and transepithelial potential (ductal epithelium in series with skin provides the optimum diagnostic information.

The methods of the present invention are particularly useful when use is made of the entire frequency range between about 60,000 Hertz and about 0.1 Hertz, although most of the discriminatory information is observed at frequencies below about 200 Hz. The preferred protocol is to take 5-10 electrical measurements (impedance, reactance, phase angle, resistance, etc.) between about 60,000 Hz and about 200 Hz and then take as many measurements as possible (taking into consideration, for example, the comfort of the patient, response time of the equipment, etc.) between about 200 and about 0.1 Hz; preferably between about 150 Hz and about 0.1 Hz; more preferably about 100 Hz and about 0.1 Hz; for example between about 50 Hz and about 0.1 Hz. In practice, this can mean taking about 20 to about 40 measurements in one or more of the lower frequencies ranges.

It has also been observed that the application of alternating suction and release opens up the nipple ducts so that impedances are generally lower if this protocol is followed. This will typically lower the impedance in the high frequency range. This reduces measurement noise and enhances current passage along the ducts to the tumor site. Further improvement can be made in lowering the impedance of the nipple and larger collecting ducts by using alcohol or a dekeratinizing agent such as Nuprep® to remove keratin plugs in the surface duct openings on the nipple surface. Methods for opening up the ductal system are known for ductoscopy (e.g., Acueity), obtaining nipple aspirate fluid (NAF) or ductal lavage (e.g., CYTYC), but this technology has not previously been applied to the field of the present invention. A particularly improved device will employ an automated suction pump connected to a manometer to suction rhythmically, analogous to a breast pump, then employ a holding suction pressure at a predetermined level and then change the holding pressure to another level so that the effect of altered suction on the impedance spectra can be used as a diagnostic test. Without wishing to be bound by theory, it is believed that a difference in electrical response, for example a different impedance curve, arises due ductal collapse with the application of suction in a normal breast whereas the presence of malignancy in a duct inhibits such collapse.

Mechanical pressure can also be used to provide additional diagnostic information during DC and AC impedance measurement to characterize breast tissue. In this manner, positive pressure is applied to the skin surface and negative pressure, or vacuum is applied to the nipple. In this manner an additional approach can be used to obtain further diagnostic information that can be independently used or can be used in combination with the technique relating to nipple aspiration.

Figure 22:
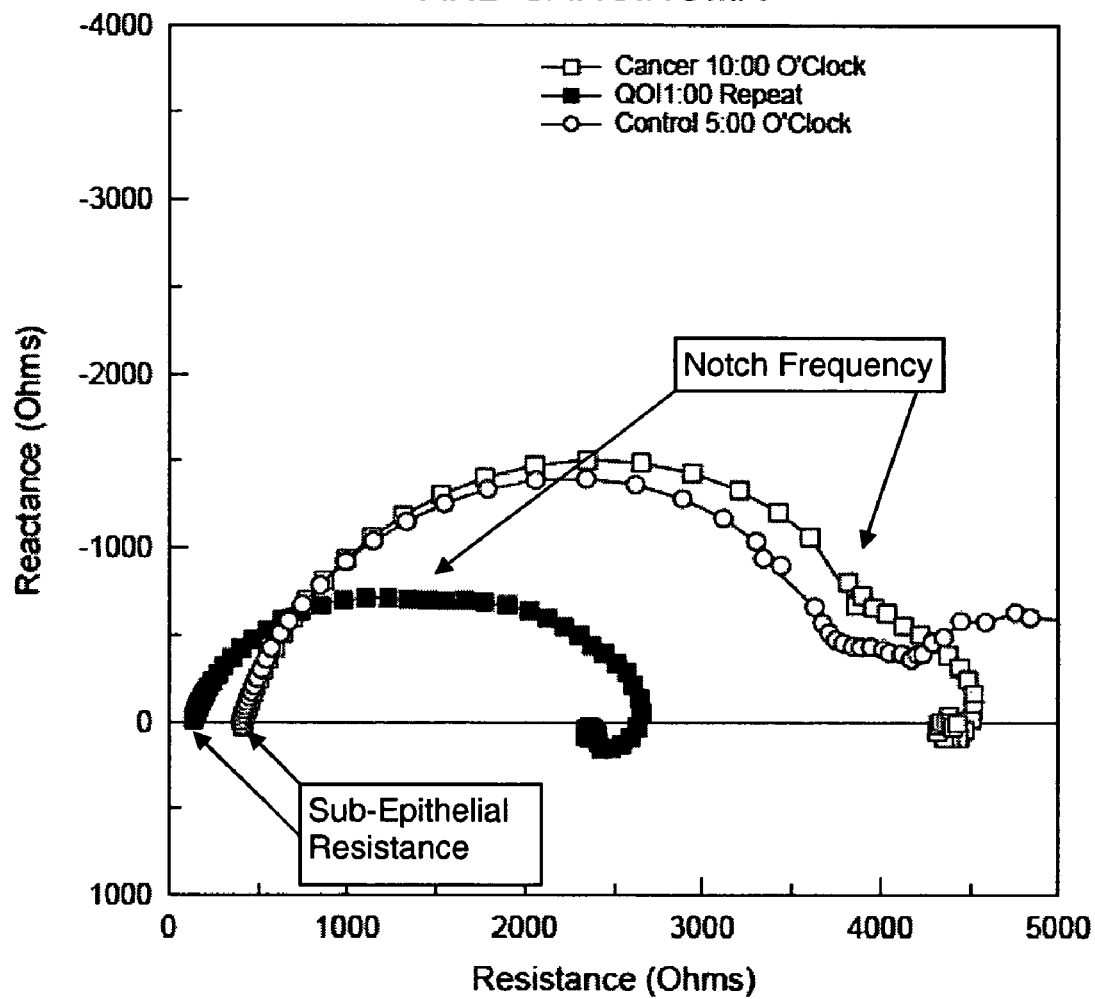
FIG. 22 illustrates the impedance profiles of a fibroadenoma and carcinoma.

Two patterns of impedance and open circuit potential have been observed from transepithelial impedance spectroscopy and DC measurements in patients with benign or malignant breast lesions. FIG. 22 demonstrates one source of false positives that can occur with a low impedance fibroadenoma (a benign lesion). Two patterns exist in the impedance spectral profile of breast cancer. The first change is an increase in impedance, particularly at low frequency. Without wishing to be bound by theory, this is believed due to the ducts becoming packed with tumor cells (ductal-carcinoma in-situ, DCIS) which increases the resistance of the ductal epithelium. Once an invasive carcinoma and mass lesion develops within a duct system, the tight-junctions between cells break down, resulting in a decrease in impedance, particularly at low frequencies. In FIG. 22 the open circles demonstrate the impedance spectra of a control ductal system in a patient with a carcinoma of the breast in a quadrant of the breast that is uninvolved by tumor. It can be seen that the open circles on the right side of the graph form a second circular arc (Cole plot) that extends beyond the right side vertical Y-axis. This indicates that a high impedance ductal system exists in the control quadrant of this patient's breast. In the opposite quadrant of the same patient's breast a mass has developed. The impedance spectrum of that breast quadrant is depicted by the open squares. The second semicircular arc has now been replaced by a low impedance Cole plot that passes below the X-axis. Since we have previously observed that the low frequency impedance arc appears to be dominated by the terminal ducts, it is likely that the terminal ducts have become less, electrically resistant in the region of the developing cancer. This suggests a lower electrical impedance at this stage in the development of the cancer.

In another patient the impedance spectra over a suspicious mass appears similar to the developing cancer. This lesion had an impedance spectra depicted by filled squares. The impedance curve has lost its low impedance curve similar to the developing cancer. The patient underwent a biopsy, the results of which demonstrated that the mass was a benign fibroadenoma. Several features do however distinguish the developing cancer from the fibroadenoma:

(1). The middle part of the impedance arc is flattened in the fibroadenoma (filled squares) compared with the carcinoma (open squares);

(2) The notch frequency occurs at about 30 Hz for cancer (this may occur as low as 1 Hz in cancer) and about 100 Hz for the fibroadenoma. Notch frequency is the frequency at which there appear two separate RC time-constants in the impedance spectra resulting in two incompletely fused arcs. It is the frequency at which the two arcs or double humps appear to partly separate. (See Jossinet et al., Ann. NY Acad. Sci. 1999; 873: 30-41, incorporated herein by reference.) The acronym RC stands for Resistor-Capacitor. The product RC is referred to in the art as the time constant, and is a characteristic quantity of an RC circuit. For example, when t=RC, the capacitor has charged to a fraction equal to $1-1/e$, or about 63% of its final value. Typically the units of RC are seconds or milliseconds. When the time constant of the high frequency RC components of the circuit have a significantly different time constant compared to the low frequency RC components, the resulting figure exhibits two separate semi-circles on a Nyquist plot. If the time constants are close to one another, the semi-circles will appear to be fused. With better separation, in other words time constants that differ more, the information obtained is more diagnostically useful. As described above, a greater degree of diagnostic information in the present invention is obtained in the low frequency range; and (3) The subepithelial resistance (the intercept of the high-frequency impedance curve with the x-axis on the left side of the curve) is much lower in the fibroadenoma (140 ohms) than in the cancer (420 ohms).

As noted above, an alternative approach that can be used to identify abnormalities in the breast and distinguish benign from malignant disease involves the application of mechanical pressure or compression to occlude the ductal pathway and thereby increase the impedance pathway for the passage of electrical current through the breast. The application of mechanical pressure or compression, in other words positive pressure (in contrast with the application of vacuum to, e.g., nipple ducts as described elsewhere herein), can be accomplished by various means well-known to the skilled practitioner. For example, one or more fingers or the hand can be used to palpate an area of the breast, including a suspicious area or an adjoining area thereto. Alternatively, a mechanical device, such as a pressure transducer, can be used to apply a finite or defined degree of pressure to a specific area. Additionally, the use of mechanical pressure can be combined with the use of suction or vacuum as described above. For convenience, the use of mechanical pressure can be referred to as the mechanical pressure protocol and it can be accomplished by one or more of the following steps in the suggested order or in other sequences:

(1) Measurement of an impedance spectrum over a region of tissue where an abnormality is suspected (suspicious region).

(2) Measurement of an impedance spectrum over a region of tissue where no abnormality is suspected (control region).

(3) The application of mechanical pressure or compression over the suspicious region.

(4) The measurement of the impedance spectrum in the suspicious region following the application of mechanical pressure.

(5) The application of mechanical pressure or compression over the control region.

(6) The comparison of the impedance profile before and after compression in the suspicious region.

(7) The comparison of the impedance profile before and after compression in the control region.

(8) The comparison of the impedance profile of the suspicious region to the control region.

(9) Using 6, 7 and 8 alone or in combination to diagnose the normal or diseased state of the tissue.

(10) Measurement of the kinetics of the change in impedance when pressure is applied or released over a region of tissue.

(11) Using the kinetics of the change in impedance to diagnose the normal or diseased state of the tissue.

(12) Using a combination of a single or multiple pressure transducer with steps 3-11 to obtain both a pressure profile, and an impedance profile.

(13) Using a combination of the applied pressure profile with the changes in the impedance profile to diagnose the normal or diseased state of the tissue.

(14) Using a combination of the 1-13 with changes in the suction pressure applied to the nipple-sensor aspirator-cup.

(15) Using a combination of the altered impedance profile following changes in the applied suction pressure to the nipple-sensor aspirator-cup with steps 1-13 to diagnose the normal or diseased state of the tissue.

Figure 23:
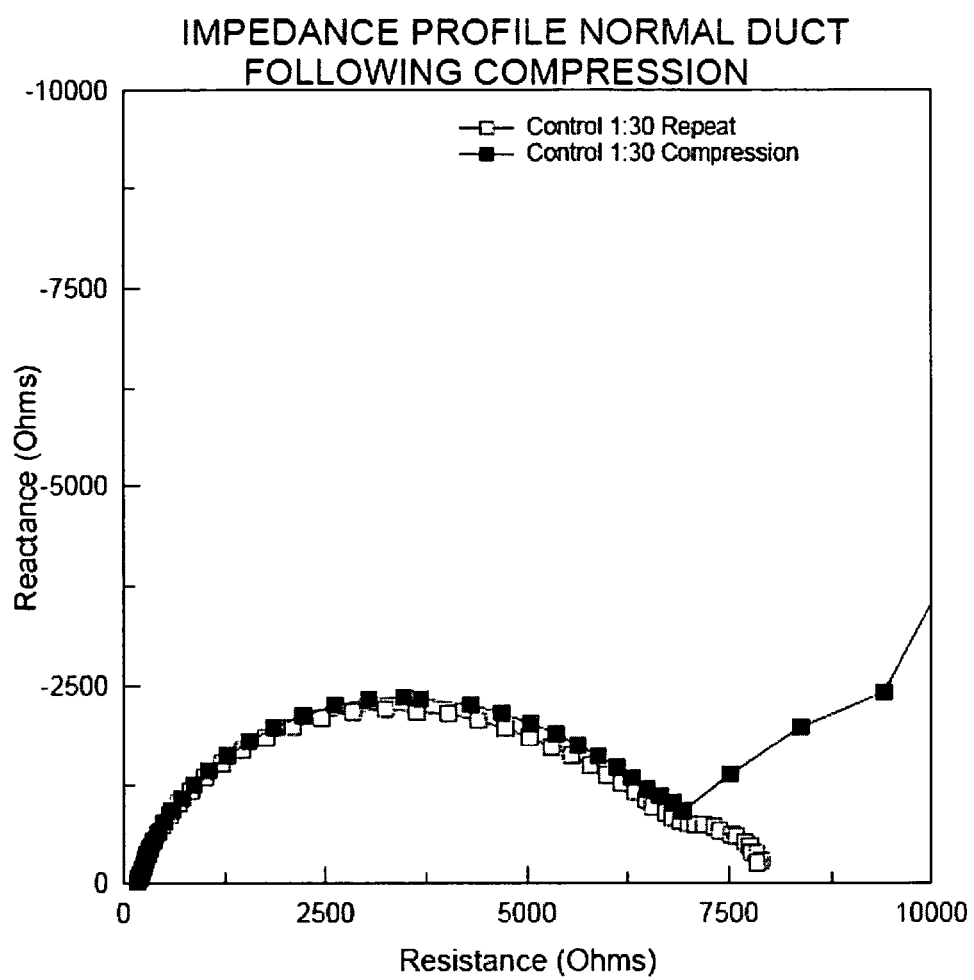
FIG. 23 illustrates the impedance profile of a normal duct following compression.
Figure 24:
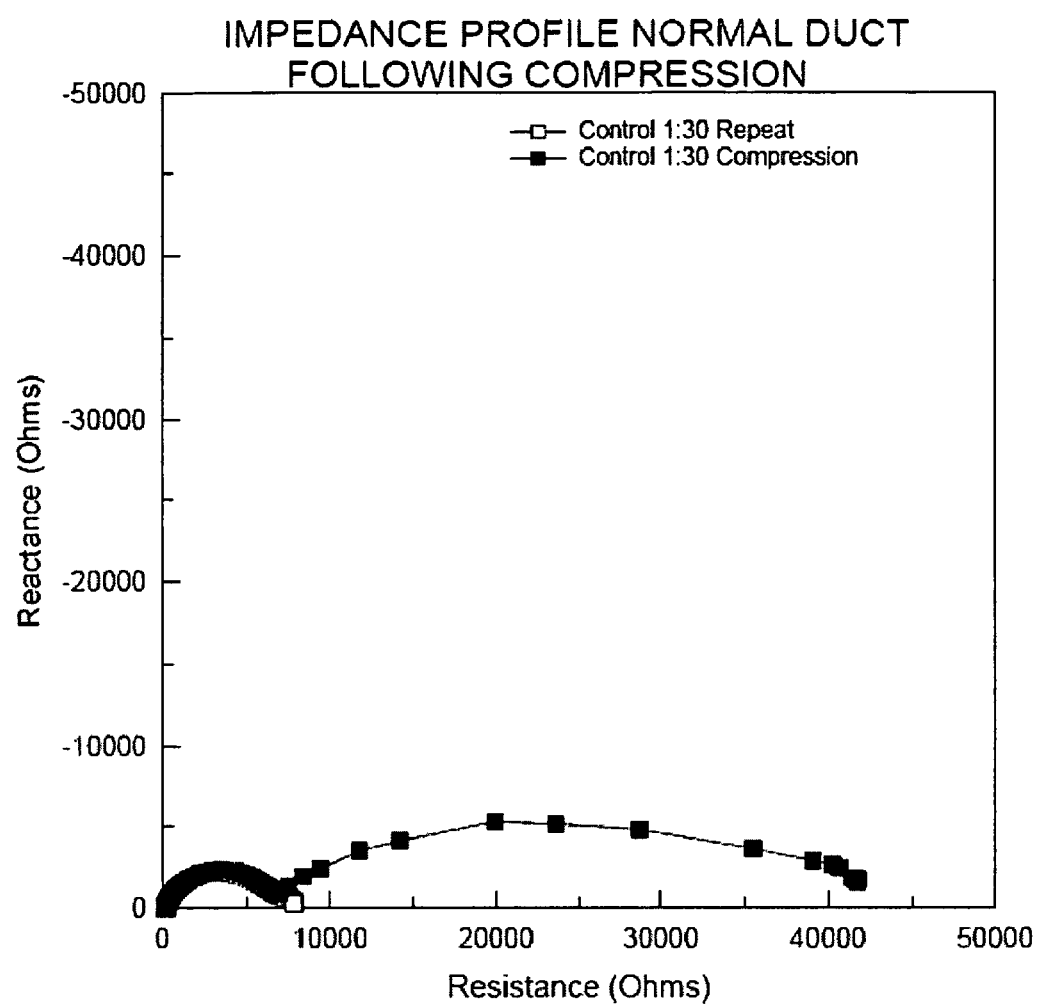
FIG. 24 illustrates the same results as in FIG. 23 with an expanded range for the X-axis.

Ducts containing tumor will generally be less compliant, and therefore less compressible than normal ducts not filled with tumor cell. This is depicted in FIG. 23. The open squares depict the impedance spectra of a normal duct which appears to have at least two time constants. The notch frequency (the point at which the two impedance curves incompletely fuse) in this normal duct is at about 4 Hz. When a pressure of up to 1 kg cm$^{-2}$ was applied over the breast surface electrode a new impedance spectrum was measured at 59 frequencies logarithmically spaced between 60,000 Hz and 0.1 Hz (filled squares). The impedance of the low frequency curve (below 4 Hz) is markedly increased due to occlusion of the more compliant duct. In contrast, there is virtually no effect on the impedance curve above 4 Hz. FIG. 24 demonstrates the effect on a large scale of the X-axis. Note that the impedance increases from approximately 7850 ohms to almost 42,060 ohms. The open squares (no compression) are obscured by the closed squares (compression).

Figure 25:
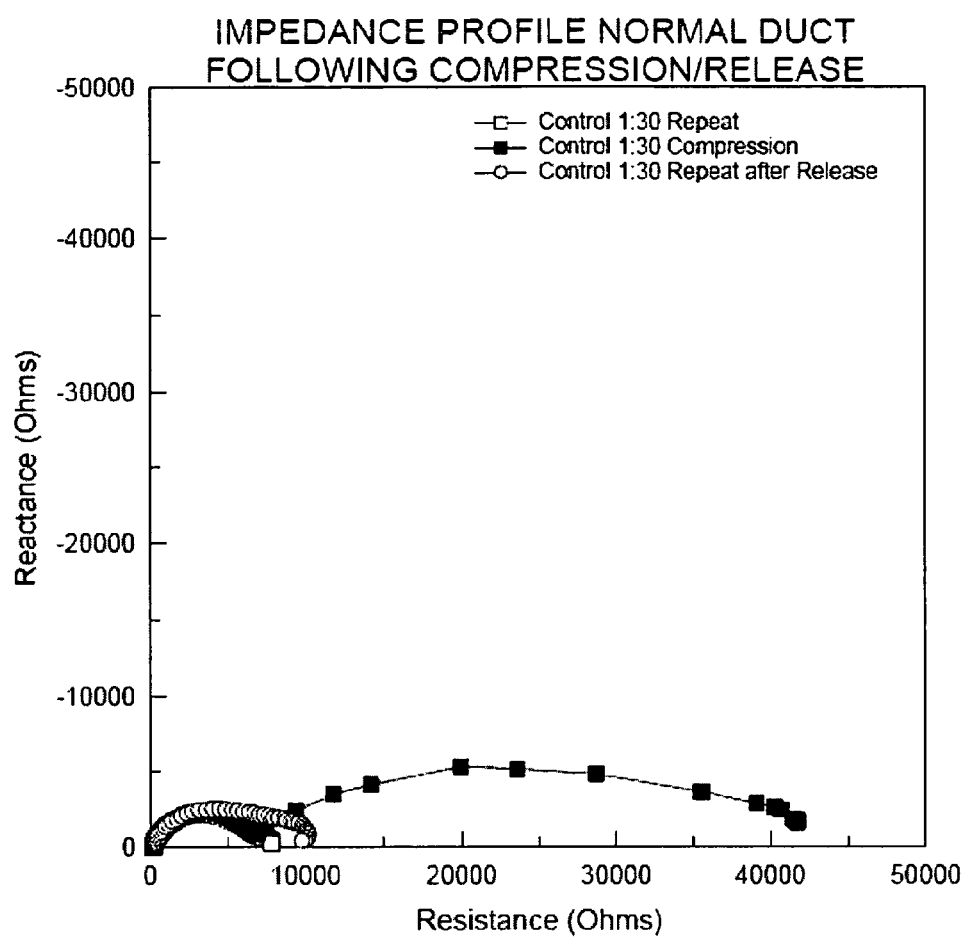
FIG. 25 illustrates the impedance profile of a normal duct following compression and release.

FIG. 25 depicts the release of compression on the duct (open circles) with the return of the impedance profile almost to control (pre-compression) levels. Note that the kinetics and shape of the release curve has specific characteristics in normal as opposed to abnormal tissue. For example, the return of the impedance curve takes several minutes due to the compliance properties of the ductal and surrounding parenchymal tissue. These properties can be used to characterize the pathological state of the tissue.

Figure 26:
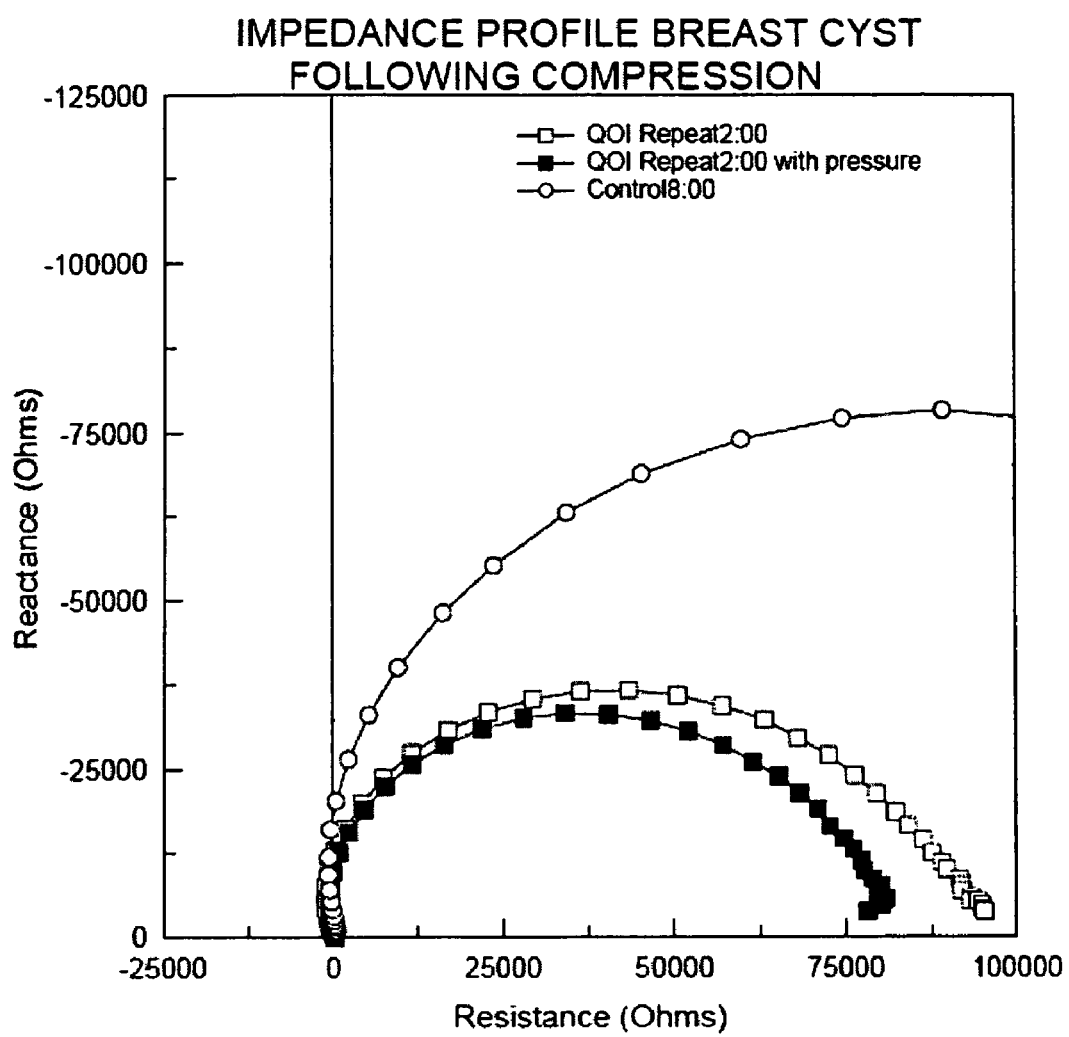
FIG. 26 illustrates the impedance profile of a breast cyst following compression.

FIG. 26 demonstrates the same protocol applied to a cyst. The open square QOI2:00 (quadrant of interest at the 2:00 o'clock position) depicts the impedance spectrum over a cyst. When pressure is applied (closed square) the impedance decreases, as may be expected as the current pathway is decreased because of a decrease in the anterior-posterior diameter of the cyst with compression. The control quadrant is depicted by open circles, which pass off the scale. A large cyst is expected to have a lower impedance than the surrounding tissue because it conducts electricity better.

Figure 27:
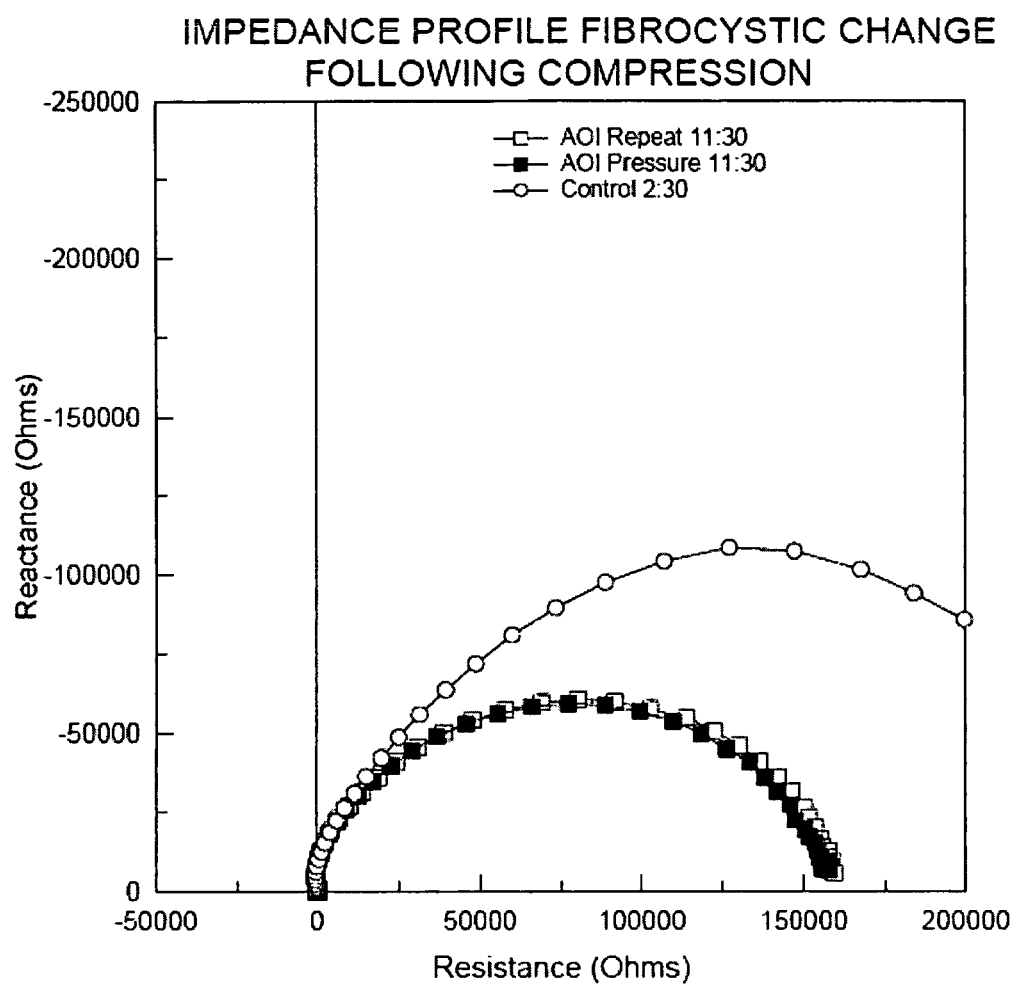
FIG. 27 illustrates the impedance profile following compression of fibrocystic breast tissue.

FIG. 27 demonstrates the same protocol applied to a region of fibrocystic disease. Since the cystic component is minimal i.e., there is a more non-compliant fibrous element in this example, there is a minimal effect observed with compression.

Figure 28:
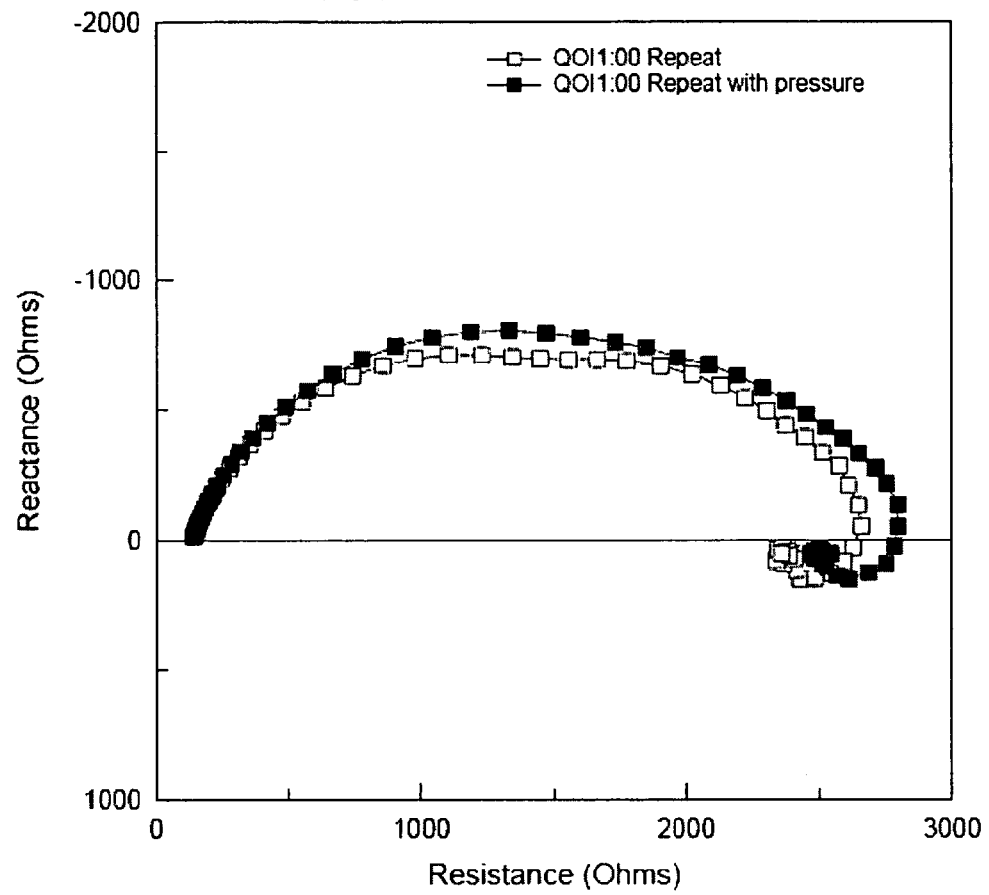
FIG. 28 illustrates the impedance profile following compression of fibroadenoma in breast tissue.

FIG. 28 demonstrates the same fibroadenoma shown in FIG. 22. This fibroadenoma has a significantly lower impedance than is usually observed and the lesion can be confused with a carcinoma. The same pressure protocol was applied and an increase of impedance was identified although less than that observed in a normal duct (FIG. 24 and FIG. 25). It should be noted that the surrounding ductal structure is less disrupted in a fibroadenoma than in carcinoma and therefore some compression of the ductal structure was possible. The same compression protocol applied to the carcinoma in FIG. 22 results in no appreciable change in the impedance profile, apparently because the ducts have already been disrupted by the tumor and are less compressible.

FIG. 29 depicts a more typical fibroadenoma where the impedance is higher. The control quadrant (open circles) has a somewhat noisy impedance curve, but shows two partially fused RC curves because of normal ductal structure. In this case the pressure protocol results in minimal change in the impedance spectrum. As has been demonstrated, the application of pressure in combination with the electrical measurements described in detail above to selected regions of the breast exhibiting suspicious tissue can be used effectively to distinguish between malignant and other types of abnormal tissue.

A number of variations are possible for devices to be used with the present invention. Further, within a device design, there are a number of aspects that may be varied. These variations, and others, are described below.

One probe or other device includes a plurality of miniaturized electrodes in recessed wells. Disposable commercially available silicon chips processing functions, such as filtering, may perform surface recording and initial electronic processing. Each ECM solution or agent may be specific to the individual electrode and reservoir on the chip. Thus, for one measurement, a particular set of electrodes is used. For another measurement, for example, at a different ionic concentration, a different set of electrodes is used. While this produces some variations, as the electrodes for one measurement are not located at the same points as for another, this system provides generally reliable results.

An alternative approach is to use fewer electrodes and use a flow-through or microfluidic system to change solutions and agents. Specifically, solutions or agents are changed by passing small amounts of electrical current to move solution or agent through channels and out through pores in the surface of the probe. In this embodiment, the electrode remains in contact with the same region of the skin or ductal epithelium, thus eliminating region-to-region variation in measurement. This approach requires time for equilibration between different solutions.

In detecting the presence of abnormal pre-cancerous or cancerous breast tissue, a hand-held probe is provided for obtaining surface measurements at the skin. The probe may include electrodes for passing current as well as for measuring. An impedance measurement may be taken between the nipple cup electrode and the hand-held probe, or may be taken between electrodes on the hand-held probe. Alternatively, a ductoscopic or non-optical ductal probe may be interfaced with one or more miniaturized electrodes. After taking initial DC measurements, a wetting/permeabilizing agent may be introduced to reduce skin impedance or one of the methods described hereinabove may be used. The agent may be introduced using a microfluidic approach, as described above, to move fluid to the surface of the electrodes. Alternatively, surface electrodes that just penetrate the stratum corneum may be used to decrease impedance.

Regardless of the configuration of the device, FIG. 1 is a schematic of a DC and AC impedance measurement system 100 used in cancer diagnosis, consistent with the present invention. The system 100 interfaces with a probe device 105 including multiple electrodes, wherein the actual implementation of the probe device 105 depends on the organ and condition under test. The probe device 105 may incorporate the electrodes attached to a needle, body cavity, ductoscopic, non-optical ductal or surface probe. A reference probe 110 may take the form of an intravenous probe, skin surface probe, nipple-cup or ductal epithelial surface reference probe depending on the test situation and region of breast under investigation.

To avoid stray capacitances, the electrodes may be connected via shielded wires to a selection switch 120 which may select a specific probe 105 following a command from the Digital Signal Processor (DSP) 130. The selection switch 120 also selects the appropriate filter interfaced to the probe 105, such that a low pass filter is used during DC measurements and/or an intermediate or high pass filter is used during the AC impedance measurements. The selection switch 120 passes the current to an amplifier array 140 which may be comprised of multiple amplifiers or switch the signals from different electrodes through the same amplifiers when multiple electrodes are employed. In a preferred embodiment digital or analogue lock-in amplifiers are used to detect minute signals buried in noise. This enables the measurement of the signal of interest as an amplitude modulation on a reference frequency. The switching element may average, sample, or select the signal of interest depending on the context of the measurement. This processing of the signal will be controlled by the DSP following commands from the CPU. The signals then pass to a multiplexer 150, and are serialized before conversion from an analogue to a digital signal by the ADC. A programmable gain amplifier 160 matches the input signal to the range of the ADC 170. The output of the ADC 170 passes to the DSP 130. The DSP 130 processes the information to calculate the DC potential and its pattern on the ductal-epithelial or skin surface as well as over the region of suspicion. In addition the impedance at varying depth and response of the DC potential and impedance to different ECM concentrations of ions, drug, hormones, or other agent are used to estimate the probability of cancer. The results are then sent to the CPU 180 to give a test result 185.

Alternatively the signal interpretation may partly or completely take place in the CPU 180. An arbitrary waveform generator 190 or sine wave frequency generator will be used to send a composite waveform signal to the probe electrodes and tissue under test. The measured signal response (in the case of the composite wave form stimulus) may be deconvolved using FFT (Fast Fourier Transforms) in the DSP 130 or CPU 180 from which the impedance profile is measured under the different test conditions. An internal calibration reference 195 is used for internal calibration of the system for impedance measurements. DC calibration may be performed externally, calibrating the probe being utilized against an external reference electrolyte solution.

Figure 2:
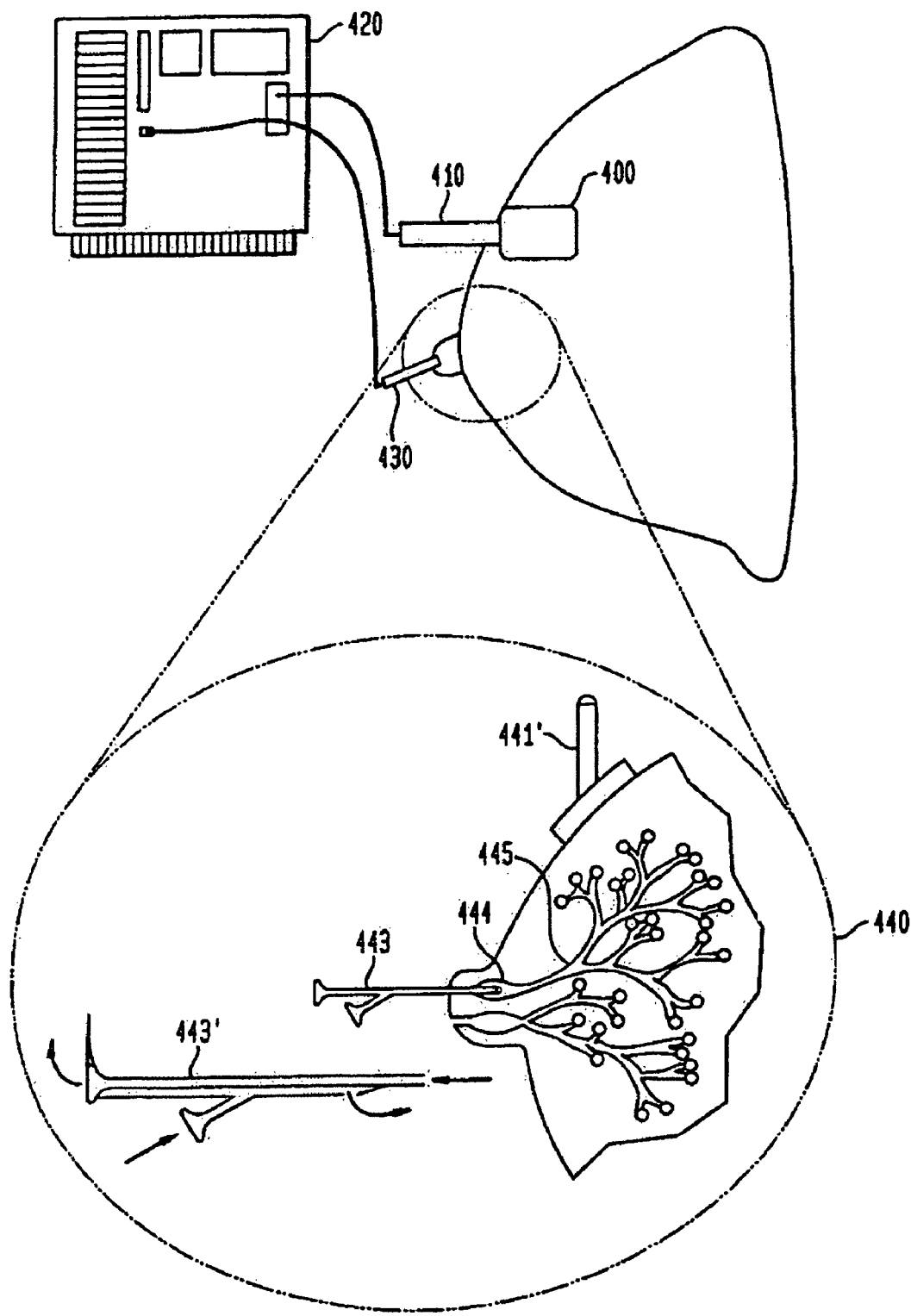
FIG. 2 illustrates an exemplary embodiment of a device suitable for use with systems and methods consistent with the present invention.

FIG. 2 includes a handheld probe 400, consistent with the present invention, which may be applied to the surface of the breast. The probe may include a handle 410. The probe 400 may be attached, either directly or indirectly using, for example, wireless technology, to a measurement device 420. The probe 400 may be referenced to an intravenous electrode, a skin surface electrode, other ground, nipple electrode, or ductal probe electrode within the duct or at the nipple orifice. In one embodiment, illustrated in FIG. 2, the reference is a nipple electrode or ductal probe 430, illustrated in greater detail at close-up 440. One advantage of this configuration is that DC electropotential and impedance can be measured between the nipple electrode 430 and the probe 400. The measurement is thus a combination of the DC potentials or/and impedance of the breast ductal epithelium, non-ductal breast-parenchyma, and the skin.

Referring to close-up 440, the ductal probe is inserted into one of several ductal orifices that open onto the surface of the nipple. Ductal probe 443 is shown within a ductal sinus 444, which drains a larger collecting duct 445.

Another advantage of using a nipple electrode is that a solution for irrigating the ductal system may be exchanged through the probe, permitting introduction of pharmacological and/or hormonal agents. As shown in magnified nipple probe 443, 443' fluid can be exchanged through a side port. Fluid may be infused into the duct and aspirated at the proximal end (away from the nipple) of the nipple probe. Different electrolyte solutions may be infused into the duct to measure altered permeability of the ductal epithelium to specific ions or the epithelium may be probed with different drugs to identify regions of abnormality. Estradiol, or other hormonal agents, may be infused into a breast duct to measure the abnormal electrical response associated with pre-malignant or malignant changes in the epithelium.

It should be understood that different configurations may also be used, such as a modified Sartorius cup that applies suction to the nipple. With this configuration, gentle suction is applied to a cup placed over the nipple. Small amounts of fluid within the large ducts and duct sinuses make contact with the electrolyte solution within the Sartorius cup, establishing electrical contact with the fluid filling the breast ducts. DC or AC measurements may then be made between the cup and a surface breast probe.

Figure 3:
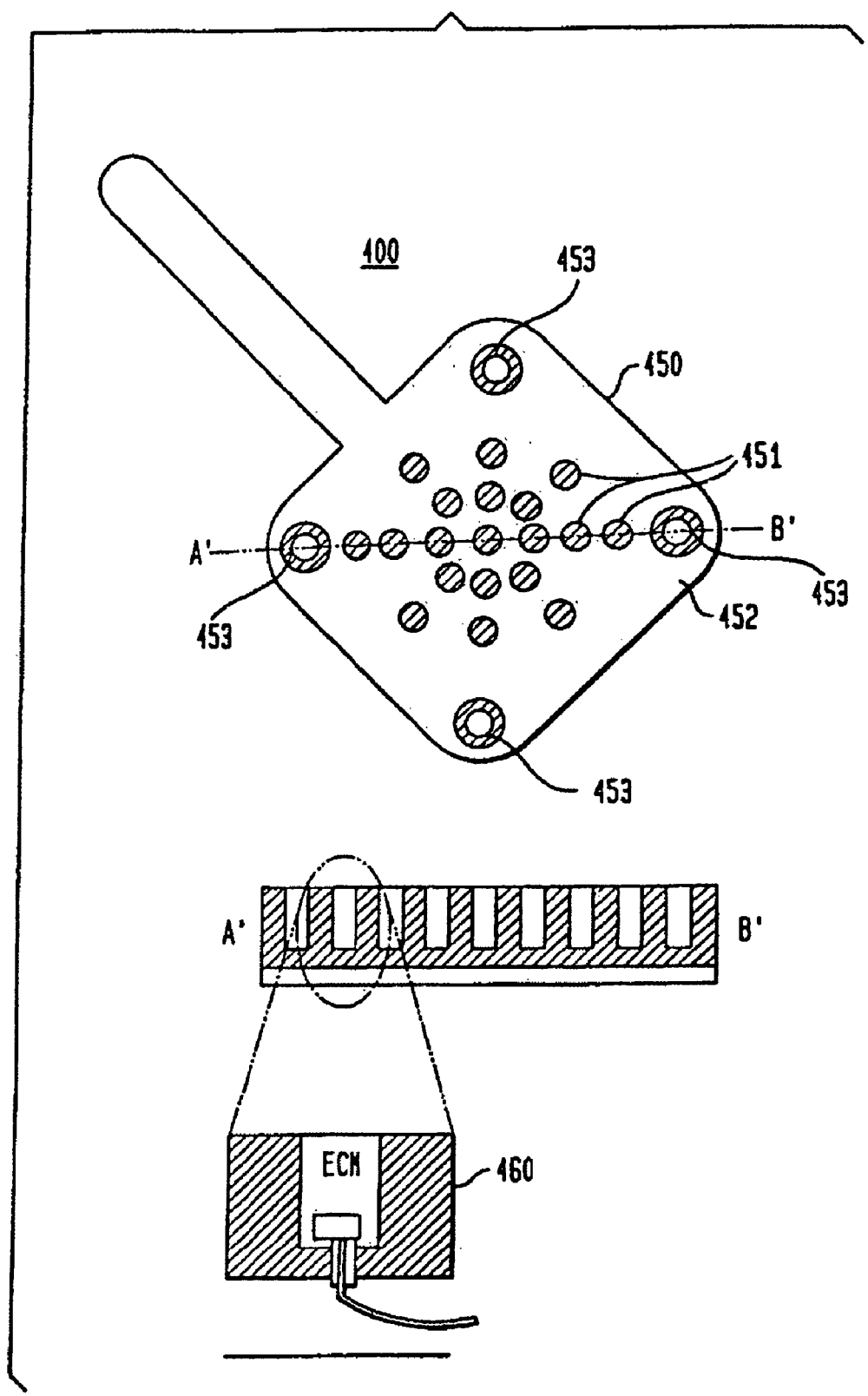
FIG. 3 illustrates an exemplary embodiment of a surface measurement probe suitable for use with systems and methods consistent with the present invention.

FIG. 3 illustrates the probe 400 of FIG. 2 in greater detail. The skin contact of the surface 450 is placed in contact with the breast. The surface electrodes 451 measure DC or AC voltages. The current passing electrodes 452 are used for impedance measurements. Probe 400 may also include one or more recessed wells containing one or more ECMs. Multiple sensor electrode arrays may be attached to the surface probe together with current passing electrodes. The individual electrodes may be recessed and ECMs with different composition may be used to pharmacologically, electrophysiologically, or hormonally probe the deeper tissues or epithelium under test. Spacing of the electrodes may be greater for the breast configuration than for other organ systems so that deeper tissue may be electrically probed and the impedance of the deeper tissue evaluated. This probe may either be placed passively in contact with the surface of the breast or held in place by pneumatic suction over the region of interest. Ports may be placed for the exchange of solutions or for fluid exchange and suction (not shown). Guard rings (not shown) may be incorporated to prevent cross-talk between electrodes and to force current from the contact surface into the breast. In this configuration there are four current passing electrodes [453] each positioned radially 90° apart. This permits current to be passed and the voltage response to be measured in perpendicular fields. The electrodes will be interfaced via electrical wire, or wireless technology, with the device described in FIG. 1 above.

Further embodiments of this technique may involve the use of spaced electrodes to probe different depths of the breast, and the use of hormones, drugs, and other agents to differentially alter the impedance and transepithelial potential from benign and malignant breast tissue, measured at the skin surface. This enables further improvements in diagnostic accuracy.

Figure 4:
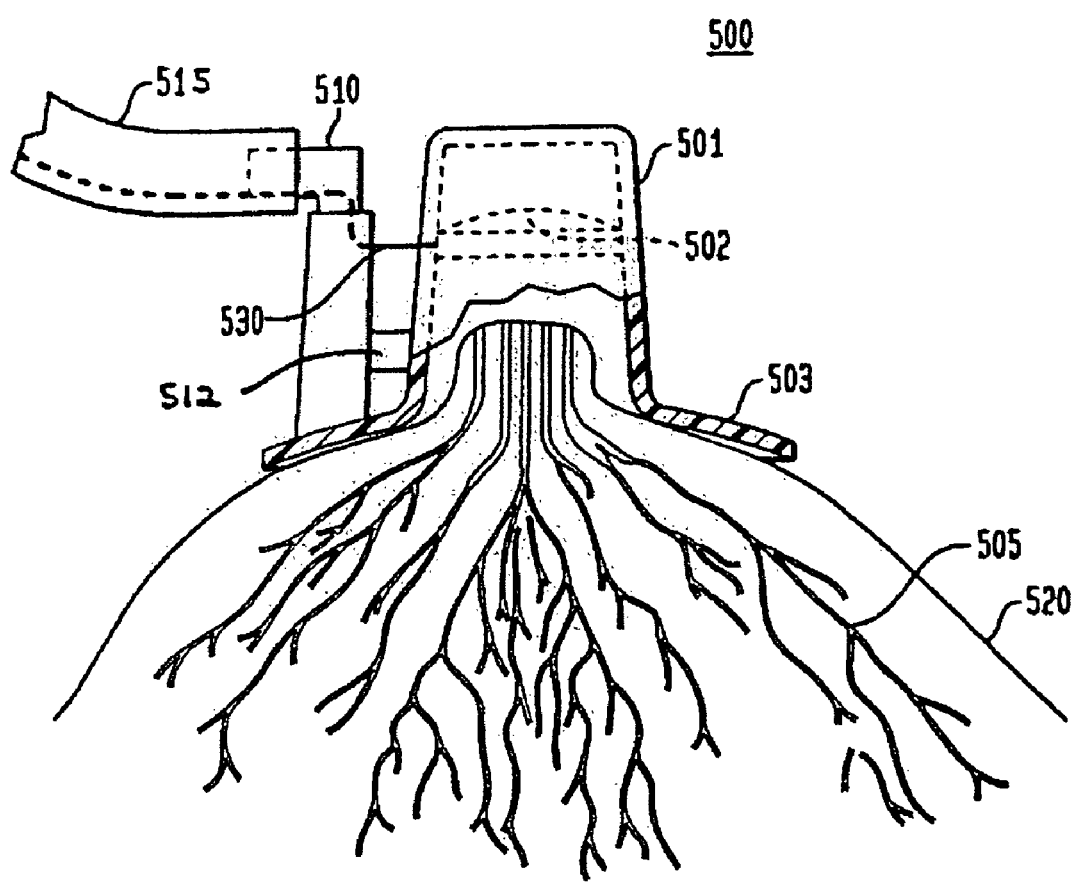
FIG. 4 illustrates an exemplary embodiment of a nipple electrode suitable for use with systems and methods consistent with the present invention.

FIG. 4 illustrates a nipple cup electrode [500] that may be used as a reference, current passing, voltage measuring or combination electrode [502]. In this configuration suction and fluid exchange is applied to the electrode housing [501] through a side port [510] connected by a flexible hose [515] to a suction device, aspirator or syringe (not shown). The flange

[503] at the base of the cup is applied to the areola of the breast [520]. Pneumatic suction is applied through the side port and communicated to the housing by passage [512] so as to obtain a seal between the breast [520] and the nipple electrode [501]. Electrolyte solution is used to fill the cup and make electrical contact with the underlying ductal system. Fluid may be exchanged, or pharmacological and hormonal agents introduced, by applying alternating suction and injecting fluid or drugs into the cup through the side port. The pneumatic suction will open up the duct openings [505] either by itself or after preparation with alcohol or de-keratinizing agents to remove keratin plugs at the duct openings at the surface of the nipple. The nipple cup electrode [502] may be interfaced by means of an electrical connection [530] or by a wireless connection (not shown) with the devices illustrated in FIGS. 1-3 to obtain DC potential, AC impedance or combination measurements.

Figure 5:
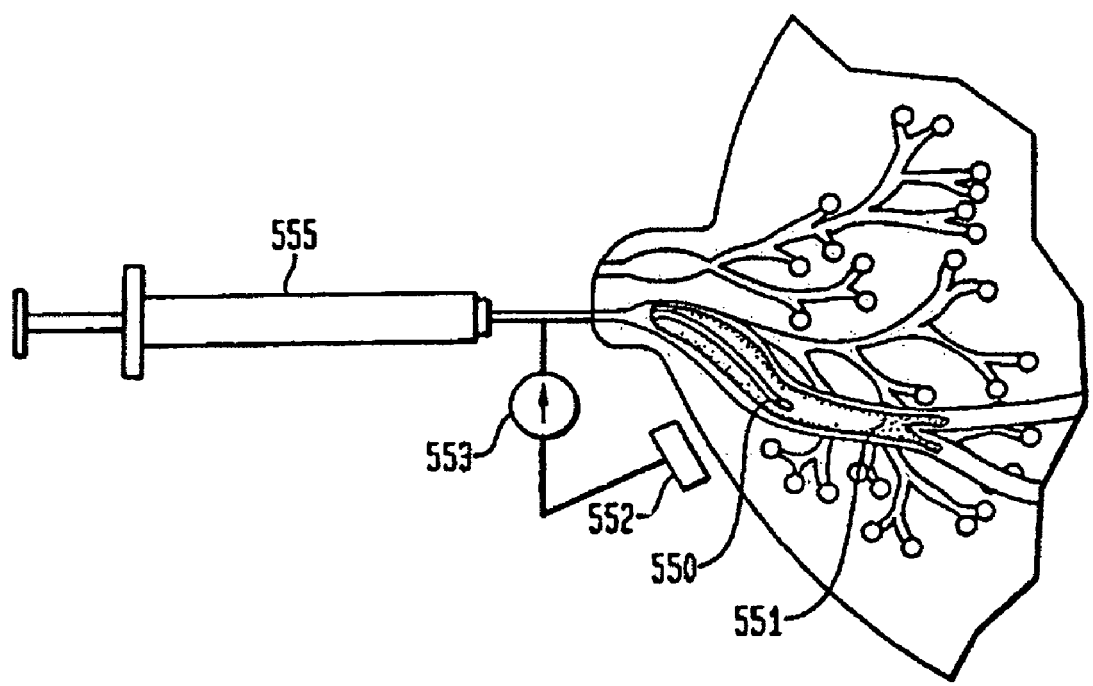
FIG. 5 illustrates an exemplary embodiment of a ductal electrode probe suitable for use with systems and methods consistent with the present invention.

FIG. 5 illustrates an alternative approach where an individual duct is probed with a flexible catheter electrode [550] attached to a syringe [555]. This may be used when a specific duct produces fluid and diagnosis is to be performed on the specific ductal system producing the fluid. In this configuration a saline filled syringe is connected to a flexible electrode [550], which is inserted into the duct Fluid may be exchanged, or drugs and hormones may be infused into the duct, through the catheter. An electrode within, or attached to the syringe makes electrical contact with the individual ductal system, and the surface probe electrodes [552] complete the circuit so that the DC potential, AC impedance or a combination of both may be measured across the ductal epithelium, skin and intervening breast parenchyma in combination with the systems described in FIGS. 1-3. Another approach would be to use a ductoscope in combination with a surface probe with the electrode(s) interfaced with the ductoscope.

Devices to measure the electrophysiological characteristics of tissue and the differences between normal and abnormal tissue may include those known in the art such as electrical meters, digital signal processors, volt meters, oscillators, signal processors, potentiometers, or any other device used to measure voltage, conductance, resistance or impedance.

DC potential is usually measured using a voltmeter, consisting of a galvanometer in series with a high resistance, and two electrodes (one working and one reference). Voltmeters may be analog or digital. Ideally these should have an extremely high input resistance to avoid current-draw. DC potential may also be measured with an oscilloscope.

Impedance may be measured using a number of approaches. Without limitation, examples include phase-lock amplifiers, which may be either digital or analog lock-in amplifiers. Pre-amplifiers may be used in conjunction with the lock-in amplifier to minimize stray currents to ground improving accuracy. Digital lock-in amplifiers are based on the multiplication of two sine waves, one being the signal carrying the amplitude-modulated information of interest, and the other being a reference signal with a specific frequency and phase. A signal generator can be used to produce the sine waves or composite signal to stimulate the tissue. Analog lock-in amplifiers contain a synchronous rectifier that includes a phase-sensitive detector (PSD) and a low-pass filter. Other approaches include the use of an impedance bridge with an oscillator to produce an AC sine wave. These devices when automated are referred to as LCR-meters and use an auto-balancing bridge technique. Constant current or constant voltage current sources may be used. In one preferred embodiment, a constant current source is used. Rather than an oscillator with a fixed frequency signal a signal generator, which produces, superimposed sine waves may be used.

The tissue response is deconvolved using fast Fourier transforms or other techniques. Bipolar, tripolar or tetrapolar current and voltage electrodes may be used to make measurements. In one preferred embodiment tetrapolar electrode configurations are employed to avoid inaccuracies that are introduced due to electrode polarization and electrode-tissue impedance errors. Rather than impedance, current density may be measured using an array of electrodes at the epithelial or skin surface. Impedance may also be measured using electromagnetic induction without the need for electrode contact with the skin or epithelium.

In order to process large amounts of data, the methods of the present invention could be implemented by software on computer readable medium and executed by computerized equipment or central processor units.

Example 1

Breast Cancer

As mentioned above, impedance and DC electrical potential have been used separately at the skin's surface to diagnose breast cancer. Neither of these methods measures the ductal transepithelial DC or AC electrical properties of the breast. This significantly reduces the accuracy of the approach, because the origins of breast cancer are within the ductal epithelium, and not the surrounding breast stroma. Accuracy is further improved when the transepithelial measurements of impedance and DC potential are combined. The use of pharmacological and/or hormonal agents in combination with impedance or DC electrical potential measurements, provide a more effective method for detecting abnormal pre-cancerous or cancerous breast tissue.

Breast cancer develops within a background of disordered proliferation, which primarily affects the terminal ductal lobular units (TDLUs). The TDLUs are lined by epithelial cells, which maintain a TEP (transepithelial potential). In regions of up-regulated proliferation, the ducts are depolarized. The depolarization of ducts under the skin surface results in skin depolarization. The depolarization is significantly attenuated compared to that which is observed using a transepithelial ductal approach, as opposed to a non-transepithelial skin surface approach such as disclosed in U.S. Pat. Nos. 6,351,666; 5,678,547; 4,955,383. When a tumor develops in a region of up-regulated proliferation, the overlying breast skin becomes further depolarized compared with other regions of the breast and the impedance of the cancerous breast tissue decreases. The changes in ductal epithelial impedance are not measured using existing technologies resulting in a diminution in accuracy. Alterations in TEP and impedance occur under the influence of hormones and menstrual cycle.

For example, the electrophysiological response of breast tissue to 17-β-estradiol has been observed to be different in pre-cancerous or cancerous epithelium than in normal breast epithelium. In one method of the present invention, estradiol is introduced directly into the duct or systemically following sublingual administration of 17-β-estradiol (4 mg). This agent produces a rapid response, which peaks at approximately 20 minutes. The electrophysiological response depends, in part, on the stage of the patient's menstrual cycle, as well as the condition of the breast tissue. Specifically, in normal breast tissue, a rise in TEP will occur during the follicular (or early) phase. In pre-cancerous or cancerous tissue, this response is abrogated. Post-menopausal women at risk for breast cancer may have an exaggerated TEP response to estradiol because of up-regulated estrogen receptors on epithelial cell surfaces.

Furthermore, estrogen, progesterone, prolactin, corticosteroids, tamoxifen or metabolites, (all of which alter the ion transport characteristics of ductal epithelium depending on its premalignant, malignant and functional state), thereof may be introduced either orally, intravenously, transcutaneously, or by intraductal installation.

In one embodiment of the present invention, breast or other cancers may be diagnosed by examining the basal conductance state of the paracellular pathway of the epithelium. For example, in the breast, a substance known to affect the conductance of the tight junctions may be infused into the duct, or administered by other mean, and the transepithelial impedance and/or the DC potential of the breast is measured, before and after the administration of the agent, using a combination of surface, nipple, ductal or other electrodes. The difference in the transepithelial electrical response of the tight junctions to the agent in normal compared to pre-malignant or malignant breast epithelium is then is used to diagnose the presence or absence of malignancy.

In another embodiment, the electrodes are placed over the suspicious region and the passive DC potential is measured. Then AC impedance measurements are made as discussed below. The variable impedance properties of the overlying skin may attenuate or increase the measured DC surface electropotentials. Alternatively, impedance measurements at different frequencies may initially include a superimposed continuous sine wave on top of an applied DC voltage. Phase, DC voltage and AC voltage will be measured. The resistance of the skin or other epithelium at AC and a different resistance at DC are measured. Under DC conditions since there is no phase shift, it is possible to measure the transepithelial potential at the surface. The capacitive properties of the skin may allow the underlying breast epithelial and tumor potential to be measured at the skin surface.

Once the ECM results in "wetting" of the skin surface there is pseudo-exponential decay in the skin surface potential using the above referenced approach. Ions in the ECM diffuse through the skin and make it more conductive, particularly because of changes in the skin parallel resistance. The time constant for this decay is inversely proportional to the concentration and ionic strength of the gel. Once the skin is rendered more conductive by the ECM the capacitive coupling of the surface to the underlying potential of the tumor or the surrounding epithelium is lost so that the measured potential now reflects an offset and diffusion potential at the electrode-ECM-skin interfaces.

Figure 6:
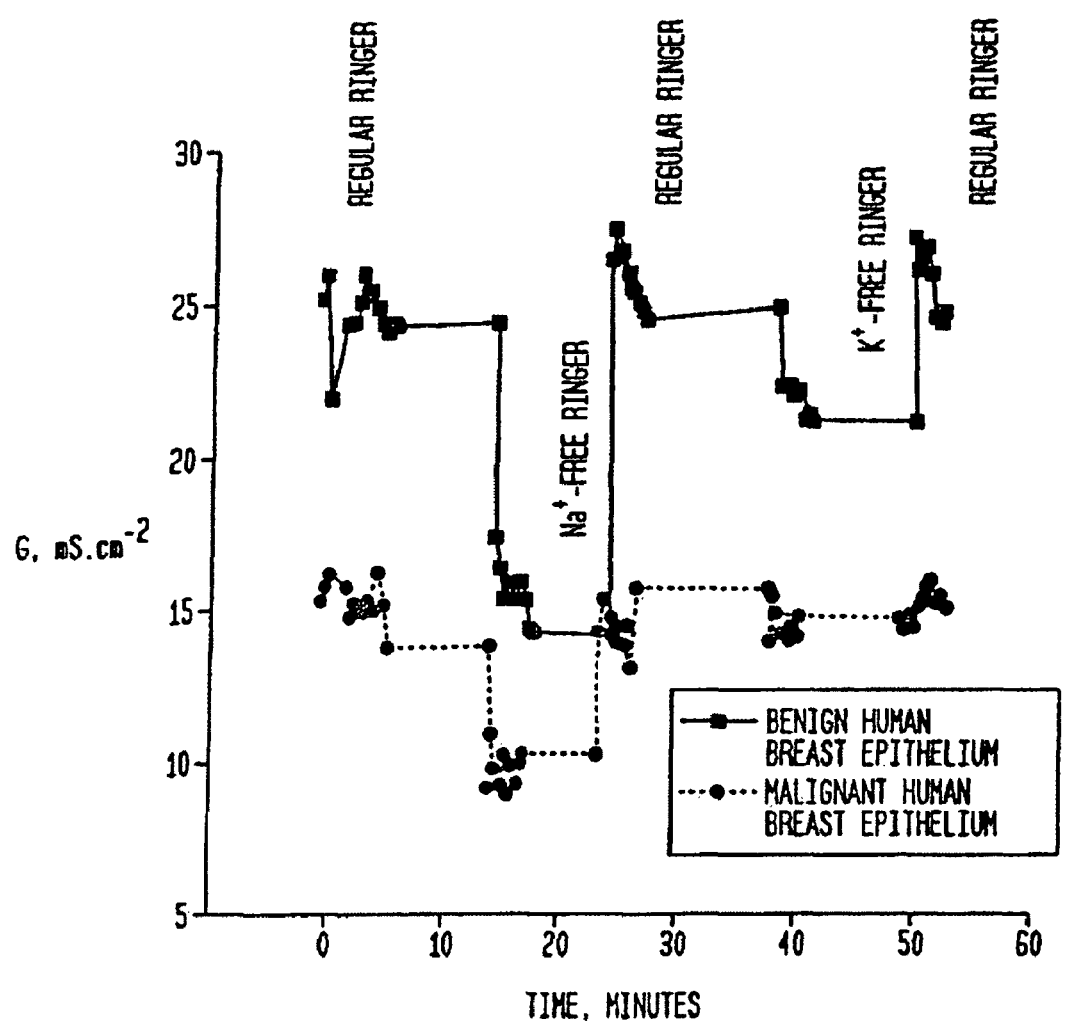
FIG. 6 illustrates varying ionic content and the effect on transepithelial conductance in human breast epithelium.

FIG. 6 demonstrates the effect of varying the ionic content of the bathing Ringers solution on transepithelial conductance. The human breast epithelial cells were grown as monolayers on Millipore filters and grew to confluence in 7 to 10 days. The epithelia were then mounted in modified Ussing chambers and the DC conductances were measured using a voltage clamp. The conductance was measured by passing a 2 µA current pulse for 200 milliseconds and measuring the DC voltage response and calculating the transepithelial conductance (y-axis), and plotting it against time (x-axis). The conductance was measured first in standard Ringer solution, then in a sodium-free Ringer, then returned to standard Ringer, then in a potassium-free Ringer and finally returning to standard Ringer solution while maintaining normal osmolality during the studies.

The upper plot (filled squares and solid line) demonstrates the conductance of benign human breast epithelia grown as a monolayer. The conductance is higher in the benign epithelial cells. The $Na^+$ and $K^+$ components of conductance are approximately, 10 and 5 $mS \cdot cm^{-2}$ respectively.

The lower plot (filled circles and dotted line) demonstrates the conductance of malignant human breast epithelia grown as a monolayer. The conductance is significantly lower in the malignant epithelial cells. The $Na^+$ and $K^+$ components of conductance are approximately, 4 and 1 $mS \cdot cm^2$ respectively.

In malignant tumors as opposed to monolayers of malignant epithelial cells, the tight junction between cells break down and the tumor becomes more conductive than either benign or malignant epithelial monolayers. This observation may be exploited in the diagnosis of breast cancer. The lower conductance of the epithelium around a developing tumor, together with a region of high conductance at the site of the malignancy, may be used to more accurately diagnose breast cancer. Using electrodes with ECMs with different ionic composition will permit the specific ionic conductances to be used in cancer diagnosis. For example a high conductance region with a surrounding area of low K-conductance is indicative of breast cancer; a high conductance area with a surrounding region of normal conductance may be more indicative of fibrocystic disease (a benign process).

Figure 7:
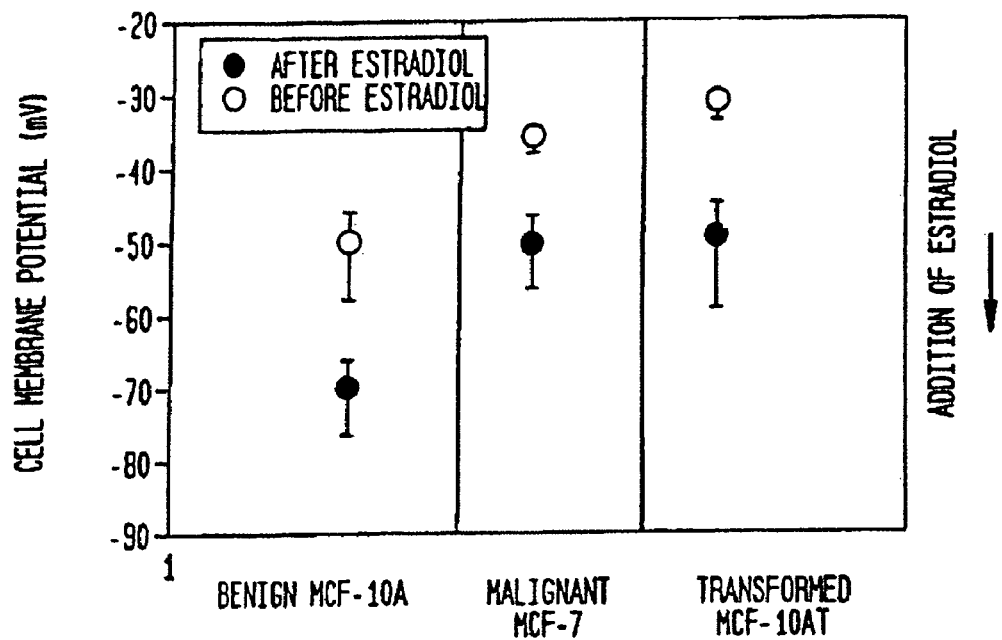
FIG. 7 illustrates measurements of cell membrane potential in human breast epithelial cells.

FIG. 7 demonstrates measurements of cell membrane potential ($\psi$) in human breast epithelial cells. Measurements were made using a potentiometric fluorescent probe, and ratiometric measurements, which are calibrated using valinomycin and $[K^+]$-gradients. $\psi$s were measured in the presence (closed circles) and absence (open circles) of estradiol (the active metabolite of estrogen). Each symbol is the mean measurement. The upper error bar is the standard error of the mean, and the lower error bar is the 95% confidence level for the observations. The addition of estrogen to cultured breast epithelial cells results in an instantaneous increase in $\psi$ (data not shown) as well as the transepithelial potential see FIG. 8. Transepithelial potential ($V_T$) of an epithelium is the sum of the apical (luminal) cell membrane potential ($V_A$) and the basolateral (abluminal) cell membrane potential ($V_{BL}$). Therefore $V_T = V_A + V_{BL}$ (changes in $V_A$ and/or $V_{BL}$ will therefore alter $V_T$ or transepithelial potential).

FIG. 7 demonstrates that benign breast epithelial cells have a $\psi$ of approximately −50 mV in the absence of estradiol and −70 mV when estradiol is added to the culture media. Malignant and transformed cells have a $\psi$ of between −31 and −35 mV in the absence of estradiol and approximately 50 mV when estradiol is present in the culture medium.

The difference in the electrical properties may be exploited to diagnose breast cancer in vivo. Surface electropotential measurements are a combination of the transepithelial potential, tumor potential and overlying skin potential. Physiological doses of estradiol may be administered to the patient to increase $\psi$ and the sustained effect of estradiol results in an increase in transepithelial potential and tumor potential measured as an increase in surface electropotential. The increase following sustained exposure (as opposed to the instantaneous response) is less in malignant than benign breast tissue.

Figure 8:
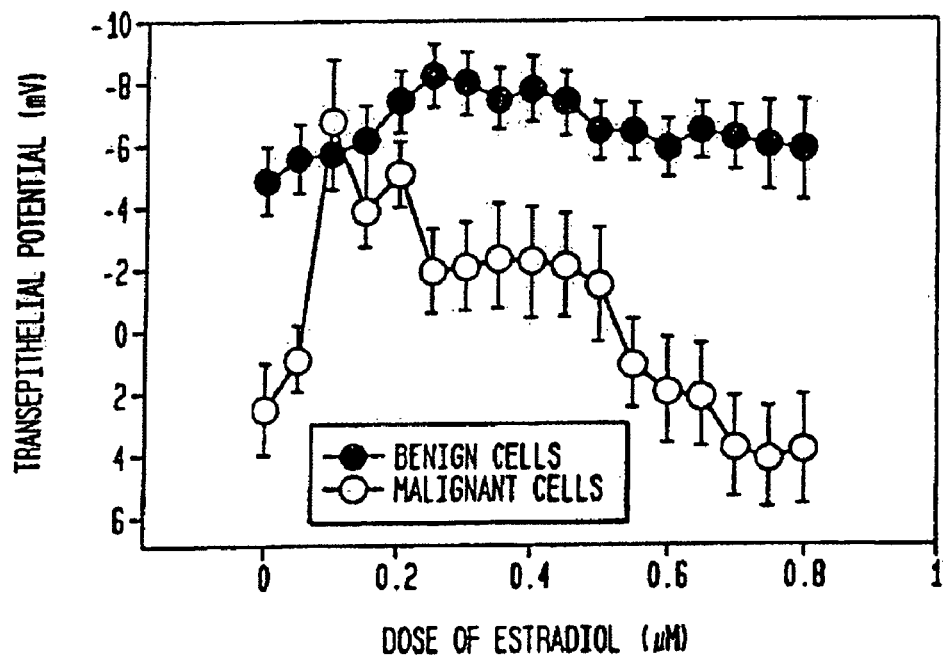
FIG. 8 illustrates the effect of increasing estradiol concentrations on the transepithelial potential in benign and malignant breast epithelia.

It should be noted that the instantaneous response, illustrated in FIG. 8, is greater in malignant epithelia, whereas the chronic or sustained exposure to estradiol results in a lower increase in TEP (transepithelial electropotential) in malignant cells. Concurrent measurement of surface electropotential and impedance allow the more accurate diagnosis of cancer. FIG. 8 demonstrates the instantaneous effect of increasing doses of estradiol on the transepithelial potential (TEP) of benign and malignant human breast epithelial cells. The cells were grown as monolayers on Millipore filters and grew to confluence in 7 to 10 days. The epithelia were then mounted in modified Ussing chambers and the TEP was measured using a voltage clamp. Increasing doses of estradiol between 0 and 0.8 µM were added (x-axis). The transepithelial potential was measured after each addition and the TEP was measured (y-axis).

The different dose response is apparent for benign and malignant epithelia. Malignant epithelia have a lower TEP but undergo an instantaneous increase in TEP of approximately 9 mV (becomes more electronegative and reaches a level of <−6 mV) after exposure to only 0.1 µM estradiol and then depolarize to approximately −2 mV with increasing doses of estradiol up to about 0.5 µM. Benign epithelia have a lesser response to increasing doses of estradiol and do not peak until almost 0.3 µM and then remain persistently elevated (higher electro negativity), unlike the malignant epithelia, with increasing doses of estradiol.

This difference in dose response may be exploited to diagnose breast cancer. Estradiol, or other estrogens, at a low dose will be administered systemically, transcutaneously, intraductally, or by other route. The instantaneous response of the surface electropotential and/or impedance may then be used to diagnose breast cancer with improved accuracy over existing diagnostic modalities using impedance or DC measurement alone.

Figure 9:
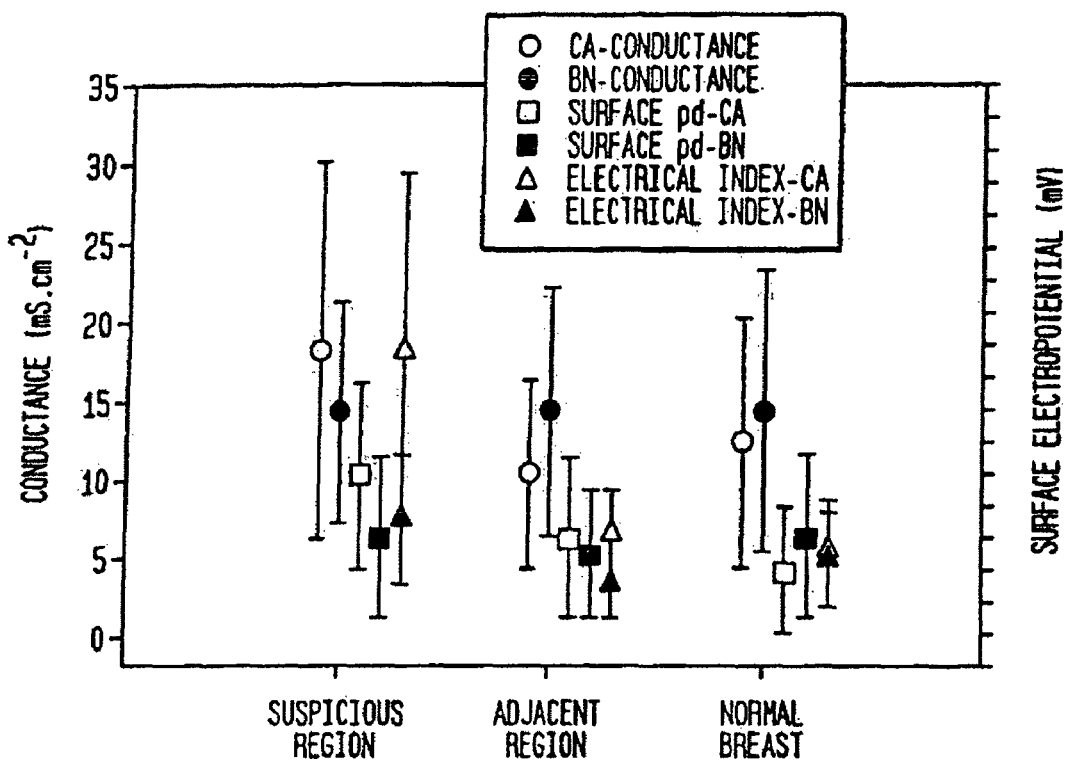
FIG. 9 illustrates conductance and the electropotential measurements made over the surface of the breast in women with and without breast cancer.

FIG. 9 shows conductance measurements made at 2000 Hz at the surface of the breast. At this frequency the influence of the overlying skin impedance is less. There is still however some variable component of skin impedance, which results in significant variability of the measurement as evidenced by the overlapping error bars. Each symbol represents the median measurement with error bars the standard deviation of the mean.

Open symbols represent measurements made in patients with a biopsy proven malignancy, while closed symbols represent measurements made in patients whose subsequent biopsy proved to be a benign process such as fibrocystic disease. Malignant lesions are often associated with surrounding breast epithelium that demonstrates Up-regulated proliferation. These regions ("adjacent region") are depolarized and may have a lower conductance than either over the region of malignancy. This decreased conductance may be because of decreased $K^+$-conductance of the adjacent and pre-malignant epithelium as I have observed in human colon.

Each of the three groups of symbols represents measurements from over a suspicious lesion or region, then the adjacent region, and then over normal breast in an uninvolved quadrant of the breast. The first two symbols (circles) in each of the three groups are impedance measurements where the median value is plotted against the left y-axis as conductance in $mS \cdot cm^{-2}$. The second two symbols (squares) is the surface electrical potential measured in mV and plotted against the right y-axis; each division equals 5 mV. The third two symbols (triangles) are the electrical index for benign and malignant lesions and are in arbitrary units and are derived from the conductance and surface potential measurement. It is immediately apparent that there is less overlap in the error bars (standard deviation of the mean). Therefore breast cancer can be more accurately diagnosed using a combination of surface potential measurement and AC-impedance measurements. Further enhancements of this technique will involve the use of spaced electrodes to probe different depths of the breast, and the use of the hormones, drugs and other agents to differentially alter the impedance and transepithelial potential from benign and malignant breast tissue, and measured at the skin or duct surface. This will enable further improvements in diagnostic accuracy.

Figure 10:
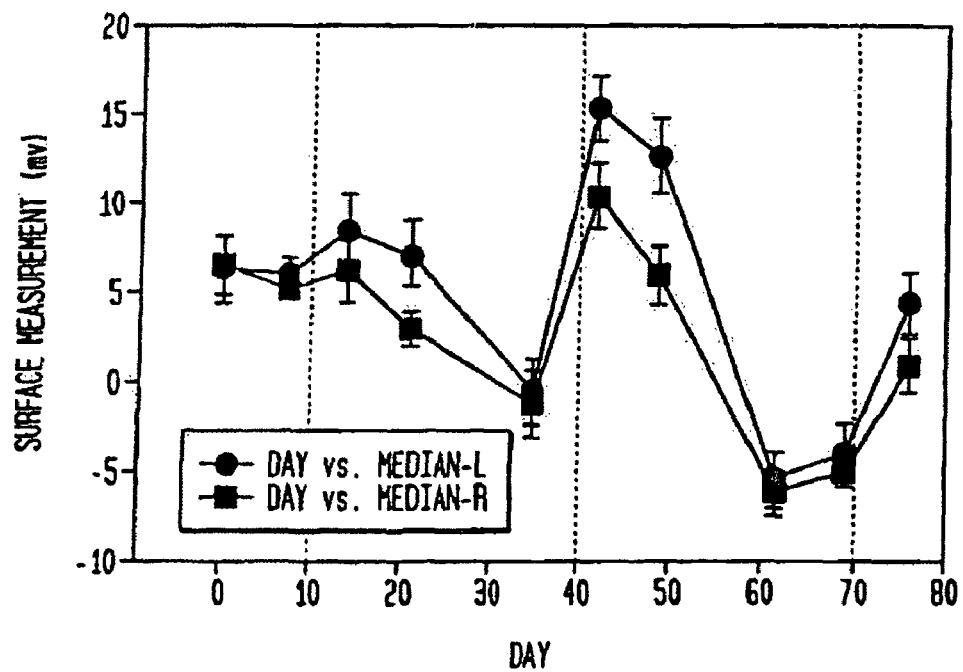
FIG. 10 illustrates the measurement of electropotentials at the surface of the breast, and variation of the measurement during menstrual cycle.

It should be understood that the surface potential measurement of breast tissue varies based on the position of the woman in her menstrual cycle. FIG. 10 illustrates this variance. This figure demonstrates electropotential measurements taken over the surface of each breast at 8 different locations with an array of 8 electrodes on each breast referenced to an electrode on the skin of the upper abdomen. Measurements are taken with error bars equal to the standard error of the mean. Filled circles and filled squares represent the median value from the left and right breast respectively. The vertical dotted line is the first day of each menstrual cycle.

It can be seen that the median values for each breast tend to track one another with lower values in the first half of menstrual cycle (follicular phase) and higher values in the latter part of cycle (luteal phase). Although the measured electrical values are not completely superimposed, because of other factors affecting the electropotential of the breast, it can be seen that the lowest levels of electropotential are observed 8-10 days before menstruation and the rise to the highest levels around the time of menstruation. This may be because estradiol levels are higher in the second part of menstrual cycle and directly affect breast surface electropotential.

The cyclical pattern of electropotential activity when a breast cancer or proliferative lesion is present is quite different. Similarly higher levels of surface electropotential are observed when measurements were made in the afternoon compared with the morning. This information can be exploited in a number of different ways. Measurement of the surface potential and impedance at different times during cycle enables a more accurate diagnosis because of a different cyclical change in surface electropotential (i.e., the peak to peak change in potential is less over a malignant region, relative to normal areas of the breast). Secondly, estradiol or another agent that changes the electropotential of the breast may be administered systemically, topically (transdermal), intraductally or by other means, and the drug or hormone-induced change in surface potential may be used as a provocative test to diagnose breast cancer.

Figure 11:
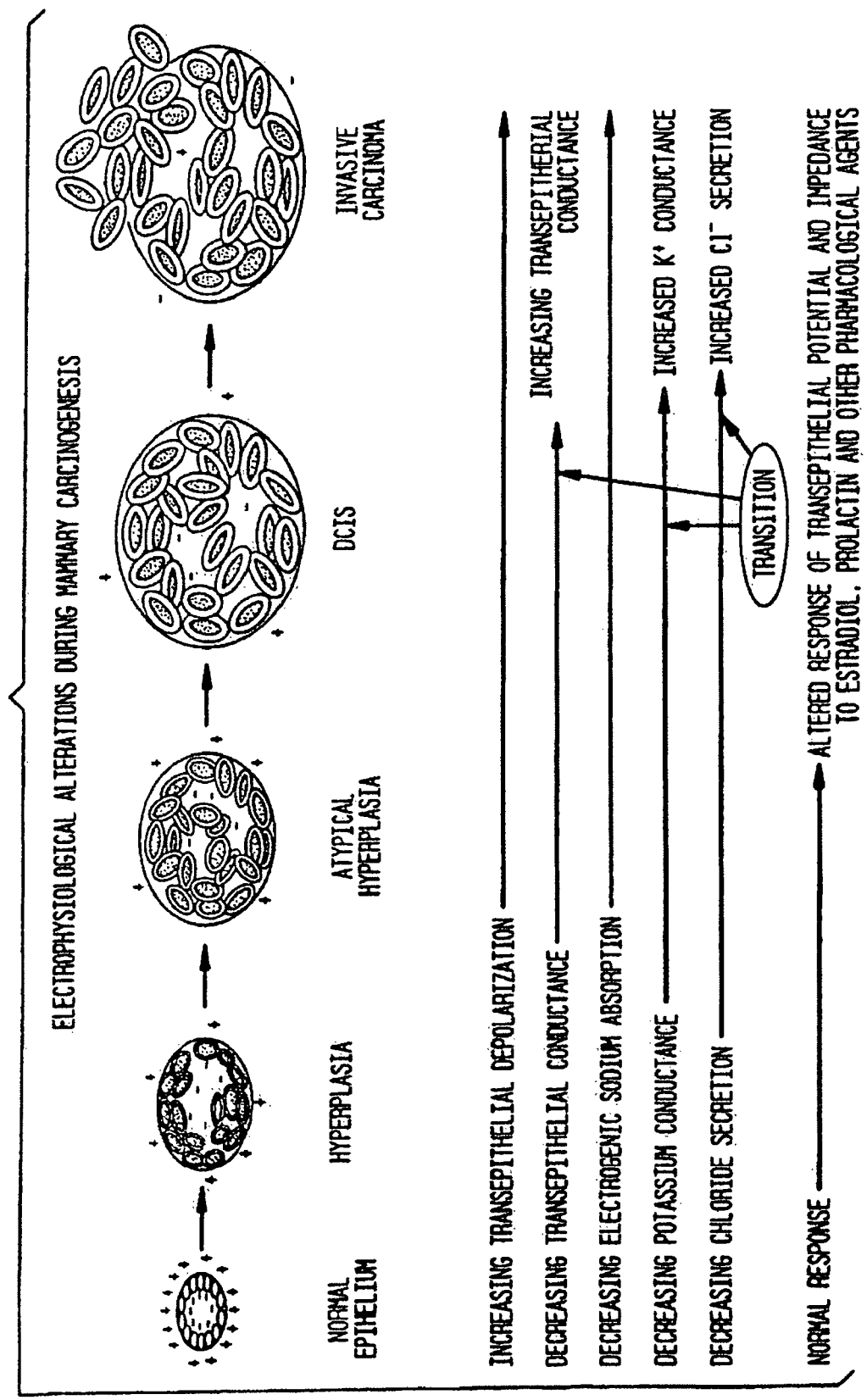
FIG. 11 illustrates electrophysiological changes that occur within the ductal epithelium during the development of breast cancer.

FIG. 11 is a diagram illustrating the histological and electrophysiological changes that occur during the development of breast cancer. The continuum from normal ductal epithelium, through hyperplasia, atypical hyperplasia, ductal carcinoma in situ (DCIS), to invasive breast cancer is thought to take 10 to 15 years. Some of the steps may be skipped although usually a breast cancer develops within a background of disordered ductal proliferation. The normal duct maintains a transepithelial potential (inside of duct negatively charged), which depolarizes and impedance, which increases during the development of cancer. Once an invasive breast cancer develops the impedance decreases with loss of tight junction integrity, and conductance through the tumor is enhanced. The disordered ducts have altered electrophysiogical and ion transport properties. These properties are illustrated in the lower aspect of FIG. 11. These electrophysiological and transport alterations will be exploited to diagnose cancer and premalignant changes in the breast.

In these ways breast cancer can be more accurately diagnosed using transepithelial measurements of potential, or impedance, or a combination of transepithelial surface potential measurement, AC-impedance measurements and pharmacological manipulations.

Example 2

Chemopreventative and Therapeutic Use

In addition to the ionic, pharmacologic, and hormonal agents described above, the system and method of the present invention may be used with cancer preventative and therapeutic agents and treatments. Specifically, electrical measurement of altered structure and function provides a method for evaluating a patient's response to the drugs without requiring a biopsy and without waiting for the cancer to further develop. Patients who respond to a given chemopreventative or therapeutic agent would likely show restoration of epithelial function to a more normal state. Patients who do not respond would show minimal change or may even demonstrate progression to a more advanced stage of the disease. This system and method, thus, may be used by either clinicians or drug companies in assessing drug response or by clinicians in monitoring the progress of a patient's disease and treatment, or monitoring the process of carcinogenesis (cancer development), before an overt malignancy has fully developed.

Example 3

Electrophysiological Changes in Other Epithelia

Figure 12:
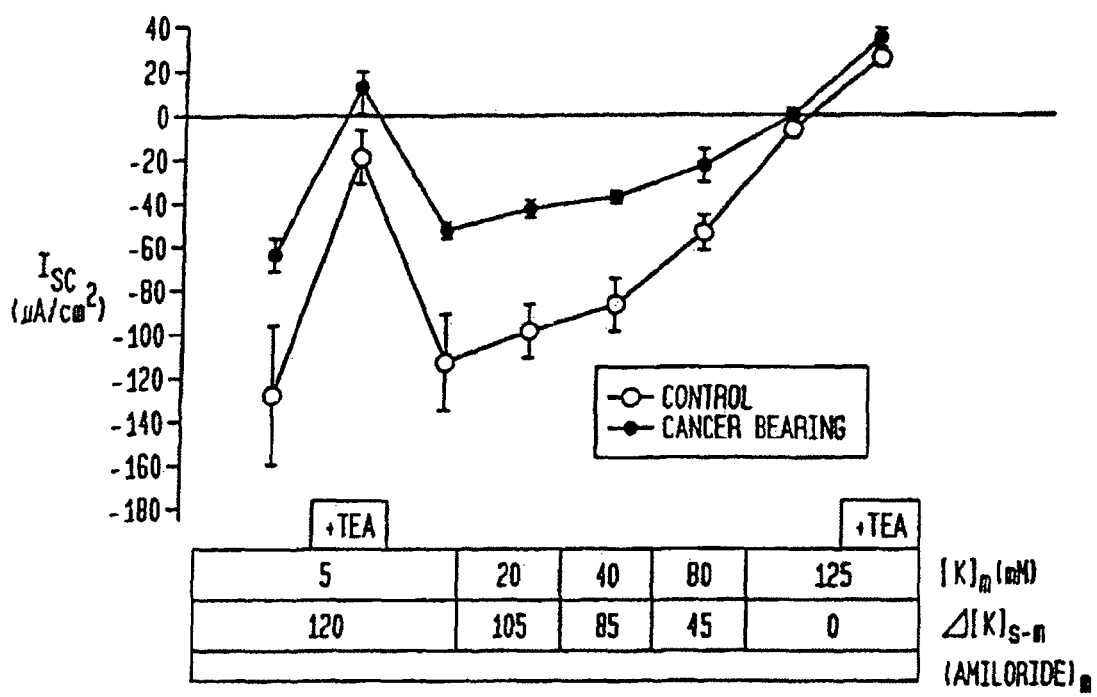
FIG. 12 illustrates changes in the short circuit current of human epithelium exposed to a potassium channel blocker (TEA) or varying concentrations of potassium.
Figure 13:
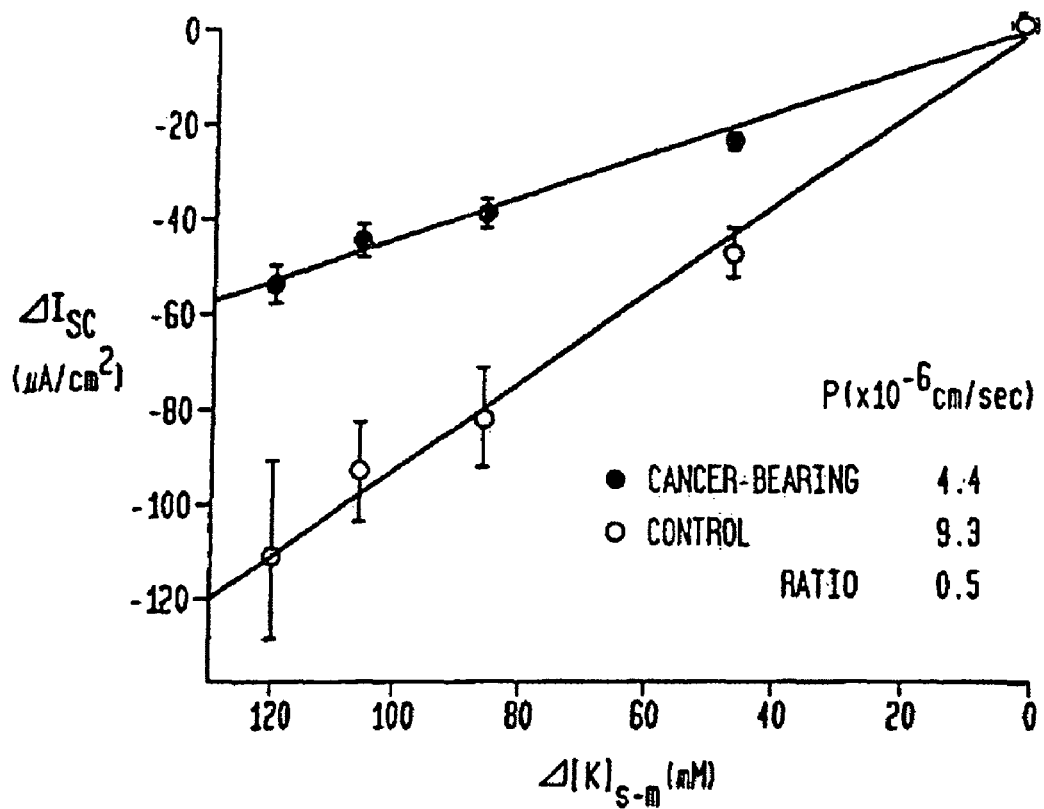
FIG. 13 illustrates how the information obtained in FIG. 12 may be used to plot the potassium gradient against the change in short circuit current.

The examples illustrated by FIGS. 12 and 13 were performed in human colon specimen removed at the time of surgery. Based on in vitro studies in breast epithelial tissues, similar changes in human ductal epithelium that can be measured in vivo are expected.

FIG. 12 demonstrates the short circuit current ($I_{SC}$) of human colonic epithelium ex-vivo. The figure demonstrates the time course along the x-axis while varying the potassium gradient across the tissue. The potassium permeability of the apical membrane of human colonic mucosa ($P^K_a$) was determined in surgical specimens of controls and grossly normal-appearing mucosa obtained 10-30 cm proximal to colorectal adenocarcinomas. The mucosa was mounted in Ussing chambers and the basolateral membrane resistance and voltage were nullified by elevating the $K^+$ in the serosal bathing solution. The apical sodium ($Na^+$) conductance was blocked with 0.1 mM amiloride. This protocol reduces the equivalent circuit model of the epithelium to an apical membrane conductance and electromotive force in parallel with the paracellular pathway as has been verified by microelectrode studies. Increasing serosal $K^+$ caused the $I_{sc}$ to become negative (−140 μA/cm²) in normal colon after which 30 mM mucosal TEA caused an abrupt increase in $I_{sc}$ corresponding to block of apical $K^+$ channels. In cancer-bearing colon the reduction in $I_{sc}$ is to −65 μA/cm². The serosal bath was remained constant at 125 mM [K].

FIG. 13 demonstrates that $\Delta I_{sc}$, determined with respect to the $I_{sc}$ at 125 mM mucosal K, is a linear function of the concentration gradient, Δ[K]. Because the voltage across the apical membrane is zero under these conditions and the paracellular pathway is nonselective, the $P^K_a$ (apical potassium permeability) can be calculated using the Fick equation i.e., $I_{sc}=F \cdot P^K_a \cdot \Delta[K]$ where F is the Faraday constant and Δ[K] is the concentration difference for $K^+$ across the epithelium. FIG. 13 demonstrates mean±sem values for $I_{sc}$ in both normal and premalignant human distal colon. The apical $K^+$ permeability of controls was $9.34 \times 10^{-6}$ cm/sec and this was significantly reduced by 50% in premalignant human mucosa to $4.45 \times 10^{-6}$ cm/sec. $P^K_a$ could also be calculated for the change in $I_{sc}$ when the $K^+$ channels were blocked with TEA, assuming complete block. This resulted in somewhat lower values of $6.4 \times 10^{-6}$ cm/sec and $3.8 \times 10^{-6}$ cm/sec corresponding to a 40% reduction in $P^K_a$.

These observations show that there is a field change in the $K^+$ permeability and conductance of human colon, during the development of cancer. Similar results are expected in breast ductal epithelium. Impedance measurements, and/or DC measurement using electrodes with different potassium gradients together with specific drugs, such as amiloride to block the contributions, of electrogenic $Na^+$ transport; to the electrical properties of the breast may be useful to diagnose breast cancer. Amiloride may be introduced through the breast duct and then the $K^+$-concentration varied in the ECM used in the nipple electrode or irrigated into the duct to measure the reduced potassium permeability observed in the surrounding breast ductal epithelium (with atypical ductal hyperplasia or early DCIS), or increased permeability in the region of the developing invasive breast cancer.

Figure 14:
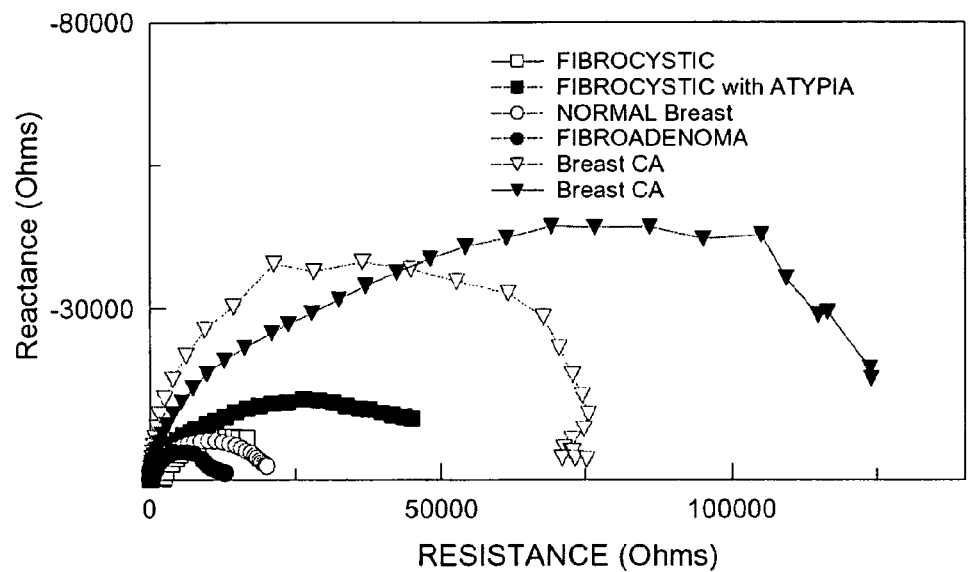
FIG. 14 illustrates multiple Nyquist impedance plots from human breasts according to the present invention.

FIG. 14 illustrates multiple Nyquist impedance plots from human breasts. Current was passed between a nipple cup electrode containing a physiological saline solution under suction to open up the breast ducts on the surface of the nipple, and an electrode placed on the surface of the breast. Voltage was then measured between the nipple and the region of interest using a separate set of voltage measuring electrodes. All measurements were made at 59 frequencies logarithmically spaced between 60,000 hertz and 1 hertz except for the fibrocystic with atypia case (filled squares), which was measured at 59 frequencies between 60,000 hertz and 0.1 hertz. The impedance curves demonstrate the lowest impedance at highest frequencies. As the frequency of the applied sine wave decreases the curves shift from left to right along the x-axis.

Figure 15:
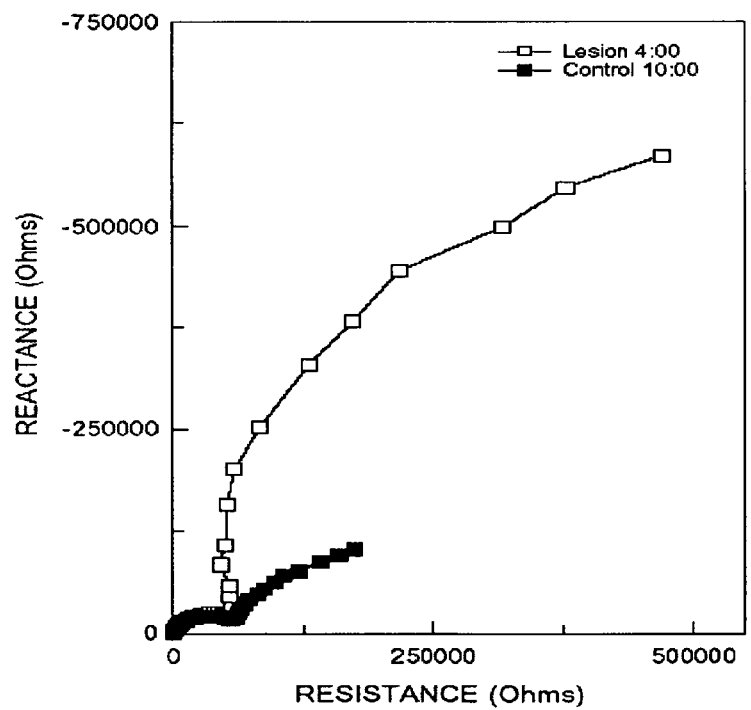
FIG. 15 illustrates the impedance profile for a patient with a hemorrhagic cyst.

FIG. 15 illustrates the impedance profile for a patient with a hemorrhagic cyst. These studies were performed at frequencies from 60,000 hertz to 0.1 hertz. Measurements were made over the mass (lesion) in the 4 o'clock location of the breast and control measurements were made in the 10 o'clock location of the same breast. The high frequency measurement demonstrates that the curves were superimposable. Separation begins at a frequency below 5 Hz. The resistance of the mass was higher than the control quadrant of the breast at low frequencies. Surface open circuit potential measurements showed depolarization of only 2 mV over the mass and therefore enabled discrimination from cancer despite the high impedance.

FIG. 16 illustrates a Bode plot of impedance plots comparing a patient with fibrocystic disease (0465) and a patient with breast cancer ((0099). It can be seen that the impedance [Z] and, theta (phase angle) separate at the lowest frequencies (open and closed symbols). The data for the suspicious mass, which was identified as fibrocystic disease on pathology, the control region and the control region from the breast cancer are almost superimposable. At the low frequency end of the spectrum the cancer (0099D-filled circles) separates from the control quadrant measurement (0099C-open circles) at approximately 20 Hz.

Figure 17:
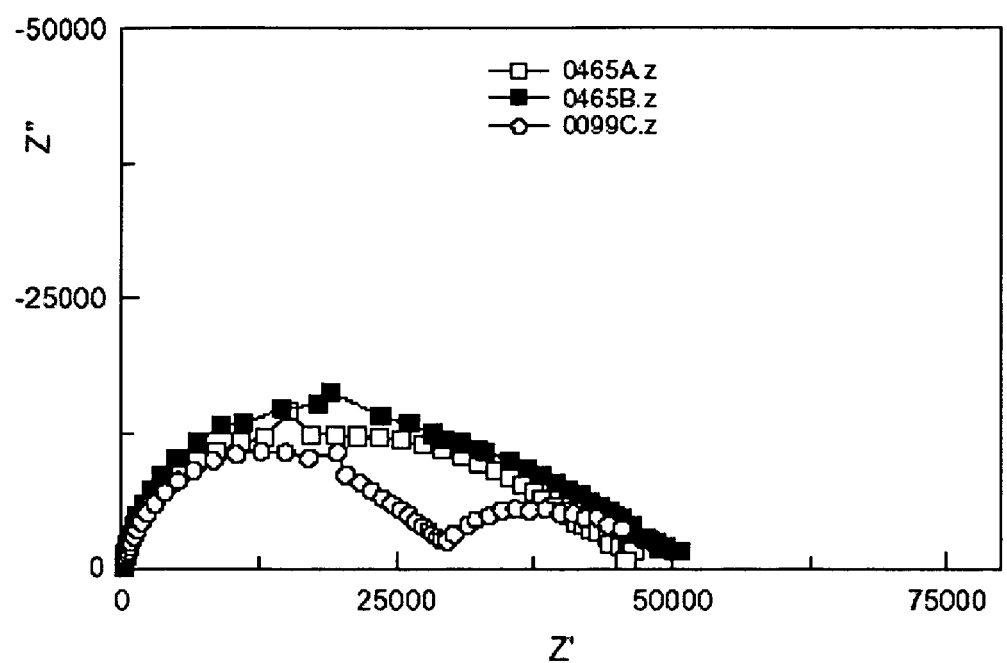
FIG. 17 illustrates the same data as in FIG. 16 plotted as a Nyquist plot.

FIG. 17 illustrates the same data as in FIG. 16 plotted as a Nyquist plot. The mass (a region of fibrocystic disease 0465A-open squares) has a 5000Ω lower impedance at the low frequency end of the curve to the right side of the x-axis, compared with the control region (0465B filled squares). Plot 0099C (open circles) has a similar total impedance to the breast with fibrocystic changes but the curve shows a "double hump" indicating two different time constants (τ) for the low and high frequency ends of the impedance spectra in the malignant breast. This characteristic appearance can also be utilized as a diagnostic tool.

Figure 18:
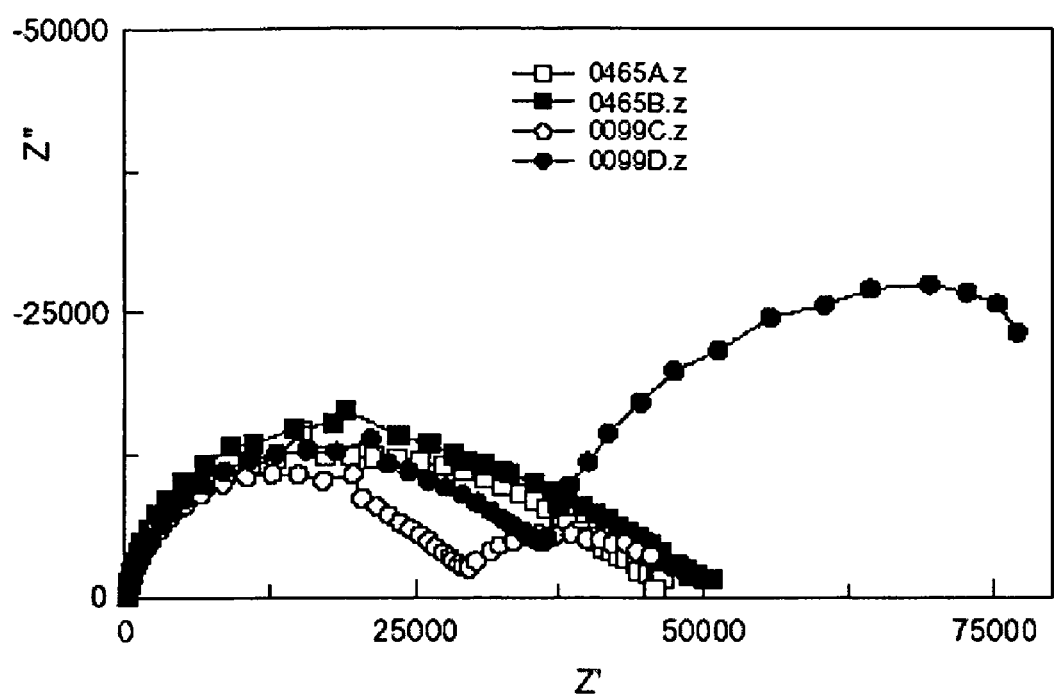
FIG. 18 illustrates the impedance spectra data curve for breast cancer tissue added to the curves of FIG. 17.

FIG. 18 demonstrates the impedance spectra when the curve (0099D-filled circles) is added for the breast cancer to FIG. 17. The total impedance is significantly higher at 76397$\Omega$ compared to 45447$\Omega$ for the control quadrant, and the lower (high frequency) curves begin to separate below about 200 Hz. The cancer was depolarized by 26 mV compared with the control quadrant, and the fibrocystic disease was depolarized by 5.5 mV. The combination of higher impedance and greater depolarization enabled diagnosis of breast cancer in one patient and fibrocystic disease in the other despite the fibrocystic patient having impedances close to 50,000$\Omega$, a high value typically, but not necessarily suggesting the presence of cancer.

Figure 19:
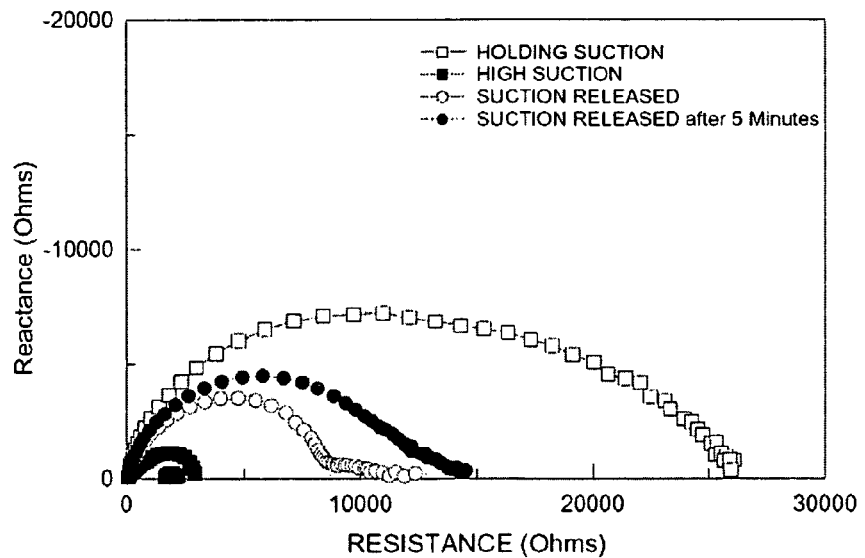
FIG. 19 illustrates the effects of altering the level of suction applied to a nipple cup electrode on a normal breast.

FIG. 19 illustrates the effects of altering the level of suction applied to the nipple cup electrode. Holding suction was established where 3 ml of saline was aspirated from the nipple cup and is illustrated as the impedance curve with open squares. The impedance is approximately 26,000$\Omega$. When an additional 2-3 ml of saline is aspirated from the nipple cup electrode the impedance curve collapses to an impedance of approximately 3000$\Omega$-filled squares. The addition of 1-2 ml of saline resulted in an increase in impedance (open circles), which increased to approximately 15000$\Omega$ after 5 minutes (closed circles).

Figure 20:
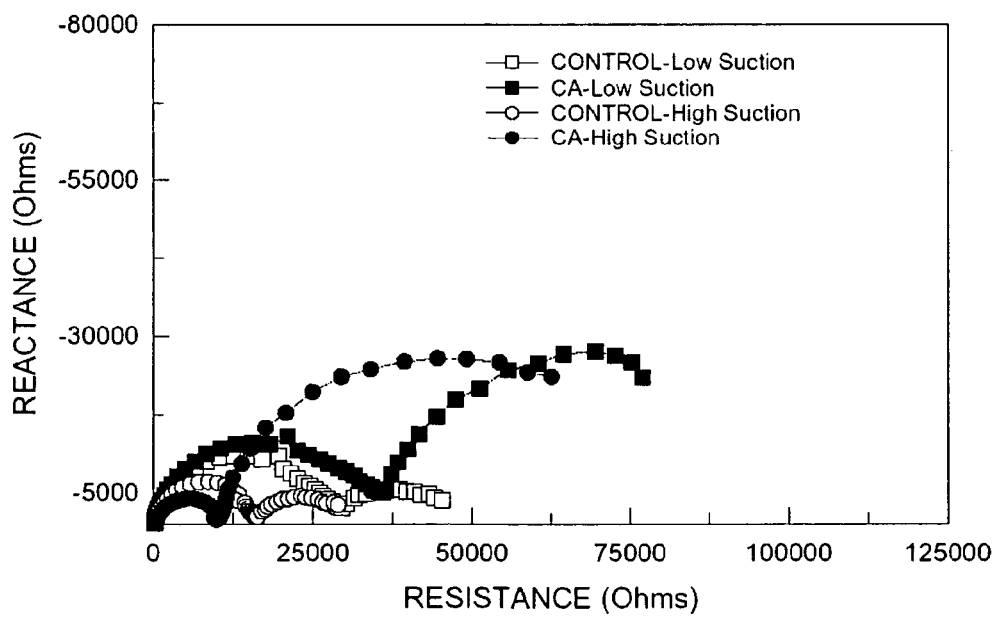
FIG. 20 illustrates the effects of altering the level of suction applied to a nipple cup electrode on a breast in which malignancy is present.

FIG. 20 illustrates similar suction pressure experiments on a malignant breast: aspirating 3 ml of physiological saline from the nipple electrode, after holding suction is obtained, results in a decrease in total impedance from 45,447$\Omega$ to 29,029$\Omega$ in the control quadrant whereas impedance decreases from 76,937$\Omega$ to 62,568$\Omega$ over the cancer. The greatest decrease in impedance is seen at the high frequency end of the impedance spectra (curves on the left side of the X-axis). For example, the impedance decreases from 29216 to 1550$\Omega$ in the control quadrant, and from 35824 to 10106$\Omega$ over the cancer. On the other hand, the changes in impedance are much less in the lower frequency spectra (curves on the right-side of the X-axis). A higher suction results in a decrease in impedance from 19985 to 16593$\Omega$ in the control quadrant whereas the change is even less over the cancer decreasing from 72674 to 71229$\Omega$. Capacitance increases in the control quadrant, in the low frequency range when suction is increased from 1.50E-5 to 1.76E-5F (farads), decreased from 1.17E-5 to 9.32E-6F over the cancer. It can be seen that altering the suction on the nipple cup electrode manually or with an automated suction pump can be used to distinguish malignant from benign breast epithelium by observing different responses of the impedance spectra to this maneuver.

Figure 21:
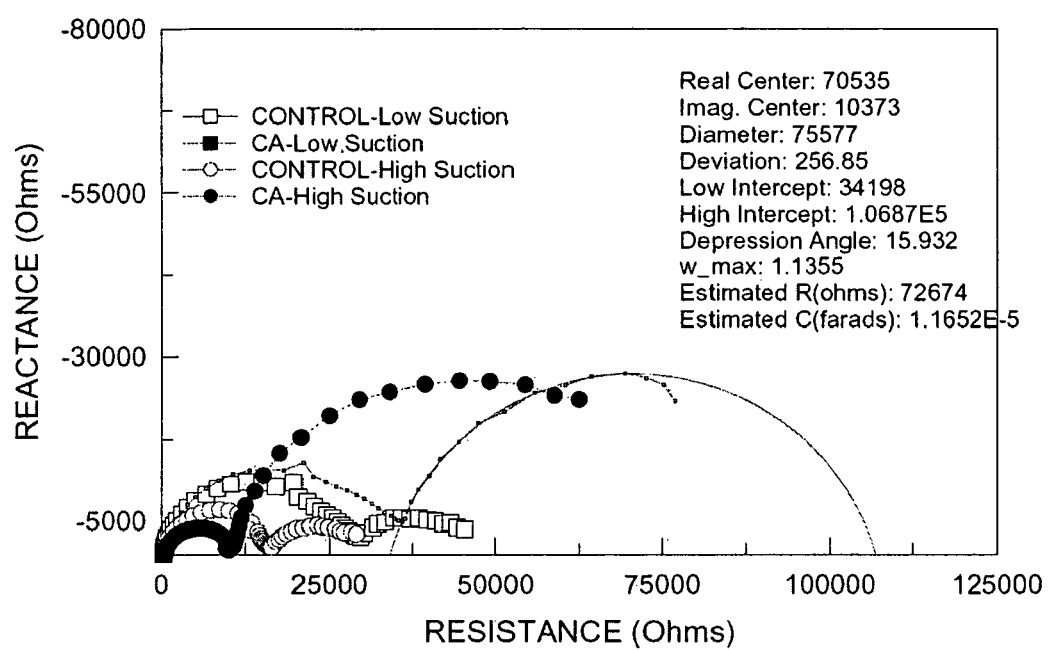
FIG. 21 illustrates the method for estimating impedance for the high suction curve associated with cancer in FIG. 20.

FIG. 21 illustrates the method used for estimating the impedance for the cancer high suction curve in FIG. 20, where an arc is fitted to the impedance data and extrapolated to the x-axis at each end of the curve. The difference between the low and high intercepts is the estimated resistance of 72674$\Omega$. The Capacitance (C) is estimated from the reactance at the maximum height of the arc, and is 1.1652E-5. The Depression Angle (15.932) is the angle between the x-axis and a line drawn from the origin of the x-axis to the center of the plotted arc.

DEVICES FOR USE WITH THE PRESENT INVENTION

A number of variations are possible for devices to be used with the present invention. Further, as noted above, within a device design, there are a number of aspects that may be varied. These variations, and others, are described below.

One embodiment of a probe or other device for use in the present invention includes a plurality of miniaturized electrodes in recessed wells. Surface recording and initial electronic processing, such as filtering, may be performed by disposable commercially-available silicon chips. Each ECM solution or agent may be specific to the individual electrode and reservoir on the chip. Thus, for one measurement, a particular set of electrodes would be used. For another measurement, for example, at a different ionic concentration, a different set of electrodes would be used. While this produces some variations, as the electrodes for one measurement are not located at the same points as for another, this system provides generally reliable results.

An alternative approach is to use fewer electrodes and use a flow-through or microfluidic system to change solutions and drugs. Specifically, solutions or agents are changed by passing small amounts of electrical current to move solution or agent through channels and out through pores in the surface of the device. In this embodiment, the electrode remains in contact with the same region of the surface of the breast, thus eliminating region-to-region variation in measurement. This approach requires time for equilibration between different solutions. In detecting the presence of abnormal pre-cancerous or cancerous breast tissue, a hand-held probe is provided for obtaining surface measurements at the skin. The probe may include electrodes for passing current as well as for measuring. An impedance measurement may be taken between the nipple cup electrode and the hand-held probe, between a nipple cup electrode and adhesive skin electrodes, between electrodes on a miniature ductoscope, between electrodes on a ductoscope and the skin surface electrodes, or may be taken between electrodes on the hand-held probe. After taking initial DC measurements, a wetting/permeabilizing agent may be introduced to reduce skin impedance. The agent may be introduced using a microfluidic approach, as described above, to move fluid to the surface of the electrodes. Alternatively, surface electrodes that just penetrate the stratum corneum may be used to decrease impedance.

Fluids for use with the present inventions could include various electrolyte solutions such as physiologic saline (e.g. Ringers) with or without pharmacological agents one preferable electrolyte solution to infuse into the ductal system will represent a physiological Ringer solution. Typically this consists of NaCl 6 g, KCl 0.075 g, $CaCl_2$ 0.1 g, $NaHCO_3$ 0.1 g, and smaller concentrations of sodium hyper and hypophosphate at a physiological pH of 7.4. Other electrolyte solution may be used were the electrolyte comprises approximately 1% of the volume of the solute. Hypertonic or hypotonic solutions that are greater or less than 1% may be used in provocative testing of the epithelium and/or tumor. The concentration of Na, K and Cl will be adjusted under different conditions to evaluate the conductance and permeability of the epithelium. Different pharmacological agents such as amiloride (to block electrogenic sodium absorption), Forskolin (or similar drugs to raise cyclic-AMP) and hormones such as prolactin or estradiol can also be infused with the Ringer solution to examine the electrophysiological response of the epithelium and tumor to these agents. Similarly, the calcium concentration of the infusate will be varied to alter the tight junction permeability and measure the electrophysiological response of the epithelium to this manipulation. Dexamethasone may be infused to decrease the permeability of the tight junctions, and the electrophysiological response will be measured.

Although specific examples have been given of drugs and hormones that may be used in "challenge" testing of the epithelium and tumor, any agonist or antagonist of specific ionic transport, or tight-junctional integrity, known to be affected during carcinogenesis may be used, particularly when it is known to influence the electrophysiological properties of the epithelium or tumor.

Regardless of the configuration of the device, a signal is used to measure either the ductal transepithelial potential by itself, or the transepithelial impedance. These two measurements may then be combined to characterize the electrical properties of the epithelium associated with a developing abnormality of the breast, and are then compared with uninvolved areas of the same or opposite breast. Surface electropotential measurements and impedance measurements are then made to characterize the non-transepithelial electrical properties of the breast. These measurements involve DC potential measurements where the surface potential is referenced to an electrode that is not in contact directly, or indirectly through an ECM, with the duct lumen. Impedance measurements are similarly made between surface electrodes or a surface electrode and a reference electrode not in contact directly or indirectly (through an ECM) with the ductal lumen. These measurements are then compared and combined with the transepithelial electrical measurements to further characterize the breast tissue.

Furthermore an understanding of the electrophysiological basis of the altered impedance or DC potential permits more accurate diagnosis. For example impedance or DC potential may increase or decrease because of several factors. Increased stromal density of the breast may alter its impedance. This is a non-specific change, which may not have bearing on the probability of malignancy. On the other hand, a decrease in the potassium permeability of the epithelia around a developing malignancy would increase impedance and would be more likely associated with a developing cancer than a non-specific impedance change. Additional information is obtained from my method by probing the tissue to different depths using spaced voltage-sensing electrodes. The use of electrophysiological, pharmacological and hormonal manipulations to alter DC potential and/or DC potential differentially in normal compared to cancer-prone, pre-malignant or malignant tissue is another significant difference, which enhances the diagnostic accuracy of my invention over the above referenced ones.

Although the use of a nipple cup electrode has been described in this application for use in breast cancer diagnosis, a cup electrode may be used in other organs where the epithelium may be difficult to access endoscopically, or an endoscopic approach is not desired. An example would be the pancreatic and bile ducts, which join and open at the ampulla of Vater within the second part of the duodenum. Bile duct tumors develop from the endothelial lining of the bile duct, (i.e., cholangiocarcinomas, or the epithelial lining of the pancreatic duct, i.e., pancreatic carcinomas). The ampulla may be accessed endoscopically and a cup electrode applied by suction to the ampulla. Physiological saline can be infused into the ducts and then a transepithelial potential and impedance could be measured intraoperatively to identify the region of tumor in the pancreatic, or bile duct using a second electrode placed on the peritoneal surface of the pancreas or bile duct. Alternatively, the peritoneal surface electrode may be replaced by a skin surface, or intravenous electrode when used in a minimally or non-invasive manner.

Drugs may be infused though the cup electrode as a provocative test and described for breast. Secretin for example, stimulates bicarbonate secretion by the pancreatic ducts. This response may be abrogated by changes in the epithelium associated with pancreatic carcinoma. The distribution of muscarinic receptors, particularly M1 and M3, may be altered in the epithelium during pancreatic carcinogenesis. Therefore specific muscarinic agonists (cholinomimetic choline esters and natural alkaloids) and antagonists (atropine, Pirenzepine (M1), Darifenacin (M3)) may be used to elicit a particular electrophysiological response due to chloride secretion in ductal epithelium associated with pancreatic cancer. Similar approaches may be used in the intra and extrahepatic bile ducts to diagnose liver cancer.

Prostatic cancer may be diagnosed using a urethral cup electrode applied to the external urethral meatus. Physiological saline is infused into the urethra. Direct electrical connection is established with the prostatic ductal and acinar epithelium via prostatic ducts that open into the prostatic urethra. A surface electrode may then be placed per rectum onto the surface of the prostate and electrophysiological measurements may be made in a transepithelial fashion as described in the breast. Similarly, provocative tests may be performed with drugs and hormones that differentially affect the electrophysiological characteristics of abnormal prostatic epithelium when compared to normal prostatic tissue.

Endometrial cancer may be diagnosed with an electrode cup placed on the uterine cervix. Physiological saline may be infused through the cervical canal to make electrical contact with the endometrium. Electrophysiological measurements may be made with a reference electrode, placed on the skin, intravenously or at a suitable reference point. Alternatively, this approach may be used during surgery where the cervical cup electrode is used in conjunction with a reference electrode used on the peritoneal or outside surface of the uterus.

Salivary gland tumors open through small ducts into the oral cavity. For example in the parotid gland, Stensen's duct opens inside the mouth opposite the second upper molar tooth. A cup electrode may be used over the opening of the duct inside the mouth. Physiological saline is infused into the duct and electrical contact is thus established with the ductal epithelium of the salivary gland. A surface electrode is then used over the skin surface of the gland and electrical measurements are used to establish the diagnosis of cancer.

Although specific examples have been given above, this technique may be used to diagnose any tumor, where endoscopic access to the epithelium is not possible or desired. The application of physiological saline via a cup or short catheter may be used for example in the bowel or other organ system where electrical contact with the epithelium permits a transepithelial electrophysiological measurement to be made without resorting to endoscopic electrode placement. The second electrode is then used to externally scan the organ for the presence of a tumor or abnormal epithelium. Since the physiological saline acts as an electrode in direct contact with the epithelium this approach simplifies the approach to electrophysiological measurements. Depolarization and the impedance characteristics of the epithelium will be more accurate when the surface-scanning electrode is in close proximity to the underlying abnormal epithelium or tumor.

The embodiments described herein are described in reference to humans. However, cancers in non-humans may be also diagnosed with this approach and the present invention is also intended to have veterinary applications.

Any range of numbers recited in the specification hereinabove or in the paragraphs and claims hereinafter, referring to various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. Furthermore, the term "about" when used as a modifier for, or in conjunction with, a variable, characteristic or condition is intended to convey that the numbers, ranges, characteristics and conditions disclosed herein are flexible and that practice of the present invention by those skilled in the art using temperatures, frequencies, times, concentrations, amounts, contents, properties such as size, surface area, etc., that are outside of the range or different from a single value, will achieve the desired results as described in the application, namely, detecting electrophysiological changes in pre-cancerous and cancerous tissue and epithelium, for example, breast tissue.

All documents described herein are incorporated by reference herein, including any patent applications and/or testing procedures. The principles, preferred embodiments, and modes of operation of the present invention have been described in the foregoing specification.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the various aspects or embodiments of the present invention as set forth in the application and the appended claims.

The invention claimed is:

1. A method for determining a condition of a region of epithelial breast tissue comprising:
   (A) establishing a connection between a first electrode and the epithelial tissue of the nipple of a breast with a ductal probe, an electroconductive media or both;
   (B) placing a second electrode in contact with the surface of the breast;
   (C) establishing a signal between the first and second electrodes;
   (D) establishing that the nipple ducts of the breast are open by:
      (1) measuring the impedance between the first and second electrode at about 5 different frequencies in the range of about 200 Hz to about 60,000 Hz sufficient to establish an impedance curve;
      (2) treating the nipple using at least one method selected from the group consisting of (a) applying suction and release of suction to the nipple; (b) applying alcohol; and (c) applying a dekeratinizing agent;
      (3) again measuring the impedance between the first and second electrode at about 5 different frequencies in the range of about 200 Hz to about 60,000 Hz sufficient to establish an impedance curve and comparing the impedance curve obtained to that obtained in (D) (1) above;
      (4) repeating steps (2) and (3) until the impedance curve obtained in step (D) (3) is substantially unchanged in order to confirm that the ducts are open;
   (E) measuring between the first and second electrode:
      (1) a DC potential; and
      (2) impedance at about 5 different frequencies in the range of about 10 Hz to about 200 Hz and impedance at from about 5 to about 50 different frequencies in the range of about 0.1 Hz to about 10 Hz; and
   (F) determining the condition of the region of epithelial tissue based on the DC potential and impedance measurements between the first and second electrode.

2. A method for determining a condition of a region of epithelial breast tissue comprising:
   (A) placing over the nipple of a breast a cup having an interior, and first and second openings, and an electrode disposed within the interior, the cup having a source of suction in communication with the first opening, the second opening having been placed over the nipple;
   (B) establishing a connection between the electrode and the epithelial tissue of the nipple of a breast with a ductal probe, an electroconductive media or both;
   (C) placing a second electrode in contact with the surface of the breast;
   (D) establishing a signal between the first and second electrodes;
   (E) establishing that the nipple ducts of the breast are open by:
      (1) measuring the impedance between the first and second electrode at about 5 different frequencies in the range of about 200 Hz to about 60,000 Hz sufficient to establish an impedance curve;
      (2) treating the nipple using at least one method selected from the group consisting of (a) applying suction and release of suction to the nipple; (b) applying alcohol; and (c) applying a dekeratinizing agent;
      (3) again measuring the impedance between the first and second electrode at about 5 different frequencies in the range of about 200 Hz to about 60,000 Hz sufficient to establish an impedance curve and comparing the impedance curve obtained to that obtained in (D) (1) above;
      (4) repeating steps (2) and (3) until the impedance curve obtained in step (E) (3) is substantially unchanged in order to confirm that the ducts are open;
   (F) measuring a DC potential between the first and second electrode;
   (G) applying suction to the cup sufficient to effect ductal collapse in a normal or non-malignant duct; and measuring impedance at about 5 different frequencies in the range of about 10 Hz to about 200 Hz and impedance at from about 5 to about 50 different frequencies in the range of about 0.1 Hz to about 10 Hz; and
   (H) altering the suction level and again measuring impedance at about 5 different frequencies in the range of about 10 Hz to about 200 Hz and impedance at from about 5 to about 50 different frequencies in the range of about 0.1 Hz to about 10 Hz; and
   (J) determining the condition of the region of epithelial tissue based on the DC potential, and the impedance measurements under varying pressure conditions.

* * * * *

UNITED STATES PATENT AND TRADEMARK OFFICE
CERTIFICATE OF CORRECTION

| | | |
|---|---|---|
| PATENT NO. | : 7,853,319 B2 | Page 1 of 1 |
| APPLICATION NO. | : 11/409144 | |
| DATED | : December 14, 2010 | |
| INVENTOR(S) | : Richard J. Davies | |

It is certified that error appears in the above-identified patent and that said Letters Patent is hereby corrected as shown below:

At column 25, line 24, after "duct" insert --[551].--.

At column 37, line 44, "electrode" should read --electrodes--.

At column 37, line 52, "electrode" should read --electrodes--.

At column 38, line 1, "electrode" should read --electrodes--.

At column 38, line 9, "electrode" should read --electrodes--.

At column 38, line 27, "electrode" should read --electrodes--.

At column 38, line 35, "electrode" should read --electrodes--.

At column 38, line 44, "electrode" should read --electrodes--.

Signed and Sealed this
Thirteenth Day of March, 2012

David J. Kappos
*Director of the United States Patent and Trademark Office*